(12) United States Patent
Mukherjee et al.

(10) Patent No.: US 8,506,499 B2
(45) Date of Patent: Aug. 13, 2013

(54) PREDICTING ATRIAL FIBRILLATION RECURRENCE BY PROTEASE AND PROTEASE INHIBITOR PROFILING

(75) Inventors: Rupak Mukherjee, Charleston, SC (US); Michael R. Gold, Daniel Island, SC (US); Francis G. Spinale, Charleston, SC (US)

(73) Assignee: MUSC Foundation for Research Development, Charleston, SC (US)

( * ) Notice: Subject to any disclaimer, the term of this patent is extended or adjusted under 35 U.S.C. 154(b) by 612 days.

(21) Appl. No.: 12/522,238

(22) PCT Filed: Jan. 4, 2008

(86) PCT No.: PCT/US2008/000125
§ 371 (c)(1),
(2), (4) Date: Feb. 3, 2010

(87) PCT Pub. No.: WO2008/085895
PCT Pub. Date: Jul. 17, 2008

(65) Prior Publication Data
US 2011/0009861 A1    Jan. 13, 2011

Related U.S. Application Data

(60) Provisional application No. 60/883,459, filed on Jan. 4, 2007.

(51) Int. Cl.
*A61B 5/02* (2006.01)
(52) U.S. Cl.
USPC .......................................................... 600/508

(58) Field of Classification Search
USPC .................. 600/508, 342; 424/94.5; 435/23, 435/25, 4, 6.11, 6.14, 7.1, 7.92; 702/19
See application file for complete search history.

(56) References Cited

U.S. PATENT DOCUMENTS

| | | | |
|---|---|---|---|
| 3,817,837 | A | 6/1974 | Rubinstein |
| 3,850,752 | A | 11/1974 | Schuurs |
| 3,939,350 | A | 2/1976 | Kronick |
| 3,996,345 | A | 12/1976 | Ullman |
| 4,275,149 | A | 6/1981 | Litman |
| 4,277,437 | A | 7/1981 | Maggio |

(Continued)

FOREIGN PATENT DOCUMENTS

| | | |
|---|---|---|
| WO | 2007133905 | 11/2007 |
| WO | 2008008809 | 1/2008 |

OTHER PUBLICATIONS

Absi, et al., "Altered patterns of gene expression distinguishing ascending aortic aneurysms from abdominal aortic aneurysms: Complementary DNSA expression profiling in the molecular characterization of aortic disease", J Thorac Cardiovasc Surg., 126(2):344-57 (2003).

(Continued)

*Primary Examiner* — George Manuel
*Assistant Examiner* — Robert N Wieland
(74) *Attorney, Agent, or Firm* — Meunier Carlin & Curfman, LLC

(57) ABSTRACT

Disclosed herein are methods of and systems for predicting recurrence of atrial fibrillation comprising protease and protease inhibitor profiling. The levels of matrix metalloproteinases (MMPs) and/or tissue inhibitor metalloproteinases (TIMPs) are analyzed to predict the recurrence of atrial fibrillation, and further to predict whether cardioversion will provide a successful therapy.

47 Claims, 8 Drawing Sheets

(56) References Cited

U.S. PATENT DOCUMENTS

Figure 1:
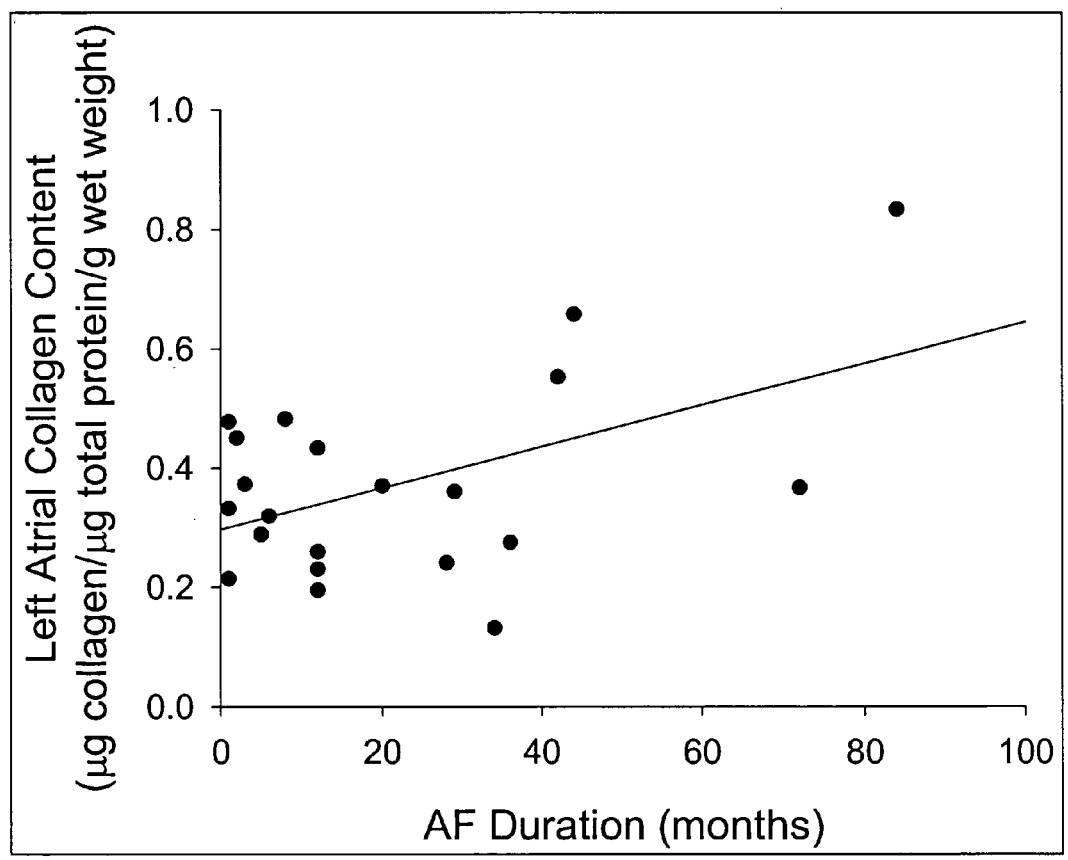

| | | | |
|---|---|---|---|
| 4,366,241 A | 12/1982 | Tom | |
| 4,376,110 A | 3/1983 | David | |
| 4,452,901 A | 6/1984 | Gordon | |
| 5,424,000 A | 6/1995 | Winicov | |
| 2004/0121343 A1* | 6/2004 | Buechler et al. | 435/6 |
| 2009/0005336 A1 | 1/2009 | Wang | |
| 2010/0010073 A1 | 1/2010 | Thum | |
| 2010/0267804 A1 | 10/2010 | Port | |
| 2011/0117560 A1 | 5/2011 | Spinale | |

OTHER PUBLICATIONS

Ahmed, at al., "Matrix metalloproteinases/tissue Inhibitors of metalloproteinases: Relationship between changes in proteolytic determinants of matrix composition and structural, functional and clinical manifestations of hypertensive heart desease", Circ., 113:2089-96 (2006).

Aime-Sempe, et al., "Myocardial cell death in fibrillating and dilated human right atria", J Am College of Cardiology, 34:1577-86 (1999).

Albinsson, et al., "MicroRNAs are necessary for vascular smooth muscle growth, differentiation, and function", Arterioscler Thromb Vasc Biol., 30 (6):1118-26 (2010).

Alla, et al., "Early changes in serum markers od cardiac extra-cellular matrix turnover in patients with uncomplicated hypertension and type II diabetes", Eur J Heart Fail., 8 (2):147-53 (2006).

Allessie, et al., "Electrical, contractile and structural remodeling during atrial fibrillation", Cardiovasc Res, 54:230-40 (2002).

Allessie, et al., "Pathophysiology and prevention of atrial fibrillation", Circ.,103:769-77 (2001).

Altieri, et al. "Metalloproteinases 2 and 9 are increased in plasma of patients with heart failure", Eur J of Clin Invest, 33:648-56 (2003).

Ambros, et al., "MicroRNAs and other tiny endogenous RNAs in C. elegans", Curr. Biol., 13(10):807-18 (2003).

Anderson, at al., "High resolution two-dimensional electrophoresis of human plasma proteins", PNAS, 74:5421-5 (1977).

Ausma, et al., "Reverse structural and gap-junctional remodeling after prolonged atrial fibrillation in the goat", Circulation, 107:2051-8 (2003).

Ausma, at al., "Structural changes of atrial myocardium due to sustained atrial fibrillation in the goat", Circulation, 96:3157-63 (1997).

Ausma, at al., "Time course of atrial fibrillation-induced cellular structural remodeling in atria of the goat", J Mol Cell Cardiol, 33:2083-94 (2001).

Baker, et al., "Metalloproteinase inhibitors: biological actions and therapeutic opportunities", J Cell Sci., 1115 (Pt 19):3719-27 (2002).

Bartel, "MicroRNAs: genomics, biogenesis, mechanism, and function", Cell, 116(2):281-97 (2004).

Bartel, "MicroRNAs: target recognition and regulatory functions", Cell, 136 (2):215-33 (2009).

Benjamin, at al, "Impact of atrial fibrillation on the risk of death: the Framingham Heart Study", Circulation, 98:946-52 (1998).

Bigg, et al., "Tissue inhibitor of metalloproteinase-4 inhibits but does not support the activation of gelatinase A via efficient inhibition of membrane type 1-matrix metalloproteinase", Cancer Res, 61(9): 3610-8 (2001).

Blankenberg, et al., "Plasma Concentrations and Genetic Variation of Matrix Metalloproteinase 9 and Prognosis of Patients With Cardiovascular Disease", Circulation, 107:1579-85 (2003).

Boldt, et al., "Fibrosis in left atrial tissue of patients with atrial fibrillation with and without underlying mitral valve disease", Heart, 90:400-05 (2004).

Bollmann, et al., "Atrial fibrillatory frequency predicts atrial defibrillation threshold and early arrhythmia recurrence in patients undergoing internal cardioversion of persistent atrial fibrillation", Pacing Clin Electrophysiol , 25:1179-84 (2002).

Borden, et al., "Transcriptional control of matrix metalloproteinases and the tissue inhibitors of matrix metalloproteinases", Crit Rev Eukaryot Gene Exp, 7:159-78 (1997).

Borges, et al., "Tissue diffusion and retention of metalloproteinases in ascending aortic aneurysms and dissections", Human pathology., 40(3):306-13 (2009).

Boyum, et al., "Matrix metalloproteinase activity in thoracic aortic aneurysms associated with bicuspid and tricuspid aortic valves", J Thorac Cardiovasc Surg., 127(3):686-91(2004).

Bradham, et al "Differential release of matrix metalloproteinases (MMP\s) and tissue inhibitors of matrix metalloproteinases (TIMP\s) in patients following alcohol induced myocardial infarction", J Am Coil Cardiol, 40(12):2165-73 (2002).

Brew, et al., "Tissue inhibitors of metalloproteinases: evolution,structure and function", Biochim Biophys Acta., 1477:267-83 (2000).

Brundel, et al., "Molecular mechanisms of remodeling in human atrial fibrillation", Cardiovascular Res, 54:315-24 (2002).

Butler, "Enzyme-linked immunosorbent assay", Structure of Antigens, vol. 1 (Van Oss, et al. (eds.) Immunochem, Marcel Dekker, Inc., New York, 1994, 759-803 (1994).

Butler, "The amplified ELISA: principles of and applications for the comparative quantitation of class and subclass antibodies and the distribution of antibodies and antigens in biochemical separates", Methods Enzymol., 73:482-523 (1981).

Butler, "The behavior of antigens and antibodies immobilized on a solid phase", Structure of Antigens, vol. 1 (Van Regenmortel, M., CRC Press, Boca Raton, 209-59 (1992).

Caterina, et al., "Glycosylation and NH2-terminal domain mutant of tissue inhibitor of metalloproteinases-1 (TIMP-1)" . Biochem Biophys Acta, 1388: 21-34 (1998).

Chapman and Spinale, "Extracellular protease activation and unraveling of the myocardial interstitium: critical steps toward clinical applications", Am J Physiol.

Chareonthaitawee, et al., "Relation of initial infarct size to extent of left ventricular remodeling in the year after acute myocardial infarction", J Am Coil Cardiol, 25:567-73 (1995).

Chen, et al., "Characterization of microRNAs in serum: a novel class of biomarkers for diagnosis of cancer and other diseases", Cell Res., 18:997-1006 (2008).

Chobanian, et al., National Heart, Lung, and Blood Institute Joint National Committee on Prevention, Detection, Evaluation, and Treatment of High Blood Pressure; National High Blood Pressure Education Program Coordinating Committee. The Seventh Report of the Joint National Committee on Prevention, Detection, Evaluation, and Treatment of High Blood Pressure; the JNC 7 report. JAMA. 2003;289:2560-72.

Chung, et al, "Loss of elastic fiber Integrity and reduction of vascular smooth muscle contraction resulting from the upregulated activities of matrix metalloproteinase-2 and -9 in the thoracic aortic aneurysm in Marfan syndrome", Circ Res.,101(5):512-22 (2007).

Coker, et al., "Matrix metalloproteinase expression and activity in isolated LV myocyte preparations following neurohormonal stimulation", Am J Physiol, 281:H543-H551 (2001).

Creemers, et al., "Deficiency of TIMP-1 exacerbates LV remodeling after myocardial infarction in mice", Am J Physiol, 284:H364-371 (2002).

Creemers, et al., "Matrix Metalloproteinase Inhibition After Myocardial Infarction: A new approach to prevent heart failure", Circulation Res, 89;201-210 (2001).

Crowther, "Elisa: Theory and Practice," Methods Mol Biol, 42:1-218 (1995).

Damodarasamy, et al., "Collagen Extracts Derived From Young and Aged Mice Demonstrate Different Structural Properties and Cellular Effects in Three-Dimensional Gels", J Gerontol A Biol Sci Med Sci., 65(3):209-18 (2010).

Deisenhofer, et al., "Circumferential mapping and electric isolation of pulmonary veins in patients with atrial fibrillation", Am J Cardiology, 91:159-63 (2003).

Dennis, et al., "Protein glycosylation in development and disease", BioEssays, 21.

Deschamps, et al., "Pathways of matrix metalloproteinase induction in heart failure: Bioactive molecules and transcriptional regulation", Cardiovasc Res, 69:666-76 (2006).

Devereux, et al., Echocardiographic assessment of left ventricular hypertrophy.

Diez, et al., "Losartandependent regression of myocardial fibrosis is associated with reduction of left ventricular chamber stiffness in hypertensive patients", Circulation, 105:2512-17 (2002).

Dispersyn, et al., "Cardiomyocyte remodelling during myocardial hibernation and atrial fibrillation: prelude to apoptosis", Cariovasc Res, 43:947-57 (1999).

Divakaran and Mann, "The Emerging Role of MicroRNAs in Cardiac Remodeling and Heart Failure", Ciro Res., 103:1072-83 (2008).

Dong, et al., "MicroRNA Expression Signature and the Role of MicroRNA-21 in the Early Phase of Acute Myocardial Infarction", J Biol Chem., 284(43):29514-25 (2009).

Douglas, et al., "Computational sequence analysis of the tissue inhibitor of metalloproteinase family", J. Protein Chem, 16:237-55 (1997).

Ducharme, et al., "Targeted deletion of matrix metalloproteinase-9 attenuates left ventricular enlargement and collagen accumulation after experimental myocardial infarction", J Clin Invest, 106:55-62 (2000).

Duisters, et al., "miR-133 and miR-30 Regulate Connective Tissue Growth Factor. Implications for a Role of MicroRNAs in Myocardial Matrix Remodeling", Circ Res, 104:170-8 (2009).

Edwards, et al., "The roles of tissue inhibitors of metalloproteinases in tissue remodeling and cell growth", Intl. J Obes Metab Disord., 20;S9-S15 (1996).

Elia, et al., "The knockout of miR-143 and -145 alters smooth muscle cell maintenance and vascular homeostasis in mice: correlates with human disease", Cell Death Differ., 16 (12):1590-98 (2009).

Erlebacher, et al., "Early dilation of the infarcted segment in acute transmural myocardial infarction: role of infarct expansion in acute left ventricular enlargement", J Am Coil Cardiol, 4(2)201-8 (1984).

Esteve, et al., "Protein kinase C-zeta regulates transcription of the matrix metalloproteinase-9 gene induced by IL-i and TNF-alpha in glioma cells via NF-kappa B", J Biol Chem, 277(38):35150-5 (2002).

Etoh, et al., "Myocardial and interstitial matrix metalloproteinase activity after acute myocardial infarction in pigs", Am J Physiol Heart Circ Physiol, 281:H987-H994 (2001).

Falcone, et al., "Plasma Levels of Soluble Receptor for Advanced Glycation End Products and Coronary Artery Disease in Nondiabetic Men", Arterioscler Thromb Vasc Biol, 25:1032-7 (2005).

Felkin, et al., "A quantitative gene expression profile of matrix metalloproteinases (MMPS) and their inhibitors (TIMPS) in the myocardium of patients with deteriorating heart failure requiring left ventricular assist device support.", J Heart Lung Transpl., 25:1413-19 (2006).

Fini, et al., "Regulation of matrix metalloproteinase gene expression", Matrix Metalloproteinases. San Diego: Academic, 299-356, (1998).

Fragakis, et al., "Reversion and maintenance of sinus rhythm in patients with permanent atrial fibrillation by internal cardioversion followed by biatrial pacing", Pacing Clin Electrophysiol 25:278-86 (2002).

Frick, et al., "Factors predicting success rate and recurrence of atrial fibrillation after first electrical cardioversion in patients with persistent atrial fibrillation", Clin Cardiol, 24:238-44 (2001).

Friedman, et al., "Most mammalian mRNAs are conserved targets of microRNAs", Genome Res. 19(1):92-105 (2009).

Frustaci, et al., "Histological Substrate of Atrial Biopsies in Patients With Lone Atrial Fibrillation", Circulation, 96:1180-4 (1997).

Galis and Khatri, "Matrix metalloproteinases in vascular remodeling and atherogenesis: the good, the bad and the ugly", Circ Res., 90: 251-62 (2002).

Goette, et al., "Calpains and cytokines in fibrillating human atria", Am J Physiol Heart Circ Physiol, 283:H264-H272 (2002).

Goffin, et al., "Expression pattern of metalloproteinases and tissue inhibitor of matric metalloproteinases in cycling human endometrium", Biol Reprod, 69:976-84 (2003).

Goldberg, et al., "Human 72-kilodalton type IV collagenase forms a complex with a tissue inhibitor of metaqlloproteinase designated TIMP", PNAS, 86:8207-11 (1989).

Gomez, et al., "Tissue inhibitor of metalloproteinases: structure, regulation, and biological functions", EJCB, 74:111-12 (1997).

Greene, et al., "Molecular cloning and characterization of human tissue inhibitor of metalloproteinase 4", J Biol Chem 271(48):30375-80 (1996).

Grimson, et al., "MicroRNA targeting specificity in mammals: determinants beyond seed pairing", Mol Cell., 27(1):91-105 (2007).

Grishok, et al., "Genes and mechanisms related to RNA interference regulate expression of the small temporal RNAs that control C. elegans developmental timing", Cell, 106(1):23-34 (2001).

Gross, et al., "Collagenolytic activity in amphibian tissues: a tissue culture assay", PNAS,48:1014-22 (1962).

Gunasinghe, et al., "Contributory role of matrix metalloproteinases in cardiovascular remodeling", Cardiovasc & Haemato Disorders, 1(2):75-91(1996).

Gunja-Smith, et al., "Remodeling of human myocardial collagen in idiopathic dilated cardiomyopathy: role of metalloproteinases and pyridinoline cross links", Am J Path, 148:1639-48 (1996).

Haro, et al., "Matrix metalloproteinase-7 dependent release of tumor necrosis factor alpha in a model of herniated disc resorption", J Clin Invest 105:143-50 (2000).

Herman, et al., "Expression of neutrophil collagenase (matrix metalloproteinase-8) in human atheroma: a novel collagenolytic pathway suggested by transcriptional profiling", Circulation 104;1878-80 (2001).

Heymans, et al., "Inhibition of plaminogen activators or matrix metalloproteinases prevents cardiac rupture but impairs therapeutic angiogenesis and causes cardiac failure", Nature Med 5:1135-42 (1999).

Hirohata, et al., "Time dependent alterations of serum matrix metalloproteinase-1 and metalloproteinase-1 tissue inhibitor after successful reperfusion of acute myocardial infarction", Heart, 78:278-84 (1997).

Hobbs, et al., "Reversal of atrial electrical remodeling after cardioversion of persistent atrial fibrillation in humans", Circulation, 101:1145-51 (2000).

Hofmann, et al., "RAGE mediates a novel proinflammatory axis: a central cell surface receptor for S100/calgranulin polypeptides", Cell, 97:889-901(1999).

Hojo, et al., "Expression of matrix metalloproteinases in patients with acute myocardial infarction", Jpn Circ J, 65; 71-75 (2001).

Holmbeck, et al., "MT1-MMP: a tethered collagenase", J Cell Physiol, 200:11-9 (2004).

Hunt, et al., "The amino-terminal portion of pro-brain natriuretic peptide (Pro-BNP) circulates in human plasma", Biochem Biophys Res Commun. 214:1175-83 (1995).

Ikonomidis, et al., "Effects of deletion of the matrix metalloproteinase 9 gene on development of murine thoracic aortic aneurysms", Circulation, 112(9 Suppl):I242-8 (2005).

Ikonomidis, et al., "Expression of matrix metalloproteinases and endogenous inhibitors within ascending aortic aneurysms of patients with bicuspid or tricuspid aortic valves", J Thorac Cardiovasc Surg. 133(4):1028-36 (2007).

Ikonomidis, et al., "Expression of matrix metalloproteinases and endogenous inhibitors within ascending aortic aneurysms of patients with Marfan syndrome", Circulation., 114(1 Suppl):I365-70 (2006).

Inokubo, et al., "Plasma levels of matrix metalloproteinase-9 and tissue inhibitor of metalloproteinase-1 are increased in the coronary circulation in patients with acute coronary syndrome", Am Heart J, 141:211-7 (2001).

Isselbacher, "Thoracic and abdominal aortic aneurysms", Curr., 111 (6):816-28 (2005).

Joffs, et al., "Cardiopulmonary bypass induces the synthesis and release of matrix metalloproteinases", Ann Thorac Surg., 71:1518-23 (2001).

Jones, et al., "Alterations in membrane type-1 matrix metalloproteinase abundance after the induction of thoracic aortic aneurysm in a murine model", Am J Physiol Heart Circ Physiol. 299(1):H114-24 (2010).

Jones, et al., "Selective microRNA suppression in human thoracic aneurysms: relationship of miR-29a to aortic size and proteolytic induction", Circ Cardiovasc Genet, 4(6):605-13 (2011).

Jones, et al., "Spatiotemporal expression and localization of matrix metalloproteinase-9 in a murine model of thoracic aortic aneurysm", J Vasc Surg., 44(6)1314-21(2006).

Kaden, et al., "Time dependent changes in the plasma concentration of matrix metalloproteinase 9 after acute myocardial infarction", Cardiology, 99:140-4 (2003).

Kai, et al., "Peripheral blood levels of matrix metalloproteases-2 and -9 are elevated in patients with acute coronary syndromes", J Am Coll Cardiol, 32:368-72 (1998).

Kalousova, et al, "Receptor for advanced glycation end products" soluble form and gene polymorphisms in chronic haemodialysis patients, Nephrol Dial.

Kenchaiah and Pfeffer, "Cardiac remodeling in systemic hypertension", Med Clin N Am., 88:115-30 (2004).

Kostin, et al., "Structural correlate of atrial fibrillation in human patients", Cardiovas.Res., 54:361-79 (2002).

Kozomara, et al., "miRBase: integrating microRNA annotation and deep-sequencing sequencing data", Nucleic Acids Res., 39(Database issue):D152-157 (2011).

Laemmli, "Cleavage of structural proteins during the assembly of the head of bacteriophage T4", Nature, 227:680-5 (1970).

Lagos-Quintana, et al., "Identification of novel genes coding for small expressed RNAs", Science, 294(5543):853-8 (2001).

Lakatta and Levy, "Arterial and cardiac aging: major shareholders in cardiovascular disease enterprises: Pt I: aging arteries: a "set up" for vascular disease", Circulation,107(1):139-46 (2003).

Lau, et al., "An abundant class of tiny RNAs with probable regulatory roles in *Caenorhabditis elegans*", Science, 294(5543):858-62 (2001).

Laviades, et al., "Abnormalities of the extracellular degradation of collagen type I in essential hypertension",Circulation., 98(6):535-40 (1998).

Lee and Ambros, "An extensive class of small RNAs in *Caenorhabditis elegans*", Science, 294(5543):862-4 (2001).

Lellouche, et al., "Usefulness of plasma B-type natriuretic peptide in predicting recurrence of atrial fibrillation one year after external cardioversion", Am J Cardiol,95:1380-82 (2005).

Lemaire, et al., "Matrix metalloproteinases in ascending aortic aneurysms: bicuspid versus trileaflet aortic valves", J Surg Res,123(1):40-8 (2005).

Levy, et al., "The progression from hypertension to congestive heart failure". JAMA, 275:1557-62 (1996).

Lewis, et al., "Conserved seed pairing, often flanked by adenosines, indicates that thousands of human genes are microRNA targets", Cell., 120(1)15-20 (2005).

Li, et al., "Attenuation of micro-RNA-1 derepresses the cytoskeleton regulatory protein twinfilin-1 to provoke cardiac hypertrophy", J Cell Sci., 123(pt14):2444-52 (2010).

Li, et al., "Differential expression of tissue inhibitors of metalloproteinases in the failing human heart", Circ., 98;1728-34 (1998).

Li, et al., "Downregulation of matrix metalloproteinases and reduction in collagen damage in the failing human heart after support with left ventricular assist devices", Circ,104:1147-52 (2001b).

Li, et al., "Matrilysin shedding of syndecan-1 regulates chemokine mobilization and transepithelial efflux of neutrophils in acture lung injury", Cell ,111:635-46 (2002).

Li, et al., MMP/TMP expression in spontaneously hypertensive heart failure rats: the effect of ACE and MMP-inhibition, Cardio Res, 46:298-306 (2000).

Li, et al., "Proinflammatory cytokines regulate tissue inhibitors of metalloproteinases and disintegrin metalloproteinase in cardiac cells", Cardiovasc Res., 42(1):162-72 (1999).

Li, et al., "Real-Time Polymerase Chain Reaction MicroRNA Detection Based on Enzymatic Stem-Loop Probes Ligation", Anal Chem., 1:81(13):5446-51 (2009).

Li-Saw-Hee, et al., "Lip GYH: Matrix metalloproteinase-9 and tissue inhibitor metalloproteinase-1 levels in essential hypertension. Relationship to left ventricular mass and anti-hypertensive therapy", Int J Cardiol. 75:43-7 (2000).

Li and Wong, "Model-based analysis of oligonucleotide arrays: expression index computation and outlier detection", PNAS, 98(1):31-6 (2001a).

Liao, et al., "A microRNA profile comparison between thoracic aortic dissection and normal thoracic aorta indicates the potential role of microRNAs in contributing to thoracic aortic dissection pathogenesis", J Vasc Surg., 53(5):1341-9.e3 (2011).

Liao, et al.," Cardiotrophin-1 (CT-1) can protect the adult heart from injury when added both prior to ischaemia and at reperfusion", Cardiovasc. Res., 53:902-10 (2002).

Lin, et al., "Predictors of clinical recurrence after successful electrical cardioversion of chronic persistent atrial fibrillation: clinical and electrophysiological observations", Cardiol., 97:133-7 (2002).

Lindsay, et al., "TIMP-1. A marker of left ventricular diastolic dysfunction and fibrosis in hypertenstion", Hypertension, 40:136-41 (2002).

Lindsey, et al., "Extracellular matrix remodeling following myocardial injury", Ann Med., 35:316-26 (2003).

Liu, et al., "Identification and characteristics of microRNAs with altered expression patterns in a rat model of abdominal aortic aneurysms", Tohoku J Exp Med., 222 (3):187-93 (2010).

Liu, et al., "microRNA-133a regulates cardiomyocyte proliferation and suppresses smooth muscle gene expression in the heart", Genes Dev., 22(23):3242-54 (2008).

Liu, et al., "Preparation and characterization of recombinant tissue inhibitor of metaloproteinase 4", Am Soc Biochem Mol Biol, , 272:20479-83 (1997).

Liu, et al., "Renal medullary microRNAs in Dahl salt-sensitive rats: miR-29b regulates several collagens and related genes", Hypertension, 55(4):974-82 (2010b).

Lloyd-Jones,et al., "Lifetime risk for developing congestive heart failure;The Framingham Study", Circ., 06:3068-72 (2002).

Longo, et al., "Matrix metalloproteinases 2 and 9 work in concert to produce aortic aneurysms", J Clin Invest. 110(5):625-32 (2002).

Lopez, et al., "Biochemical assessment of myocardial fibrosis in hypertensive heart disease", Hypertension, 38:1222-26 (2001b).

Lopez, et al., "Usefulness of serum carboxy-terminal propeptide of procollagen type I in assessment of the cardioreparative ability in antihypertensive treatment in hypertensive patients" ,Circ, 104:288-91 (2001a).

Mair, et al., "The impact of cardiac natriuretic peptide determination on the diagnosis and management of heart failure", Clin Chem Lab Med., 39:571-88 (2001).

Marin, et al., "Is Thrombogenesis in Atrial Fibrillation Related to Matrix Metalloproteinase-1 and Its Inhibitor, TIMP-1" , Stroke,34:1181-6 (2003).

Maron, et al.," Hypertrophic cardiomyopathy: a systematic review", JAMA, 287:1308-20 (2002).

Matrisian, "Metalloproteinases and their inhibitors in matrix remodeling", Trends in Genetics, 6:121-5 (1990).

Matsudaira,et al., "SDS microslab linear gradient polyacrylamide gel electrophoresis", Anal Biochem, 87:386-96 (1987).

McMillan, et al., "In situ localization and quantification of mRNA for 92-kD type IV collagenase and its inhibitor in aneurysmal, occlusive, and normal aorta", Arterioscler Thromb Vasc Biol. 15(8)1139-44 (1995a).

McMillan, et al., "In situ localization and quantification of seventy-two-kilodalton type IV collagenase in aneurysmal, occlusive, and normal aorta", J Vasc Surg, 22 (3):295-305 (1995b).

Mitchell, et al., "Circulating microRNAs as stable blood-based markers for cancer detection", PNAS, 105(30):10513-8 (2008).

Montaner, et al., "Matrix Metalloproteinase Expression Is Related to Hemorrhagic Transformation After Cardioembolic Stroke", Stroke, 32:2762-7 (2001b).

Montaner, et al., "Matrix metalloproteinase-9 pretreatment level predicts intracranial hemorrhagic complications after thrombolysis in human stroke", Circ, 107:598-603 (2003).

Montaner , et al., "Matrix Metalloproteinase Expression After Human Cardioembolic Stroke: Temporal Profile and Relation to Neurological Impairment", Stroke, 32:1759-66 (2001).

Moon, et al., "ERK1/2 mediates TNF-alpha induced matrix metalloproteinase-9 expression in human vasuclar smooth muscle cells via the regulation of NF-kappaB and AP-1: Involvement of the ras dependent pathway", J Cell Physiol., 198:417-27 (2004).

Mukherjee, et al., "Myocardial infarct expansion and matrix metalloproteinase inhibition", Circulation, 107(4):618-25 (2003).

Nagase, "Activational mechansims of matrix metalloprteinases", Biol Chem., 378:151-60 (1997).

Nagueh, et al., "Changes in left ventricular diastolic function 6 months after nonsurgical septal reduction therapy for hypertrophic obstructive cardiomyopathy", Circ., 93:344-7 (1999a).

Nagueh, et al., "Changes in left ventricular filling and left atrial function six months after nonsurgical septal reduction therapy for hypertrophic obstructive cardiomyopathy", J Am Coil Cardiol, 34;1123-8 (1999b).

Nagueh, et al., "Decreased expression of tumor necrosis factor-alpha and regression of hypertrophy after nonsurgical septal reduction therapy for patients with hypertrophic obstructive cardiomyopathy", Circ., 103(14):1844-50 (2001).

Nagueh, et al., "Doppler estimation of left ventricular filling pressure in sinus tachycardia. A new application of tissue Doppler imaging", Circ., 98:1644-50 (1998).

Neuhoff, et al., "Clear background and highly sensitive protein staining with Coomassie Blue dyes in polyacrylamide gels: A systematic analysis", Electrophoresis, 6:427-48 (1985).

Neuhoff, et al., "Improved staining of proteins in polyacrylamide gels Including isoelectric focusing gels with clear background at nanogram sensitivity using Coomassle Brilliant Blue G-250 and R-250", Electrophoresis, 9:255-262 (1988).

O'Farrell, "High Resolution Two-dimensional Electrophoresis of Proteins", J Biol Chem, 250:4007-21 (1975).

Ornstein, "Disc electrophoresis—I: Background and theory", Ann. NY Acad. Sci., 121:321-49 (1964).

Parsons, et al., "Matrix metalloproteinases", Brit J Surg, 84:160-6 (1997).

Peterson, et al., "Evolution of matrix metalloproteinase and tissue inhibitor expression during heart failure progression in the infracted rat", Cardiovas Res, 46:307-15 (2000).

Peterson, et al., "Matrix metalloproteinase inhibition attenuates left ventricular remodeling and dysfunction in a rat model of progressive heart failure", Circ,103 118): 2303-9 (2001).

Pfeffer, et al., "Ventricular remodeling after myocardial infarction. Experimental observations and clinical implications", Circ., 81:1161-72 (1990).

Pozzoli, et al., Predictors of primary atrial fibrillation and concomitant clinical and hemodynamic changes in patients with chronic heart failure: a prospective study in 344 patients with baseline sinus rhythm', J Am Coll Cardia, 32:197-204 (1998).

Psaty, et al., "Incidence of and risk factors for atrial fibrillation in older adults", Circ., 96:2455-61 (1997).

Qin and Zhang, "MicroRNAs in vascular disease", J Cardiovasc Pharmacol., 57 (1):8-12 (2011).

Radomski, et al.,"Identification, regulation and role of tissue of tissue inhibitor of metalloproteinases-4 (TIMP-4) in human platelets", Br J Pharmaco 137 (8):1130-8 (2002).

Rohde, et al., "Matrix metalloproteinase inhibition attenuates early left ventricular enlargement after experimental myocardial infarction in mice", Circ, 99:3063-70 (1999).

Roy, et al., "MicroRNA expression in response to murine myocardial infarction: miR-21 regulates fibroblast metalloprotease-2 via phosphatase and tensin homologue", Cardiovasc Res., 82(1):21-9 (2009).

Sahn, et al., "Recommendations regarding quantitation in M-mode echocardiography:results of a survey of echocardiographic measurements", Circ., 58:1072-83 (1978).

Sanfilippo, et al., "Atrial enlargement as a consequence of atrial fibrillation. A prospective echocardiographic study", Circ., 82:792-7 (1990).

Sawicki, et al., "Release of gelatinase A during platelet activation mediates aggregation", Nature, 386:616-9 (1997).

Schillaci, et al., "Prognostic significance of left ventricular diastolic dysfunction in essential hypertension", J Am Coil Cardiol., 39:2005-11 (2002).

Schiller, et al., "Recommendations for quantitation of the left ventricle by two-dimensional echocardiography. American Society of Echocardiography Committee on Standards, Subcommittee on Quantitation of Two-Dimensional Echocardiograms.", J Am Soc Enchocaridlogr., 2(5): 358-67 (1989).

Schleicher, et al., "Increased accumulation of the glycoxidation product N (epsilon)-(carboxymethyl)lysine in human tissues in diabetes and aging", J. Clin. Invest. , 99(3):457-68 (1997).

Schotten, et al., "Cellular mechanisms of depressed atrial contractility in patients with chronic atrial fibrillation", Circ., 103: 691-8 (2001).

Schotten, et al., "Electrical and contractile remodeling during the first days of atrial fibrillation go hand in hand", Circ., 107:1433-9 (2003).

Schulz-Menger, et al., "The value of magnetic resonance imaging of the left ventricular outflow tract in patients with hyupertrophic obstructive cardiomyopahty after septal artery embolization", Circ., 101:1764-6 (2000).

Schulze, et al., "Imbalance between tissue inhibitor of metalloproteinase-4 and matrix metalloproeinases during acute myocardial ischemia-reperfusion injury", Circ, 107:2487-92 (2003).

Schwartz, et al., "Impact of pre-existing conditions, age and the length of cardiopulmonary bypass on postoperative outcome after repair of the ascending aorta and aortic arch for aortic aneurysms and dissections", Interact Cardlovasc. Thorac Sup., 7(5):850-4 (2008).

Schwartzkopff, et al., "Elevated serum markers of collagen degradation in patients with mid to moderate dilated cardiomyopathy", Eur. J Heart Fail., 4:439-44 (2002).

Sen, et al., "Micromanaging vascular biology: tiny microRNAs play big band", J Vasc Res., 46(6):527-40 (2009).

Sharp, et al. , "Serum levels of low molecular weight advanced glycation end products in diabetic subjects", Diabet Med, 20(7): 575-9 (2003).

Sheng, et al., "Cardiotrophin-1 displays early expression in the murine heart tube and promotes cardiac myocyte survival", Development, 122:419-28 (1996).

Shirwany, et al., "Extracellular matrix remodeling in hypertensive heart disease", J of Am College of Cardiology, 48:97-98 (2006).

Sinha, et al., "A biologic basis for asymmetric growth in descending thoracic aortic aneurysms: a role for matrix metalloproteinase 9 and 2", J Vasc Surg., 43 (2):342-8 (2006).

Siwik, et al., "Oxidative stress regulates collagen synthesis and matrix metalloproteinase activity in cardiac fibroblasts", Am J Phys., 280:C53-60 (2001).

Small, et al., "MicroRNAs Add a New Dimension to Cardiovascular Disease", Circ., 121:1022-32 (2010).

Spencer, et al., "Alcohol septal ablation in hypertrophic obstructive cardiomyopathy: the need for registry", Circ., 102;600-01 (2000).

Spinale, et al., "A matrix metalloproteinase induction/activation system exists in the human myocardium and is unregulated in heart failure", Circ., 102;1944-9 (2000).

Spinale, et al., "Extracellular degradative pathways in myocardial remodeling and progression to heart failure", J Cardiac Failure, 8:S332-8 (2002).

Spinale, et al., "Matrix metalloporeinase inhibition during developing congestive heart failure in pigs: effects on left ventricular geometry and function", Circ Res, 85:364-76 (1999).

Spinale, et al., "Time-dependent changes in matrix metalloproteinase activity and expression during the progression of congestive heart failure: relation to ventricular and myocyte function", Circ. Res., 82 (4):482-95 (1998).

Spinale, "Chronic matrix metalloproteinase inhibition following myocardial infarction in mice: Differential effects on short and long-term survival", J Pharmacol. Exp. Ther., 318 (3):966-73 (2006).

Spinale, "Matrix metalloproteinases. Regulation and dysregulation in the failing heart", Circ. Res., 90:520-30 (2002).

St. John Sutton, et al., "Quantitative two-dimensional echocardiographic measurements are major predictors of adverse cardiovascular events after myocardial infarction. The protective effects of captopril", Circ., 89;68-75 (1994).

Steele, et al., "MBP-1 upregulates miR-29b that represses Mcl-1, collagens, and matrix-metalloproteinase-2 in prostate cancer cells", Genes Cancer, 1 4):381-7 (2010).

Steinberg, et al., "Rapid and simple single nanogram detection of glycoproteins in polyacrylamide gels on electroblots", Proteomics, 1(7): 841-55 (2000).

Stroud, et al., "Plasma monitoring of the myocardial specific tissue inhibitor of metalloproteinase-4 after alcohol septal ablation in hypertrophic obstructive cardiomyopathy", J Card Fail, 11:124-30 (2005).

Sundstrom, et al., "Relations of plasma matrix metalloproteinase-9 to clinical cardiovascular risk factors and echocardiographic left ventricular measures: the Framingham Heart Study", Circulation, 109:2850-56 (2004).

Tamarina, et al., "Expression of matrix metalloproteinases and their inhibitors in aneurysms and normal aorta", Surgery, 122(2):264-71; discussion 271-262 (1997).

Tayebjee, et al., "Matrix metalloprotelnase-9 and tissue inhibitor of metalloproteinase-1 in hypertension and their relationship to cardiovascular risk and treatment: a substudy of the Angio-Scandinavian Cardiac Outcomes Trial (ASCOT)", Am J Hypertens.,17:764-9 (2004).

Tayebjee, et al., "Tissue inhibitor of metalloproteinase-1 and matrix metalloproteinase-9 levels in patients with hypertension Relationship to tissue Doppler indices of diastolic relaxation", Am J Hypertens., 17:770-4 (2004).

Tayebjee, et al., "Tissue inhibitor of metalloproteinse-1 is a marker of diastolic dysfunction using tissue doppler in patients with type 2 diabetes and hypertension", Eur J Clin Invest.35:8-12 (2005).

Thijssen, et al., "Structural remodelling during chronic atrial fibrillation: act of programmed cell survival", Cardiovas Res, 52:14-24 (2001).

Thomas, et al., "Increased matrix metalloproteinase activity and selective upregulation inLV myocardium from patients with end-stage dilated cardiomyopathy", Circ, 97:1708-15 (1998).

Timms, et al., "Plasma tissue inhibitor of metalloproteinase-1 levels are elevated in essential hypertension and related to left ventricular hypertrophy", Am J Hyper,15:269-72 (2002).

Todd, et al., "Prevalence and significance of focal sources of atrial arrhythmia in patients undergoing cardioversion of persistent atrial fibrillation", J Cardiovasc Electrophysiol., 11:616-22 (2000).

Tsuruda, et al., "Matrix metalloproteinases: pathways of induction by bioactive molecules", Heart Fail Rev., 9:53-61 (2004).

Tziakes, et al., "N-terminal pro-B-type natriuretic peptide and matrix metalloproteinases in early an dlate left ventricular remodeling after acute myocardial infarction", Am J Cardio., 96:31-4 (2005).

U.S. Appl. No. 12/307,985 Prosecution history.

U.S. Appl. No. 12/299,999 Prosecution history.

Van Gelder, et al., "Prediction of uneventful cardioversion and maintenance of sinus rhythm from direct-current electrical cardioversion of chronic atrial fibrillation and flutter", Am J Cardiol. 68:41-6 (1991).

van Rooij, et al. "Dysregulation of microRNAs after myocardial infarction reveals a role of miR-29 in cardiac fibrosis", PNAS, 105(35):13027-32 (2008).

Vincenti, "The matrix metalloproteinase (MMP) and tissue inhibitor of metalloproteinase (TIMP) genes. Transcriptional and post-transcriptional regulation, signal transduction and cell-type-specific expression", Methods Mol Biol., 151:121-48 (2001).

Visse, et al., "Matrix metalloproteinases and tissue inhibitors of metalloproteinases: structure, function, and biochemistry", Circ Res., 92:827-39 (2003).

Voller, et al., "Enzyme immunoassays with special reference to ELISA techniques", J Clin. Pathol., 31:507-20 (1978).

Vu and Werb, "Matrix metalloproteinases: effectors of development and normal physiology", Genes Dev., 14:2123-33 (2000).

Wachtell, et al., "Left ventricular filling patterns in patients with systemic hypertension and left ventricular hypertrophy (The Life Study)", Am J Cardiol., 85:466-72 (2000).

Wassef, et al., "Pathogenesis of abdominal aortic aneurysms: a multidisciplinary research program supported by the National Heart, Lung, and Blood Institute", J Vas Surg, 34:730-8 (2001).

Wautier, et al., "Receptor-mediated endothelial cell dysfunction in diabetic vasculopathy. Soluble receptor for advanced glycation end products blocks hyperpermeability in diabetic rate", J. Clan. Invest. 97:238-43 (1996).

Wazni, et al., "C reactive protein concentration and recurrence of atrial fibrillation after electrical cardioversion", Heart, 91:1303-5 (2005).

Webb, et al., "Specific temporal profile of matrix metalloproteinase release occurs in patients after myocardial infarction: relation to left ventricular remodeling", Circulation, 114 (10)1020-27 (2006).

Weber, et al., "Pathological hypertrophy and cardiac interstitium: Fibrosis and renin-angiotensin-aldosterone system", Circ., 83:1849-65 (part 1) (1991).

Weber, et al., "Pathological hypertrophy and cardiac interstitium: Fibrosis and renin-angiotensin-aldosterone system", Circ., 83:1849-65 (part 2) (1991).

Weber, et al., "Structural remodeling in hypertensive heart disease and the role of hormones", Hypertension, 23:869-77 (1994).

White, et al., "Left ventricular end-systolic volume as the major determinant of survival after recovery from myocardial infarction", Circ., 76(1):44-51 (1987).

Wilson, et al., "Plasma matrix metalloproteinase and inhibitor profiles in patients with heart failure", J Card Fail., 8:390-98 (2002).

Wilson, et al., "Region and type-specific induction of matrix metalloproteinases occurs with post-myocardial infarction remodeling", Circ., 107(22):2857-63 (2003).

Woessner, et al., "Activation of the zymogen forms of MMPs", Matrix metalloproteinase and TIMPs. Oxford Univerity Press, Oxford UK, pp. 72-86 (2000).

Woessner, et al., "The matrix metalloproteinase family", Matrix metalloproteinases. Parks WC, Mecham RP, eds. Academic Press, San Diego. Ppl-14 (1998).

Wyse, et al., "A Comparison of Rate Control and Rhythm Control in Patients with Atrial Fibrillation", N. Engl J Med ., 347:1825-33 (2002).

Xu, et al., "The Drosophila microRNA Mir-14 suppresses cell death and is required for normal fat metabolism", Curr. Biol., 13(9):790-5 (2003).

Yang, et al., "Advances in diastolic heart failure", World J Cardiol., 2(3):58-63 (2010).

Yarbrough, et al., "Selective targeting and timing of matrix metalloproteinase inhibition in post-myocardial infarction remodeling", Circ., 108:1753-59 (2003).

Yasmin, et al., "Matrix metalloproteinase-9 (MMP-9), MMP-2, and serum elastase activity are associated with systolic hypertension and arterial stiffness", Arterioscler Thromb Vasc Biol., 25 (2):372 (2005).

Yu, et al., "Reversal of atrial electrical remodeling following cardioversion of long-standing atrial fibrillation in man", Cardiovas. Res., 42:470-6 (1999).

Zervoudaki, et al., "Plasma levels of active extracellular matrix metalloproteinases 2 and 9 in patients with essential hypertension before and after antihypertensive treatment", J Hum Hypertens., 17:119-24 (2003).

Zhong, et al., "Changes in metalloproteinase and tissue inhibitor of metalloproteinase during tachycardia-induced cardiomyopathy by rapid atrial pacing in dogs", Cardiology, 106:22-8 (2006).

Zile and Brutsaert, "New concepts in diastolic dysfunction and diastolic heart failure. Part. II: Causal mechanisms and treatment", Circ., 105:1503-8 (2002a).

Zile and Brutsaert, "New concepts in diastolic dysfunction and diastolic heart failure. Part I: Diagnosis, prognosis, measurements of diastolic function", Circ.,105:1387-93 (2002b).

* cited by examiner

Preoperative plasma MMP-9 levels.

Plasma and myocardial levels of MMP-2 and MMP-9.

PREDICTING ATRIAL FIBRILLATION RECURRENCE BY PROTEASE AND PROTEASE INHIBITOR PROFILING

CROSS REFERENCE TO RELATED APPLICATIONS

This application claims the benefit of U.S. Provisional Application No. 60/883,459, filed Jan. 4, 2007, which is hereby incorporated by reference in its entirety.

STATEMENT REGARDING FEDERALLY SPONSORED RESEARCH

This invention was made with government support under Grants HL048788, HL059165, and HL066029 awarded by The National Heart, Lung, and Blood Institute of the National Institutes of Health. The government has certain rights in the invention.

BACKGROUND

Atrial fibrillation (AF) is a disturbance in the rhythmic beating (or arrhythmia) of the upper chambers of the heart. AF is the most common sustained cardiac arrhythmia, responsible for almost 50% of hospitalizations for arrhythmias (Benjamin E J, et al. 1998; Wyse D G, et al. 2002; Benjamin E J, et al. 1997; Allessie M A, et al. 2001). Consequently, AF is a significant cause of morbidity and mortality. Treatment of AF has been hampered by ineffectiveness of drugs. Moreover, attempts to terminate AF with electrical shocks, using a process termed "cardioversion" works for only about one-half of the patients during the first 6-12 months. Consequently, a "simple" means to identify patients in whom cardioversion would effectively terminate AF would be beneficial in terms of saved time and money.

BRIEF SUMMARY

In accordance with the purpose of this invention, as embodied and broadly described herein, this invention relates the use of and systems for the use of MMP, TIMP and/or MMP/TIMP profiles to predict the recurrence of atrial fibrillation following cardioversion.

Additional advantages of the disclosed methods, systems, and compositions will be set forth in part in the description which follows, and in part will be understood from the description, or may be learned by practice of the disclosed methods, systems, and compositions. The advantages of the disclosed methods, systems, and compositions will be realized and attained by means of the elements and combinations particularly pointed out in the appended claims. It is to be understood that both the foregoing general description and the following detailed description are exemplary and explanatory only and are not restrictive of the invention as claimed.

BRIEF DESCRIPTION OF THE DRAWINGS

The accompanying drawings, which are incorporated in and constitute a part of this specification, illustrate several embodiments of the disclosed methods, systems, and compositions and together with the description, serve to explain the principles of the disclosed method and compositions.

FIG. 1 shows a positive relation between left atrial (LA) collagen content and the duration of documented AF ($y=0.300+0.004x$, $r=0.49$, $p=0.023$, SEE 0.148).

FIG. 2 shows pre-cardioversion plasma MMP-9 levels in AF patients dichotomized on the basis of AF recurrence. *$p<0.05$ vs. no AF recurrence group.

FIG. 3 shows determination of AF treatment modality in a first scenario where a patient presents with AF.

FIG. 3 is a block flow diagram of an exemplary method showing outcome outcome prediction after AF cardioversion in a second scenario.

FIG. 4 is a block flow diagram of an exemplary method showing outcome determination of AF treatment modality in a third scenario where a patient presents with recurrent AF.

FIG. 5 is a block flow diagram of an exemplary method showing outcome prediction after AF ablation in a fourth scenario.

FIG. 6 shows a block flow diagram of an exemplary method of predicting the effectiveness of pulmonary vein (PV) ostial ablation for preventing recurrence of atrial fibrillation (AF), comprising measuring MMP and TIMP profiles in a body fluid from the subject and comparing the results to reference values.

FIG. 7 shows preoperative plasma MMP-9 levels from patients undergoing elective open heart surgical procedures.

FIG. 8 shows plasma and myocardial levels of MMP-2 and MMP-9 from patients undergoing elective open heart surgical procedures.

DETAILED DESCRIPTION

The disclosed method and compositions may be understood more readily by reference to the following detailed description of particular embodiments and the Example included therein and to the Figures and their previous and following description.

Disclosed are materials, compositions, and components that can be used for, can be used in conjunction with, can be used in preparation for, or are products of the disclosed methods, systems, and compositions. These and other materials are disclosed herein, and it is understood that when combinations, subsets, interactions, groups, etc. of these materials are disclosed that while specific reference of each various individual and collective combinations and permutation of these compounds, methods and systems may not be explicitly disclosed, each is specifically contemplated and described herein. For example, if a peptide is disclosed and discussed and a number of modifications that can be made to a number of molecules including the peptide are discussed, each and every combination and permutation of peptide and the modifications that are possible are specifically contemplated unless specifically indicated to the contrary. Thus, if a class of molecules A, B, and C are disclosed as well as a class of molecules D, E, and F and an example of a combination molecule, A-D is disclosed, then even if each is not individually recited, each is individually and collectively contemplated. Thus, is this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

Those skilled in the art will recognize, or be able to ascertain using no more than routine experimentation, many equivalents to the specific embodiments of the method and compositions described herein. Such equivalents are intended to be encompassed by the following claims.

It is understood that the disclosed method and compositions are not limited to the particular methodology, protocols, and reagents described as these may vary. It is also to be understood that the terminology used herein is for the purpose of describing particular embodiments only, and is not intended to limit the scope of the present invention which will be limited only by the appended claims.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification. More specifically, the MMPs and TIMPs whose amounts are measured can have those measurements taken in any order.

A. DEFINITIONS

Unless defined otherwise, all technical and scientific terms used herein have the same meanings as commonly understood by one of skill in the art to which the disclosed methods, systems, and compositions belong. Although any methods and materials similar or equivalent to those described herein can be used in the practice or testing of the present method and compositions, the particularly useful methods, systems, devices, and materials are as described. Publications cited herein and the material for which they are cited are hereby specifically incorporated by reference. Nothing herein is to be construed as an admission that the present invention is not entitled to antedate such disclosure by virtue of prior invention. No admission is made that any reference constitutes prior art. The discussion of references states what their authors assert, and applicants reserve the right to challenge the accuracy and pertinency of the cited documents.

It must be noted that as used herein and in the appended claims, the singular forms "a," "an," and "the" include plural reference unless the context clearly dictates otherwise. Thus, for example, reference to "an MMP" or "an TIMP" includes a plurality of such MMPs or TIMPs, reference to "the MMP" or "TIMP" is a reference to one or more MMP or TIMP and equivalents thereof known to those skilled in the art, and so forth.

"Optional" or "optionally" means that the subsequently described event, circumstance, or material may or may not occur or be present, and that the description includes instances where the event, circumstance, or material occurs or is present and instances where it does not occur or is not present.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Throughout the description and claims of this specification, the word "comprise" and variations of the word, such as "comprising" and "comprises," means "including but not limited to," and is not intended to exclude, for example, other additives, components, integers or steps.

"Subject" includes, but is not limited to, animals, plants, bacteria, viruses, parasites and any other organism or entity that has nucleic acid. The subject may be a vertebrate, more specifically a mammal (e.g., a human, horse, pig, rabbit, dog, sheep, goat, non-human primate, cow, cat, guinea pig or rodent), a fish, a bird or a reptile or an amphibian. The subject may be an invertebrate, more specifically an arthropod (e.g., insects and crustaceans). The term does not denote a particular age or sex. Thus, adult and newborn subjects, as well as fetuses, whether male or female, are intended to be covered. A patient refers to a subject afflicted with a disease or disorder. The term "patient" includes human and veterinary subjects.

As defined herein "sample" refers to any sample obtained from an organism. Examples of biological samples include body fluids and tissue specimens. The source of the sample may be physiological media as blood, serum, plasma, breast milk, pus, tissue scrapings, washings, urine, tissue, such as heart tissue or the like.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

B. METHODS

Disclosed herein are methods and systems for the use of MMPs and TIMPs levels as a clinical tool to differentiate between AF patients in whom electrical cardioversion will be successful long-term. For example, plasma levels of MMPs and TIMPs can be used as a clinical tool to differentiate between AF patients in whom electrical cardioversion will be successful long-term or to direct selection of an alternate treatment such as pharmacological rate management, ablation and implantable rate device rather than electrical cardioversion. Thus, also disclosed are methods to direct the clinical management strategy of AF patients between rate control (pharmacological) or rhythm control (device-based and/or pharmacological) treatments. Also disclosed is a method to predict the extent and complexity of ablation procedure needed as a curative approach for AF.

1. Atrial Fibrillation

Atrial fibrillation (AF) is an abnormal heart rhythm (cardiac arrhythmia) which involves the two small, upper heart chambers (the atria). Heart beats in a normal heart begin after electricity generated in the atria by the sinoatrial node spreads through the heart and causes contraction of the heart muscle and pumping of blood. In AF, the regular electrical impulses of the sinoatrial node are replaced by disorganized, rapid electrical impulses which result in irregular heart beats.

Atrial fibrillation is the most common cardiac arrhythmia. An individual may spontaneously alternate between AF and a normal rhythm (paroxysmal atrial fibrillation) or may continue with AF as the dominant cardiac rhythm without reversion to the normal rhythm (chronic atrial fibrillation). Atrial fibrillation is often asymptomatic, but may result in symptoms of palpitations, fainting, chest pain, or even heart failure. These symptoms are especially common when atrial fibrillation results in a heart rate which is either too fast or too slow. In addition, the erratic motion of the atria leads to blood stagnation (stasis) which increases the risk of blood clots that may travel from the heart to the brain and other areas. Thus, AF is an important risk factor for stroke, the most feared complication of atrial fibrillation.

The symptoms of atrial fibrillation may be treated with medications which slow the heart rate. Several medications as well as electrical cardioversion may be used to convert AF to a normal heart rhythm. Surgical and catheter-based therapies may also be used to prevent atrial fibrillation in certain individuals. People with AF are often given blood thinners such as warfarin to protect them from strokes.

The American Heart Association, American College of Cardiology, and the European Society of Cardiology have proposed the following classification system based on simplicity and clinical relevance. "First Detected" refers to any patient newly diagnosed with atrial fibrillation, as the exact onset and chronicity of the disease is often uncertain. A patient with 2 or more identified episodes of atrial fibrillation is said to have "recurrent" atrial fibrillation. This is further classified into "paroxysmal" and "persistent" based on when the episode terminates without therapy. Atrial fibrillation is said to be "paroxysmal" when it terminates spontaneously within 7 days, most commonly within 24 hours. "Persistent" or "chronic" atrial fibrillation is AF established for more than seven days. Differentiation of paroxysmal from chronic or established AF is based on the history of recurrent episodes and the duration of the current episode of AF. "Lone atrial fibrillation" (LAF) is defined as atrial fibrillation in the absence of clinical or echocardiographic findings of cardiopulmonary disease. Patients with LAF who are under 65 have the best prognosis.

Atrial fibrillation is usually accompanied by symptoms related to either rapid heart rate or embolization. Rapid and irregular heart rates may be perceived as palpitations, exercise intolerance, and occasionally produce angina and congestive symptoms of shortness of breath or edema. Sometimes the arrhythmia will be identified with the onset of a stroke or a transient ischemic attack (TIA). It is not uncommon to identify atrial fibrillation on a routine physical examination or electrocardiogram (ECG/EKG), as it may be asymptomatic in some cases.

Paroxysmal atrial fibrillation is the episodic occurrence of the arrhythmia and may be difficult to diagnose. Episodes may occur with sleep or with exercise, and their episodic nature may require prolonged ECG monitoring (e.g. a Holter monitor) for diagnosis.

Atrial fibrillation is diagnosed on an electrocardiogram, an investigation performed routinely whenever irregular heart beat is suspected. Characteristic findings include absence of P waves, unorganized electrical activity in their place, and irregularity of R-R interval due to irregular conduction of impulses to the ventricles.

If paroxysmal AF is suspected, episodes may be documented with the use of Holter monitoring (continuous ECG recording for 24 hours or longer).

While many cases of AF have no definite cause, it may be the result of various other problems. Hence, renal function and electrolytes are routinely determined, as well as thyroid-stimulating hormone (commonly suppressed in hyperthyroidism and of relevance if amiodarone is administered for treatment) and a blood count. A chest X-ray is generally performed. In acute-onset AF associated with chest pain, cardiac troponins or other markers of damage to the heart muscle may be ordered. Coagulation studies (INR/aPTT) are usually performed, as anticoagulant medication may be commenced. A transesophageal echocardiogram may be indicated to identify any intracardiac thrombus.

AF is linked to several cardiac causes, but may occur in otherwise normal hearts. Known associations include carbon monoxide poisoning, high blood pressure, mitral stenosis (e.g. due to rheumatic heart disease or mitral valve prolapse), mitral regurgitation, heart surgery, coronary artery disease, hypertrophic cardiomyopathy, excessive alcohol consumption ("binge drinking" or "holiday heart syndrome"), hyperthyroidism, hyperstimulation of the vagus nerve, usually by having large meals ("binge eating"), lung pathology (such as pneumonia, lung cancer, pulmonary embolism, Sarcoidosis), pericarditis, intense emotional turmoil, and congenital heart disease.

The main goals of treatment of atrial fibrillation are to prevent temporary circulatory instability and to prevent stroke. Rate and rhythm control are principally used to achieve the former, while anticoagulation may be required to decrease the risk of the latter.

AF can cause disabling and annoying symptoms. Palpitations, angina, lassitude (weariness), and decreased exercise tolerance are related to rapid heart rate and inefficient cardiac output caused by AF. There are two ways to approach these symptoms: rate control and rhythm control. Rate control treatments seek to reduce the heart rate to normal, usually 60 to 100 beats per minute. Rhythm control seeks to restore the normal heart rhythm, called normal sinus rhythm. Studies suggest that rhythm control is mainly a concern in newly diagnosed AF, while rate control is more important in the chronic phase.

AF with a persistent rapid rate can cause a form of heart failure called tachycardia induced cardiomyopathy. This can significantly increase mortality and morbidity. The early treatment of AF through either rate-control or rhythm-control can prevent this condition and thereby improve mortality and morbidity.

Rate control methods include beta blockers (e.g. metoprolol), cardiac glycosides (e.g. digoxin), and calcium channel blockers (e.g. verapamil). These medications work by slowing the generation of impulses from the atria and the conduction of those impulse from the atria to the ventricles.

In refractory cases where none of the above drugs are sufficient, a variety of other antiarrhythmic drugs, most commonly including quinidine, flecamide, propafenone, disopyramide, sotalol, or amiodarone may be used. Of these, only propafenone, sotalol, and amiodarone (which possess some beta blocking activity) control the ventricular rate; the others may maintain sinus rhythm, but may actually increase the ventricular rate. Many of these drugs are less frequently used today than in the past. All (with the possible exception of amiodarone) increase the risk of ventricular tachycardia, which can be fatal. In symptomatic patients with normal heart function, however, the small increase in risk is usually felt to be acceptable. In the presence of heart failure, the only anti-arrhythmic drugs thought to be safe are amiodarone and dofetilide.

In patients with AF where rate control drugs are ineffective and it is not possible to restore sinus rhythm using cardioversion, non-pharmacological alternatives are available. For example, to control rate it is possible to destroy the bundle of cells connecting the upper and lower chambers of the heart—the atrioventricular node—which regulates heart rate, and to implant a pacemaker instead. A more complex technique involves ablating groups of cells near the pulmonary veins where atrial fibrillation is thought to originate, or creating more extensive lesions in an attempt to prevent atrial fibrillation from establishing itself.

Rhythm control methods include electrical and chemical cardioversion. Electrical cardioversion involves the restoration of normal heart rhythm through the application of a DC (direct current) electrical shock. Chemical cardioversion is performed with drugs, such as amiodarone, propafenone or flecainide. Implantable pacing devices can also be used for rate management of AF patients and can be indicated versus traditional cardioversion.

The anti-arrhythmic medications often used in either pharmacological cardioversion or in the prevention of relapse to AF alter the flux of ions in heart tissue, making them less excitable, setting the stage for spontaneous and durable cardioversion. These medications are often used in concert with electrical cardioversion.

Whichever method of cardioversion is used, approximately 50% of patients relapse within one year, although the continued daily use of oral antiarrhythmic drugs may extend this period. The key risk factor for relapse is duration of AF, although other risk factors that have been identified include the presence of structural heart disease, and increasing age.

Radiofrequency ablation (RFA) uses radiofrequency energy to destroy abnormal electrical pathways in heart tissue. It is used in recurrent AF. The energy emitting probe (electrode) is placed into the heart through a catheter. The practitioner first "maps" an area of the heart to locate the abnormal electrical activity before the responsible tissue is eliminated. Ablation is a newer technique and has shown some promise for cases unresponsive to conventional treatments. New techniques include the use of cryoablation (tissue freezing using a coolant which flows through the catheter), and microwave ablation, where tissue is ablated by the microwave energy "cooking" the adjacent tissue. The abnormal electrophysiology can also be modified in a similar way surgically, and this procedure referred to as the Cox maze procedure, is commonly performed concomitantly with cardiac surgery. More recently, minimally invasive surgical variations on the Cox Maze procedure ("minimaze" procedures) have also been developed.

The Cox maze procedure is an open-heart surgical procedure intended to eliminate atrial fibrillation. "Maze" refers to the series of incisions made in the atria (upper chambers of the heart), which are arranged in a maze-like pattern. The intention was to eliminate AF by using incisional scars to block abnormal electrical circuits (atrial macroreentry) that AF requires. This procedure required an extensive series of endocardial (from the inside of the heart) incisions through both atria, a median sternotomy (vertical incision through the breastbone) and cardiopulmonary bypass (heart-lung machine). A series of improvements were made, culminating in 1992 in the Cox maze III procedure, which is now considered to be the "gold standard" for effective surgical cure of AF. The Cox maze III is sometimes referred to as the "traditional maze", the "cut and sew maze", or simply the "maze".

Minimaze surgery is minimally invasive cardiac surgery intended to cure atrial fibrillation. Minimaze refers to "mini" versions of the original maze procedure. These procedures are less invasive than the Cox maze procedure and do not require a median sternotomy (vertical incision in the breastbone) or cardiopulmonary bypass (heart-lung machine). These procedures use microwave, radiofrequency, or acoustic energy to ablate atrial tissue near the pulmonary veins.

In confirmed AF, anticoagulant treatment is a crucial way to prevent stroke. Treatment of AF patients over age 60, who also have one or more of: previous strokes (or warning strokes), hypertension (high blood pressure), diabetes, or congestive heart failure, with warfarin (also known as Coumadin® or Marevan®) results in a 60 to 70 percent reduction in the subsequent risk of stroke. Patients under age 65 who have any structural heart disease (i.e. valvular heart disease, ejection fraction <=35%, history of heart attack) may also benefit from warfarin.

The use of warfarin is associated with a delayed clinical effect. It typically takes three to five days to achieve a demonstrable anticoagulant effect. Hence, if an immediate anticoagulant effect is required, physicians could use heparin or other heparinoids such as enoxaparin to provide early anticoagulation. In practice, urgent anticoagulation is seldom indicated. Even in the setting of stroke complicating atrial fibrillation, clinical trial results do not support the routine use of immediate anticoagulation.

Patients under age 65 who do not have structural heart disease (i.e. with LAF) do not require warfarin, and can be treated with aspirin or clopidogrel. There is evidence that aspirin and clopidogrel are effective when used together. The new anticoagulant ximelagatran has been shown to prevent stroke with equal efficacy as warfarin.

Determining who should and should not receive anti-coagulation with anti-coagulant drugs (e.g., warfarin, ximegalatran, heparin or other heparinoids) is not easy. The CHADS2 score is the best validated method of determining risk of stroke (and therefore who should be anticoagulated). The UK NICE guidelines have instead opted for an algorithm approach. The underlying problem is that if a patient has a yearly risk of stroke that is less than 2%, then the risks associated with taking warfarin outweigh the risk of getting a stroke.

2. MMPs

Key contributors to ECM synthesis/degradation are the matrix metalloproteinases (MMPs) and the endogenous tissue inhibitors of the metalloproteinases (TIMPs) (Visse R, et al. 2003; Matrisian L M, et al. 1990).

Matrix metalloproteinases (MMPs) are zinc-dependent endopeptidases; other family members are adamalysins, serralysins, and astacins. The MMPs belong to a larger family of proteases known as the metzincin superfamily.

The MMPs share a common domain structure. The three common domains are the pro-peptide, the catalytic domain and the haemopexin-like C-terminal domain which is linked to the catalytic domain by a flexible hinge region.

The MMPs are initially synthesised as inactive zymogens with a pro-peptide domain that must be removed before the enzyme is active. The pro-peptide domain is part of "cysteine switch" this contains a conserved cysteine residue which interacts with the zinc in the active site and prevents binding and cleavage of the substrate keeping the enzyme in an inactive form. In the majority of the MMPs, the cysteine residue is in the conserved sequence PRCGxPD. Some MMPs have a prohormone convertase cleavage site (Furin-like) as part of this domain which when cleaved activates the enzyme. MMP-23A and MMP-23B include a transmembrane segment in this domain (PMID 10945999).

X-ray crystallographic structures of several MMP catalytic domains have shown that this domain is an oblate sphere measuring 35×30×30 Å (3.5×3×3 nm). The active site is a 20 Å (2 nm) groove that runs across the catalytic domain. In the part of the catalytic domain forming the active site there is a catalytically important $Zn^{2+}$ ion, which is bound by three histidine residues found in the conserved sequence HExxHxxGxxH. Hence, this sequence is a zinc-binding motif.

The gelatinases, such as MMP-2, incorporate Fibronectin type II modules inserted immediately before in the zinc-binding motif in the catalytic domain (PMID 12486137).

The catalytic domain is connected to the C-terminal domain by a flexible hinge or linker region. This is up to 75 amino acids long, and has no determinable structure.

The C-terminal domain has structural similarities to the serum protein haemopexin. It has a four bladed β-propeller structure. β-propeller structures provide a large flat surface which is thought to be involved in protein-protein interactions. This determines substrate specificity and is the site for interaction with TIMP's. The haemopexin-like domain is absent in MMP-7, MMP-23, MMP-26 and the plant and nematode. MT-MMPs are anchored to the plasma membrane, through this domain and some of these have cytoplasmic domains.

The MMPs can be subdivided in different ways. Use of bioinformatic methods to compare the primary sequences of the MMPs suggests the following evolutionary groupings of the MMPs: MMP-19; MMPs 11, 14, 15, 16 and 17; MMP-2 and MMP-9; all the other MMPs.

Analysis of the catalytic domains in isolation suggests that the catalytic domains evolved further once the major groups had differentiated, as is also indicated by the substrate specificities of the enzymes. The most commonly used groupings (by researchers in MMP biology) are based partly on historical assessment of the substrate specificity of the MMP and partly on the cellular localisation of the MMP. These groups are the collagenases, the gelatinases, the stromelysins, and the membrane type MMPs (MT-MMPs). It is becoming increasingly clear that these divisions are somewhat artificial as there are a number of MMPs that do not fit into any of the traditional groups.

The collagneases are capable of degrading triple-helical fibrillar collagens into distinctive ¾ and ¼ fragments. These collagens are the major components of bone and cartilage, and MMPs are the only known mammalian enzymes capable of degrading them. Traditionally, the collagenases are: MMP-1 (Interstitial collagenase), MMP-8 (Neutrophil collagenase), MMP-13 (Collagenase 3), MMP-18 (Collagenase 4, xco14, xenopus collagenase. No known human orthologue), MMP-14 (MT1-MMP) has also been shown to cleave fibrillar collagen, and more controversially there is evidence that MMP-2 is capable of collagenolysis.

The stromelysins display a broad ability to cleave extracellular matrix proteins but are unable to cleave the triple-helical fibrillar collagens. The three canonical members of this group are: MMP-3 (Stromelysin 1), MMP-10 (Stromelysin 2), and MMP-11 (Stromelysin 3). MMP-11 shows more similarity to the MT-MMPs, is convertase-activatable and is secreted therefore usually associated to convertase-activatable MMPs.

The matrilysins include MMP-7 (Matrilysin, PUMP) and MMP-26 (Matrilysin-2, endometase).

The main substrates of gelatinasese are type IV collagen and gelatin, and these enzymes are distinguished by the presence of an additional domain inserted into the catalytic domain. This gelatin-binding region is positioned immediately before the zinc binding motif, and forms a separate folding unit which does not disrupt the structure of the catalytic domain. The two members of this sub-group are: MMP-2 (72 kDa gelatinase, gelatinase-A) and MMP-9 (92 kDa gelatinase, gelatinase-B).

The secreted MMPs include MMP-11 (Stromelysin 3), MMP-21 (X-MMP), and MMP-28 (Epilysin).

The membrane-bound MMPs include: the type-II transmembrane cysteine array MMP-23, the glycosyl phosphatidylinositol-attached MMPs 17 and 25 (MT4-MMP and MT6-MMP respectively), and the type-I transmembrane MMPs 14, 15, 16, 24 (MT1-MMP, MT2-MMP, MT3-MMP, and MT5-MMP respectively).

All 6 MT-MMPs have a furin cleavage site in the pro-peptide, which is a feature also shared by MMP-11.

Other MMPs include MMP-12 (Macrophage metalloelastase), MMP-19 (RASI-1, occasionally referred to as stromelysin-4), Enamelysin (MMP-20), and MMP-27 (MMP-22, C-MMP), MMP-23A (CA-MMP), and MMP-23B.

3. TIMPs

The MMPs are inhibited by specific endogenous tissue inhibitor of metalloproteinases (TIMPs), which comprise a family of four protease inhibitors: TIMP-1, TIMP-2, TIMP-3 and TIMP-4. Overall, all MMPs are inhibited by TIMPs once they are activated but the gelatinases (MMP-2 and MMP-9) can form complexes with TIMPs when the enzymes are in the latent form. The complex of latent MMP-2 (pro-MMP-2) with TIMP-2 serves to facilitate the activation of pro-MMP-2 at the cell surface by MT1-MMP (MMP-14), a membrane-anchored MMP.

4. MMP/TIMP Ratio

One of the unique characteristics for MMP-TIMP profiling in predicting clinical outcomes of patients treated for atrial fibrillation is to utilize the cardiac specific TIMP, TIMP-4, and place this in context with an MMP which changes in greater magnitude in AF. Also disclosed are ratios of an MMP, such as MMP-9 or MMP-13, to a TIMP, such as TIMP-1, TIMP-2, or TIMP-4. These ratios are used for the first time herein as diagnostic differentials and for identifying patients with distinctly different disease states.

5. MMP/TIMP Screening

A key advantage of the present teaching is that the herein disclosed methods afford a more rapid and simplified process to identify from a tissue or bodily fluid or tissue of a subject at risk for recurrence of atrial fibrillation following cardioversion, for example traditional electrical cardioversion. Thus, the herein disclosed methods can comprise the detection of MMPs and TIMPs in bodily fluid of the subject, such as blood, urine, plasma, serum, tears, lymph, bile, cerebrospinal fluid, interstitial fluid, aqueous or vitreous humor, colostrum, sputum, amniotic fluid, saliva, anal and vaginal secretions, perspiration, semen, transudate, exudate, and synovial fluid.

Blood plasma is the liquid component of blood, in which the blood cells are suspended. Plasma is the largest single component of blood, making up about 55% of total blood volume. Serum refers to blood plasma in which clotting factors (such as fibrin) have been removed. Blood plasma contains many vital proteins including fibrinogen, globulins and human serum albumin. Sometimes blood plasma can contain viral impurities which must be extracted through viral processing.

6. MMP/TIMP Detection Assays

There are numerous methods, known or newly discovered in the art, which can be used in the disclosed methods for detecting analytes, such as proteins, such as MMPs and TIMPs. Moreover, the disclosed systems can utilize means known in the art to detect analytes, such as proteins, such as MMPs and TIMPs.

For example, MMPs and TIMPs can be detected using standard immunodetection methods. The steps of various useful immunodetection methods have been described in the scientific literature, such as, e.g., Maggio et al., Enzyme-Immunoassay, (1987) and Nakamura, et al., Enzyme Immunoassays: Heterogeneous and Homogeneous Systems, Handbook of Experimental Immunology, Vol. 1: Immunochemistry, 27.1-27.20 (1986), each of which is incorporated herein by reference in its entirety and specifically for its teaching regarding immunodetection methods. Immunoassays, in their most simple and direct sense, are binding assays involving binding between antibodies and antigen. Many types and formats of immunoassays are known and all are suitable for detecting the disclosed biomarkers. Examples of immunoassays are enzyme linked immunosorbent assays (ELISAs), radioimmunoassays (RIA), radioimmune precipitation assays (RIPA), immunobead capture assays, Western blotting, dot blotting, gel-shift assays, Flow cytometry, protein arrays, multiplexed bead arrays, magnetic capture, in vivo imaging, fluorescence resonance energy transfer (FRET), and fluorescence recovery/localization after photobleaching (FRAP/FLAP).

In general, immunoassays involve contacting a sample suspected of containing a molecule of interest (such as the disclosed biomarkers) with an antibody to the molecule of interest or contacting an antibody to a molecule of interest (such as antibodies to the disclosed biomarkers) with a molecule that can be bound by the antibody, as the case may be, under conditions effective to allow the formation of immunocomplexes. Contacting a sample with the antibody to the molecule of interest or with the molecule that can be bound by an antibody to the molecule of interest under conditions effective and for a period of time sufficient to allow the formation of immune complexes (primary immune complexes) is generally a matter of simply bringing into contact the molecule or antibody and the sample and incubating the mixture for a period of time long enough for the antibodies to form immune complexes with, i.e., to bind to, any molecules (e.g., antigens) present to which the antibodies can bind. In many forms of immunoassay, the sample-antibody composition, such as a tissue section, ELISA plate, dot blot or Western blot, can then be washed to remove any non-specifically bound antibody species, allowing only those antibodies specifically bound within the primary immune complexes to be detected.

Immunoassays can include methods for detecting or quantifying the amount of a molecule of interest (such as the disclosed biomarkers or their antibodies) in a sample, which methods generally involve the detection or quantitation of any immune complexes formed during the binding process. In general, the detection of immunocomplex formation is well known in the art and can be achieved through the application of numerous approaches. These methods are generally based upon the detection of a label or marker, such as any radioactive, fluorescent, biological or enzymatic tags or any other known label. See, for example, U.S. Pat. Nos. 3,817,837; 3,850,752; 3,939,350; 3,996,345; 4,277,437; 4,275,149 and 4,366,241, each of which is incorporated herein by reference in its entirety and specifically for teachings regarding immunodetection methods and labels.

As used herein, a label can include a fluorescent dye, a member of a binding pair, such as biotin/streptavidin, a metal (e.g., gold), or an epitope tag that can specifically interact with a molecule that can be detected, such as by producing a colored substrate or fluorescence. Substances suitable for detectably labeling proteins include fluorescent dyes (also known herein as fluorochromes and fluorophores) and enzymes that react with colorometric substrates (e.g., horseradish peroxidase). The use of fluorescent dyes is generally preferred in the practice of the invention as they can be detected at very low amounts. Furthermore, in the case where multiple antigens are reacted with a single array, each antigen can be labeled with a distinct fluorescent compound for simultaneous detection. Labeled spots on the array are detected using a fluorimeter, the presence of a signal indicating an antigen bound to a specific antibody.

Fluorophores are compounds or molecules that luminesce. Typically fluorophores absorb electromagnetic energy at one wavelength and emit electromagnetic energy at a second wavelength. Representative fluorophores include, but are not limited to, 1,5 IAEDANS; 1,8-ANS; 4-Methylumbelliferone; 5-carboxy-2,7-dichlorofluorescein; 5-Carboxyfluorescein (5-FAM); 5-Carboxynapthofluorescein; 5-Carboxytetramethylrhodamine (5-TAMRA); 5-Hydroxy Tryptamine (5-HAT); 5-ROX (carboxy-X-rhodamine); 6-Carboxyrhodamine 6G; 6-CR 6G; 6-JOE; 7-Amino-4-methylcoumarin; 7-Aminoactinomycin D (7-AAD); 7-Hydroxy-4-I methylcoumarin; 9-Amino-6-chloro-2-methoxyacridine (ACMA); ABQ; Acid Fuchsin; Acridine Orange; Acridine Red; Acridine Yellow; Acriflavin; Acriflavin Feulgen SITSA; Aequorin (Photoprotein); AFPs—AutoFluorescent Protein—(Quantum Biotechnologies) see sgGFP, sgBFP; Alexa Fluor 350™; Alexa Fluor 430™; Alexa Fluor 488™; Alexa Fluor 532™; Alexa Fluor 546™; Alexa Fluor 568™; Alexa Fluor 594™; Alexa Fluor 633™; Alexa Fluor 647™; Alexa Fluor 660™; Alexa Fluor 680™; Alizarin Complexon; Alizarin Red; Allophycocyanin (APC); AMC, AMCA-S; Aminomethylcoumarin (AMCA); AMCA-X; Aminoactinomycin D; Aminocoumarin; Anilin Blue; Anthrocyl stearate; APC-Cy7; APTRA-BTC; APTS; Astrazon Brilliant Red 4G; Astrazon Orange R; Astrazon Red 6B; Astrazon Yellow 7 GLL; Atabrine; ATTO-TAG™ CBQCA; ATTO-TAG™ FQ; Auramine; Aurophosphine G; Aurophosphine; BAO 9 (Bisaminophenyloxadiazole); BCECF (high pH); BCECF (low pH); Berberine Sulphate; Beta Lactamase; BFP blue shifted GFP (Y66H); Blue Fluorescent Protein; BFP/GFP FRET; Bimane; Bisbenzemide; Bisbenzimide (Hoechst); bis-BTC; Blancophor FFG; Blancophor SV; BOBO™-1; BOBO™-3; Bodipy 492/515; Bodipy 493/503; Bodipy 500/510; Bodipy; 505/515; Bodipy 530/550; Bodipy 542/563; Bodipy 558/568; Bodipy 564/570; Bodipy 576/589; Bodipy 581/591; Bodipy 630/650-X; Bodipy 650/665-X; Bodipy 665/676; Bodipy Fl; Bodipy FL ATP; Bodipy Fl-Ceramide; Bodipy R6G SE; Bodipy TMR; Bodipy TMR-X conjugate; Bodipy TMR-X, SE; Bodipy TR; Bodipy TR ATP; Bodipy TR-X SE; BO-PRO™-1; BO-PRO™-3; Brilliant Sulphoflavin FF; BTC; BTC-5N; Calcein; Calcein Blue; Calcium Crimson-; Calcium Green; Calcium Green-1 $Ca^{2+}$ Dye; Calcium Green-2 $Ca^{2+}$; Calcium Green-5N $Ca^{2+}$; Calcium Green-C18 $Ca^{2+}$; Calcium Orange; Calcofluor White; Carboxy-X-rhodamine (5-ROX); Cascade Blue™; Cascade Yellow; Catecholamine; CCF2 (GeneBlazer); CFDA; CFP (Cyan Fluorescent Protein); CFP/YFP FRET; Chlorophyll; Chromomycin A; Chromomycin A; CL-NERF; CMFDA; Coelenterazine; Coelenterazine cp; Coelenterazine f; Coelenterazine fcp; Coelenterazine h; Coelenterazine hcp; Coelenterazine ip; Coelenterazine n; Coelenterazine O; Coumarin Phalloidin; C-phycocyanine; CPM I Methylcoumarin; CTC; CTC Formazan; Cy2™; Cy3.1 8; Cy3.5™; Cy3™; Cy5.1 8; Cy5.5™; Cy5™; Cy7™; Cyan GFP; cyclic AMP Fluorosensor (FiCRhR); Dabcyl; Dansyl; Dansyl Amine; Dansyl Cadaverine; Dansyl Chloride; Dansyl DHPE; Dansyl fluoride; DAPI; Dapoxyl; Dapoxyl 2; Dapoxyl 3'DCFDA; DCFH (Dichlorodihydrofluorescein Diacetate); DDAO; DHR (Dihydrorhodamine 123); Di-4-ANEPPS; Di-8-ANEPPS (non-ratio); DiA (4-Di 16-ASP); Dichlorodihydrofluorescein Diacetate (DCFH); DiD-Lipophilic Tracer; DiD (DilC18(5)); DIDS; Dihydrorhodamine 123 (DHR); DiI (DilC18(3)); I Dinitrophenol; DiO (DiOC18(3)); DiR; DiR (DilC18(7)); DM-NERF (high pH); DNP; Dopamine; DsRed; DTAF; DY-630-NHS; DY-635-NHS; EBFP; ECFP; EGFP; ELF 97; Eosin; Erythrosin; Erythrosin ITC; Ethidium Bromide; Ethidium homodimer-1 (EthD-1); Euchrysin; EukoLight; Europium (111) chloride; EYFP; Fast Blue; FDA; Feulgen (Pararosaniline); FIF (Formaldehyd Induced Fluorescence); FITC; Flazo Orange; Fluo-3; Fluo-4; Fluorescein (FITC); Fluorescein Diacetate; Fluoro-Emerald; Fluoro-Gold (Hydroxystilbamidine); Fluor-Ruby; Fluor X; FM 1-43™; FM 4-46; Fura Red™ (high pH); Fura Red™/Fluo-3; Fura-2; Fura-2/BCECF; Genacryl Brilliant Red B; Genacryl Brilliant Yellow 10GF; Genacryl Pink 3G; Genacryl Yellow 5GF; GeneBlazer; (CCF2); GFP (S65T); GFP red shifted (rsGFP); GFP wild type' non-UV excitation (wtGFP); GFP wild type, UV excitation (wtGFP); GFPuv; Gloxalic Acid; Granular blue; Haematoporphyrin; Hoechst 33258; Hoechst 33342; Hoechst 34580; HPTS; Hydroxycoumarin; Hydroxystilbamidine (FluoroGold); Hydroxytryptamine; Indo-1, high calcium; Indo-1 low calcium; Indodicarbocyanine (DiD); Indotricarbocyanine (DiR); Intrawhite Cf; JC-1; JO JO-1; JO-PRO-1; LaserPro; Laurodan; LDS 751 (DNA); LDS 751 (RNA); Leucophor PAF; Leucophor SF; Leucophor WS; Lissamine Rhodamine; Lissamine Rhodamine B; Calcein/Ethidium homodimer; LOLO-1; LO-PRO-1; Lucifer Yellow; Lyso Tracker Blue; Lyso Tracker Blue-White; Lyso Tracker Green; Lyso Tracker Red; Lyso Tracker Yellow; LysoSensor Blue; LysoSensor Green; LysoSensor Yellow/Blue; Mag Green; Magdala Red (Phloxin B); Mag-Fura Red; Mag-Fura-2; Mag-Fura-5; Mag-Indo-1; Magnesium Green; Magnesium Orange; Malachite Green; Marina Blue; I Maxilon Brilliant Flavin 10 GFF; Maxilon Brilliant Flavin 8 GFF; Merocyanin; Methoxycoumarin; Mitotracker Green FM; Mitotracker Orange; Mitotracker Red; Mitramycin; Monobromobimane; Monobromobimane (mBBr-GSH); Monochlorobimane; MPS (Methyl Green Pyronine Stilbene); NBD; NBD Amine; Nile Red; Nitrobenzoxedidole; Noradrenaline; Nuclear Fast Red; i Nuclear Yellow; Nylosan Brilliant lavin E8G; Oregon Green™; Oregon Green™ 488; Oregon Green™ 500; Oregon Green™ 514; Pacific Blue; Pararosaniline (Feulgen); PBFI; PE-Cy5; PE-Cy7; PerCP; PerCP-Cy5.5; PE-TexasRed (Red 613); Phloxin B (Magdala Red); Phorwite AR; Phorwite BKL; Phorwite Rev; Phorwite RPA; Phosphine 3R; PhotoResist; Phycoerythrin B [PE]; Phycoerythrin R [PE]; PKH26 (Sigma); PKH67; PMIA; Pontochrome Blue Black; POPO-1; POPO-3; PO-PRO-1; PO-I PRO-3; Primuline; Procion Yellow; Propidium lodid (PI); PyMPO; Pyrene; Pyronine; Pyronine B; Pyrozal Brilliant Flavin 7GF; QSY 7; Quinacrine Mustard; Resorufin; RH 414; Rhod-2; Rhodamine; Rhodamine 110; Rhodamine 123; Rhodamine 5 GLD; Rhodamine 6G; Rhodamine B; Rhodamine B 200; Rhodamine B extra; Rhodamine BB; Rhodamine BG; Rhodamine Green; Rhodamine Phallicidine; Rhodamine: Phalloidine; Rhodamine Red; Rhodamine WT; Rose Bengal; R-phycocyanine; R-phycoerythrin (PE); rsGFP; S65A; S65C; S65L; S65T; Sapphire GFP; SBFI; Serotonin; Sevron Brilliant Red 2B; Sevron Brilliant Red 4G; Sevron I Brilliant Red B; Sevron Orange; Sevron Yellow L; sgBFP™ (super glow BFP); sgGFP™ (super glow GFP); SITS (Primuline; Stilbene Isothiosulphonic Acid); SNAFL calcein; SNAFL-1; SNAFL-2; SNARF calcein; SNARF1; Sodium Green; SpectrumAqua; SpectrumGreen; SpectrumOrange; Spectrum Red; SPQ (6-methoxy-N-(3 sulfopropyl) quinolinium); Stilbene; Sulphorhodamine B and C; Sulphorhodamine Extra; SYTO 11; SYTO 12; SYTO 13; SYTO 14; SYTO 15; SYTO 16; SYTO 17; SYTO 18; SYTO 20; SYTO 21; SYTO 22; SYTO 23; SYTO 24; SYTO 25; SYTO 40; SYTO 41; SYTO 42; SYTO 43; SYTO 44; SYTO 45; SYTO 59; SYTO 60; SYTO 61; SYTO 62; SYTO 63; SYTO 64; SYTO 80; SYTO 81; SYTO 82; SYTO 83; SYTO 84; SYTO 85; SYTOX Blue; SYTOX Green; SYTOX Orange; Tetracycline; Tetramethylrhodamine (TRITC); Texas Red™; Texas Red-X™ conjugate; Thiadicarbocyanine (DiSC3); Thiazine Red R; Thiazole Orange; Thioflavin 5; Thioflavin S; Thioflavin TON; Thiolyte; Thiozole Orange; Tinopol CBS (Calcofluor White); TIER; TO-PRO-1; TO-PRO-3; TO-PRO-5; TOTO-1; TOTO-3; TriColor (PE-Cy5); TRITC TetramethylRodamineIsoThioCyanate; True Blue; Tru Red; Ultralite; Uranine B; Uvitex SFC; wt GFP; WW 781; X-Rhodamine; XRITC; Xylene Orange; Y66F; Y66H; Y66W; Yellow GFP; YFP; YO-PRO-1; YO-PRO 3; YOYO-1; YOYO-3; Sybr Green; Thiazole orange (interchelating dyes); semiconductor nanoparticles such as quantum dots; or caged fluorophore (which can be activated with light or other electromagnetic energy source), or a combination thereof.

Labeling can be either direct or indirect. In direct labeling, the detecting antibody (the antibody for the molecule of interest) or detecting molecule (the molecule that can be bound by an antibody to the molecule of interest) include a label. Detection of the label indicates the presence of the detecting antibody or detecting molecule, which in turn indicates the presence of the molecule of interest or of an antibody to the molecule of interest, respectively. In indirect labeling, an additional molecule or moiety is brought into contact with, or generated at the site of, the immunocomplex. For example, a signal-generating molecule or moiety such as an enzyme can be attached to or associated with the detecting antibody or detecting molecule. The signal-generating molecule can then generate a detectable signal at the site of the immunocomplex. For example, an enzyme, when supplied with suitable substrate, can produce a visible or detectable product at the site of the immunocomplex. ELISAs use this type of indirect labeling.

As another example of indirect labeling, an additional molecule (which can be referred to as a binding agent) that can bind to either the molecule of interest or to the antibody (primary antibody) to the molecule of interest, such as a second antibody to the primary antibody, can be contacted with the immunocomplex. The additional molecule can have a label or signal-generating molecule or moiety. The additional molecule can be an antibody, which can thus be termed a secondary antibody. Binding of a secondary antibody to the primary antibody can form a so-called sandwich with the first (or primary) antibody and the molecule of interest. The immune complexes can be contacted with the labeled, secondary antibody under conditions effective and for a period of time sufficient to allow the formation of secondary immune complexes. The secondary immune complexes can then be generally washed to remove any non-specifically bound labeled secondary antibodies, and the remaining label in the secondary immune complexes can then be detected. The additional molecule can also be or include one of a pair of molecules or moieties that can bind to each other, such as the biotin/avadin pair. In this mode, the detecting antibody or detecting molecule should include the other member of the pair.

Other modes of indirect labeling include the detection of primary immune complexes by a two step approach. For example, a molecule (which can be referred to as a first binding agent), such as an antibody, that has binding affinity for the molecule of interest or corresponding antibody can be used to form secondary immune complexes, as described above. After washing, the secondary immune complexes can be contacted with another molecule (which can be referred to as a second binding agent) that has binding affinity for the first binding agent, again under conditions effective and for a period of time sufficient to allow the formation of immune complexes (thus forming tertiary immune complexes). The second binding agent can be linked to a detectable label or signal-generating molecule or moiety, allowing detection of the tertiary immune complexes thus formed. This system can provide for signal amplification.

Immunoassays that involve the detection of a substance, such as a protein or an antibody to a specific protein, include label-free assays, protein separation methods (i.e., electrophoresis), solid support capture assays, or in vivo detection. Label-free assays are generally diagnostic means of determining the presence or absence of a specific protein, or an antibody to a specific protein, in a sample. Protein separation methods are additionally useful for evaluating physical properties of the protein, such as size or net charge. Capture assays are generally more useful for quantitatively evaluating the concentration of a specific protein, or antibody to a specific protein, in a sample. Finally, in vivo detection is useful for evaluating the spatial expression patterns of the substance, i.e., where the substance can be found in a subject, tissue or cell.

Provided that the concentrations are sufficient, the molecular complexes ([Ab-Ag]n) generated by antibody-antigen interaction are visible to the naked eye, but smaller amounts may also be detected and measured due to their ability to scatter a beam of light. The formation of complexes indicates that both reactants are present, and in immunoprecipitation assays a constant concentration of a reagent antibody is used to measure specific antigen ([Ab-Ag]n), and reagent antigens are used to detect specific antibody ([Ab-Ag]n). If the reagent species is previously coated onto cells (as in hemagglutination assay) or very small particles (as in latex agglutination assay), "clumping" of the coated particles is visible at much lower concentrations. A variety of assays based on these elementary principles are in common use, including Ouchterlony immunodiffusion assay, rocket immunoelectrophoresis, and immunoturbidometric and nephelometric assays. The main limitations of such assays are restricted sensitivity (lower detection limits) in comparison to assays employing labels and, in some cases, the fact that very high concentrations of analyte can actually inhibit complex formation, necessitating safeguards that make the procedures more complex. Some of these Group 1 assays date right back to the discovery of antibodies and none of them have an actual "label" (e.g. Ag-enz). Other kinds of immunoassays that are label free depend on immunosensors, and a variety of instruments that can directly detect antibody-antigen interactions are now commercially available. Most depend on generating an evanescent wave on a sensor surface with immobilized ligand, which allows continuous monitoring of binding to the ligand. Immunosensors allow the easy investigation of kinetic interactions and, with the advent of lower-cost specialized instruments, may in the future find wide application in immunoanalysis.

The use of immunoassays to detect a specific protein can involve the separation of the proteins by electophoresis. Electrophoresis is the migration of charged molecules in solution in response to an electric field. Their rate of migration depends on the strength of the field; on the net charge, size and shape of the molecules and also on the ionic strength, viscosity and temperature of the medium in which the molecules are moving. As an analytical tool, electrophoresis is simple, rapid and highly sensitive. It is used analytically to study the properties of a single charged species, and as a separation technique.

Generally the sample is run in a support matrix such as paper, cellulose acetate, starch gel, agarose or polyacrylamide gel. The matrix inhibits convective mixing caused by heating and provides a record of the electrophoretic run: at the end of the run, the matrix can be stained and used for scanning, autoradiography or storage. In addition, the most commonly used support matrices—agarose and polyacrylamide—provide a means of separating molecules by size, in that they are porous gels. A porous gel may act as a sieve by retarding, or in some cases completely obstructing, the movement of large macromolecules while allowing smaller molecules to migrate freely. Because dilute agarose gels are generally more rigid and easy to handle than polyacrylamide of the same concentration, agarose is used to separate larger macromolecules such as nucleic acids, large proteins and protein complexes. Polyacrylamide, which is easy to handle and to make at higher concentrations, is used to separate most proteins and small oligonucleotides that require a small gel pore size for retardation.

Proteins are amphoteric compounds; their net charge therefore is determined by the pH of the medium in which they are suspended. In a solution with a pH above its isoelectric point, a protein has a net negative charge and migrates towards the anode in an electrical field. Below its isoelectric point, the protein is positively charged and migrates towards the cathode. The net charge carried by a protein is independent of its size—i.e., the charge carried per unit mass (or length, given proteins and nucleic acids are linear macromolecules) of molecule differs from protein to protein. At a given pH therefore, and under non-denaturing conditions, the electrophoretic separation of proteins is determined by both size and charge of the molecules.

Sodium dodecyl sulphate (SDS) is an anionic detergent which denatures proteins by "wrapping around" the polypeptide backbone—and SDS binds to proteins fairly specifically in a mass ratio of 1.4:1. In so doing, SDS confers a negative charge to the polypeptide in proportion to its length. Further, it is usually necessary to reduce disulphide bridges in proteins (denature) before they adopt the random-coil configuration necessary for separation by size; this is done with 2-mercaptoethanol or dithiothreitol (DTT). In denaturing SDS-PAGE separations therefore, migration is determined not by intrinsic electrical charge of the polypeptide, but by molecular weight.

Determination of molecular weight is done by SDS-PAGE of proteins of known molecular weight along with the protein to be characterized. A linear relationship exists between the logarithm of the molecular weight of an SDS-denatured polypeptide, or native nucleic acid, and its Rf. The Rf is calculated as the ratio of the distance migrated by the molecule to that migrated by a marker dye-front. A simple way of determining relative molecular weight by electrophoresis (Mr) is to plot a standard curve of distance migrated vs. log 10 MW for known samples, and read off the log Mr of the sample after measuring distance migrated on the same gel.

In two-dimensional electrophoresis, proteins are fractionated first on the basis of one physical property, and, in a second step, on the basis of another. For example, isoelectric focusing can be used for the first dimension, conveniently carried out in a tube gel, and SDS electrophoresis in a slab gel can be used for the second dimension. One example of a procedure is that of O'Farrell, P. H., High Resolution Two-dimensional Electrophoresis of Proteins, J. Biol. Chem. 250: 4007-4021 (1975), herein incorporated by reference in its entirety for its teaching regarding two-dimensional electrophoresis methods. Other examples include but are not limited to, those found in Anderson, L and Anderson, N G, High resolution two-dimensional electrophoresis of human plasma proteins, Proc. Natl. Acad. Sci. 74:5421-5425 (1977), Ornstein, L., Disc electrophoresis, L. Ann. N.Y. Acad. Sci. 121: 321349 (1964), each of which is herein incorporated by reference in its entirety for teachings regarding electrophoresis methods.

Laemmli, U. K., Cleavage of structural proteins during the assembly of the head of bacteriophage T4, Nature 227:680 (1970), which is herein incorporated by reference in its entirety for teachings regarding electrophoresis methods, discloses a discontinuous system for resolving proteins denatured with SDS. The leading ion in the Laemmli buffer system is chloride, and the trailing ion is glycine. Accordingly, the resolving gel and the stacking gel are made up in Tris-HCl buffers (of different concentration and pH), while the tank buffer is Tris-glycine. All buffers contain 0.1% SDS.

One example of an immunoassay that uses electrophoresis that is contemplated in the current methods is Western blot analysis. Western blotting or immunoblotting allows the determination of the molecular mass of a protein and the measurement of relative amounts of the protein present in different samples. Detection methods include chemiluminescence and chromagenic detection. Standard methods for Western blot analysis can be found in, for example, D. M. Bollag et al., Protein Methods (2d edition 1996) and E. Harlow & D. Lane, Antibodies, a Laboratory Manual (1988), U.S. Pat. No. 4,452,901, each of which is herein incorporated by reference in their entirety for teachings regarding Western blot methods. Generally, proteins are separated by gel electrophoresis, usually SDS-PAGE. The proteins are transferred to a sheet of special blotting paper, e.g., nitrocellulose, though other types of paper, or membranes, can be used. The proteins retain the same pattern of separation they had on the gel. The blot is incubated with a generic protein (such as milk proteins) to bind to any remaining sticky places on the nitrocellulose. An antibody is then added to the solution which is able to bind to its specific protein.

The attachment of specific antibodies to specific immobilized antigens can be readily visualized by indirect enzyme immunoassay techniques, usually using a chromogenic substrate (e.g. alkaline phosphatase or horseradish peroxidase) or chemiluminescent substrates. Other possibilities for probing include the use of fluorescent or radioisotope labels (e.g., fluorescein, $^{125}$I). Probes for the detection of antibody binding can be conjugated anti-immunoglobulins, conjugated staphylococcal Protein A (binds IgG), or probes to biotinylated primary antibodies (e.g., conjugated avidin/streptavidin).

The power of the technique lies in the simultaneous detection of a specific protein by means of its antigenicity, and its molecular mass. Proteins are first separated by mass in the SDS-PAGE, then specifically detected in the immunoassay step. Thus, protein standards (ladders) can be run simultaneously in order to approximate molecular mass of the protein of interest in a heterogeneous sample.

The gel shift assay or electrophoretic mobility shift assay (EMSA) can be used to detect the interactions between DNA binding proteins and their cognate DNA recognition sequences, in both a qualitative and quantitative manner. Exemplary techniques are described in Ornstein L., Disc electrophoresis—I: Background and theory, Ann. NY Acad. Sci. 121:321-349 (1964), and Matsudiara, P T and D R Burgess, SDS microslab linear gradient polyacrylamide gel electrophoresis, Anal. Biochem. 87:386-396 (1987), each of which is herein incorporated by reference in its entirety for teachings regarding gel-shift assays.

In a general gel-shift assay, purified proteins or crude cell extracts can be incubated with a labeled (e.g., $^{32}$P-radiolabeled) DNA or RNA probe, followed by separation of the complexes from the free probe through a nondenaturing polyacrylamide gel. The complexes migrate more slowly through the gel than unbound probe. Depending on the activity of the binding protein, a labeled probe can be either double-stranded or single-stranded. For the detection of DNA binding proteins such as transcription factors, either purified or partially purified proteins, or nuclear cell extracts can be used. For detection of RNA binding proteins, either purified or partially purified proteins, or nuclear or cytoplasmic cell extracts can be used. The specificity of the DNA or RNA binding protein for the putative binding site is established by competition experiments using DNA or RNA fragments or oligonucleotides containing a binding site for the protein of interest, or other unrelated sequence. The differences in the nature and intensity of the complex formed in the presence of specific and nonspecific competitor allows identification of specific interactions. Refer to Promega, Gel Shift Assay FAQ, available at <http://www.promega.com/faq/gelshfaq.html> (last visited Mar. 25, 2005), which is herein incorporated by reference in its entirety for teachings regarding gel shift methods.

Gel shift methods can include using, for example, colloidal forms of COOMASSIE (Imperial Chemicals Industries, Ltd) blue stain to detect proteins in gels such as polyacrylamide electrophoresis gels. Such methods are described, for example, in Neuhoff et al., Electrophoresis 6:427-448 (1985), and Neuhoff et al., Electrophoresis 9:255-262 (1988), each of which is herein incorporated by reference in its entirety for teachings regarding gel shift methods. In addition to the conventional protein assay methods referenced above, a combination cleaning and protein staining composition is described in U.S. Pat. No. 5,424,000, herein incorporated by reference in its entirety for its teaching regarding gel shift methods. The solutions can include phosphoric, sulfuric, and nitric acids, and Acid Violet dye.

Radioimmune Precipitation Assay (RIPA) is a sensitive assay using radiolabeled antigens to detect specific antibodies in serum. The antigens are allowed to react with the serum and then precipitated using a special reagent such as, for example, protein A sepharose beads. The bound radiolabeled immunoprecipitate is then commonly analyzed by gel electrophoresis. Radioimmunoprecipitation assay (RIPA) is often used as a confirmatory test for diagnosing the presence of HIV antibodies. RIPA is also referred to in the art as Farr Assay, Precipitin Assay, Radioimmune Precipitin Assay; Radioimmunoprecipitation Analysis; Radioimmunoprecipitation Analysis, and Radioimmunoprecipitation Analysis.

While the above immunoassays that utilize electrophoresis to separate and detect the specific proteins of interest allow for evaluation of protein size, they are not very sensitive for evaluating protein concentration. However, also contemplated are immunoassays wherein the protein or antibody specific for the protein is bound to a solid support (e.g., tube, well, bead, or cell) to capture the antibody or protein of interest, respectively, from a sample, combined with a method of detecting the protein or antibody specific for the protein on the support. Examples of such immunoassays include Radioimmunoassay (RIA), Enzyme-Linked Immunosorbent Assay (ELISA), Flow cytometry, protein array, multiplexed bead assay, and magnetic capture.

Radioimmunoassay (RIA) is a classic quantitative assay for detection of antigen-antibody reactions using a radioactively labeled substance (radioligand), either directly or indirectly, to measure the binding of the unlabeled substance to a specific antibody or other receptor system. Radioimmunoassay is used, for example, to test hormone levels in the blood without the need to use a bioassay. Non-immunogenic substances (e.g., haptens) can also be measured if coupled to larger carrier proteins (e.g., bovine gamma-globulin or human serum albumin) capable of inducing antibody formation. RIA involves mixing a radioactive antigen (because of the ease with which iodine atoms can be introduced into tyrosine residues in a protein, the radioactive isotopes $^{125}$I or $^{131}$I are often used) with antibody to that antigen. The antibody is generally linked to a solid support, such as a tube or beads. Unlabeled or "cold" antigen is then adding in known quantities and measuring the amount of labeled antigen displaced. Initially, the radioactive antigen is bound to the antibodies. When cold antigen is added, the two compete for antibody binding sites—and at higher concentrations of cold antigen, more binds to the antibody, displacing the radioactive variant. The bound antigens are separated from the unbound ones in solution and the radioactivity of each used to plot a binding curve. The technique is both extremely sensitive, and specific.

Enzyme-Linked Immunosorbent Assay (ELISA), or more generically termed EIA (Enzyme ImmunoAssay), is an immunoassay that can detect an antibody specific for a protein. In such an assay, a detectable label bound to either an antibody-binding or antigen-binding reagent is an enzyme. When exposed to its substrate, this enzyme reacts in such a manner as to produce a chemical moiety which can be detected, for example, by spectrophotometric, fluorometric or visual means. Enzymes which can be used to detectably label reagents useful for detection include, but are not limited to, horseradish peroxidase, alkaline phosphatase, glucose oxidase, β-galactosidase, ribonuclease, urease, catalase, malate dehydrogenase, staphylococcal nuclease, asparaginase, yeast alcohol dehydrogenase, alpha.-glycerophosphate dehydrogenase, triose phosphate isomerase, glucose-6-phosphate dehydrogenase, glucoamylase and acetylcholinesterase. For descriptions of ELISA procedures, see Voller, A. et al., J. Clin. Pathol. 31:507-520 (1978); Butler, J. E., Meth. Enzymol. 73:482-523 (1981); Maggio, E. (ed.), Enzyme Immunoassay, CRC Press, Boca Raton, 1980; Butler, J. E., In: Structure of Antigens, Vol. 1 (Van Regenmortel, M., CRC Press, Boca Raton, 1992, pp. 209-259; Butler, J. E., In: van Oss, C. J. et al., (eds), Immunochemistry, Marcel Dekker, Inc., New York, 1994, pp. 759-803; Butler, J. E. (ed.), Immunochemistry of Solid-Phase Immunoassay, CRC Press, Boca Raton, 1991); Crowther, "ELISA: Theory and Practice," In: Methods in Molecule Biology, Vol. 42, Humana Press; New Jersey, 1995;U.S. Pat. No. 4,376,110, each of which is incorporated herein by reference in its entirety and specifically for teachings regarding ELISA methods.

Variations of ELISA techniques are known to those of skill in the art. In one variation, antibodies that can bind to proteins can be immobilized onto a selected surface exhibiting protein affinity, such as a well in a polystyrene microtiter plate. Then, a test composition suspected of containing a marker antigen can be added to the wells. After binding and washing to remove non-specifically bound immunocomplexes, the bound antigen can be detected. Detection can be achieved by the addition of a second antibody specific for the target protein, which is linked to a detectable label. This type of ELISA is a simple "sandwich ELISA." Detection also can be achieved by the addition of a second antibody, followed by the addition of a third antibody that has binding affinity for the second antibody, with the third antibody being linked to a detectable label.

Another variation is a competition ELISA. In competition ELISA's, test samples compete for binding with known amounts of labeled antigens or antibodies. The amount of reactive species in the sample can be determined by mixing the sample with the known labeled species before or during incubation with coated wells. The presence of reactive species in the sample acts to reduce the amount of labeled species available for binding to the well and thus reduces the ultimate signal.

Regardless of the format employed, ELISAs have certain features in common, such as coating, incubating or binding, washing to remove non-specifically bound species, and detecting the bound immunecomplexes. Antigen or antibodies can be linked to a solid support, such as in the form of plate, beads, dipstick, membrane or column matrix, and the sample to be analyzed applied to the immobilized antigen or antibody. In coating a plate with either antigen or antibody, one will generally incubate the wells of the plate with a solution of the antigen or antibody, either overnight or for a specified period of hours. The wells of the plate can then be washed to remove incompletely adsorbed material. Any remaining available surfaces of the wells can then be "coated" with a nonspecific protein that is antigenically neutral with regard to the test antisera. These include bovine serum albumin (BSA), casein and solutions of milk powder. The coating allows for blocking of nonspecific adsorption sites on the immobilizing surface and thus reduces the background caused by nonspecific binding of antisera onto the surface.

In ELISAs, a secondary or tertiary detection means rather than a direct procedure can also be used. Thus, after binding of a protein or antibody to the well, coating with a nonreactive material to reduce background, and washing to remove unbound material, the immobilizing surface is contacted with the control clinical or biological sample to be tested under conditions effective to allow immunecomplex (antigen/antibody) formation. Detection of the immunecomplex then requires a labeled secondary binding agent or a secondary binding agent in conjunction with a labeled third binding agent.

"Under conditions effective to allow immunecomplex (antigen/antibody) formation" means that the conditions include diluting the antigens and antibodies with solutions such as BSA, bovine gamma globulin (BGG) and phosphate buffered saline (PBS)/Tween so as to reduce non-specific binding and to promote a reasonable signal to noise ratio.

The suitable conditions also mean that the incubation is at a temperature and for a period of time sufficient to allow effective binding. Incubation steps can typically be from about 1 minute to twelve hours, at temperatures of about 20° to 30° C., or can be incubated overnight at about 0° C. to about 10° C.

Following all incubation steps in an ELISA, the contacted surface can be washed so as to remove non-complexed material. A washing procedure can include washing with a solution such as PBS/Tween or borate buffer. Following the formation of specific immunecomplexes between the test sample and the originally bound material, and subsequent washing, the occurrence of even minute amounts of immunecomplexes can be determined.

To provide a detecting means, the second or third antibody can have an associated label to allow detection, as described above. This can be an enzyme that can generate color development upon incubating with an appropriate chromogenic substrate. Thus, for example, one can contact and incubate the first or second immunecomplex with a labeled antibody for a period of time and under conditions that favor the development of further immunecomplex formation (e.g., incubation for 2 hours at room temperature in a PBS-containing solution such as PBS-Tween).

After incubation with the labeled antibody, and subsequent to washing to remove unbound material, the amount of label can be quantified, e.g., by incubation with a chromogenic substrate such as urea and bromocresol purple or 2,2'-azido-di-(3-ethyl-benzthiazoline-6-sulfonic acid [ABTS] and $H_2O_2$, in the case of peroxidase as the enzyme label. Quantitation can then be achieved by measuring the degree of color generation, e.g., using a visible spectra spectrophotometer.

Protein arrays are solid-phase ligand binding assay systems using immobilized proteins on surfaces which include glass, membranes, microtiter wells, mass spectrometer plates, and beads or other particles. The assays are highly parallel (multiplexed) and often miniaturized (microarrays, protein chips). Their advantages include being rapid and automatable, capable of high sensitivity, economical on reagents, and giving an abundance of data for a single experiment. Bioinformatics support is important; the data handling demands sophisticated software and data comparison analysis. However, the software can be adapted from that used for DNA arrays, as can much of the hardware and detection systems.

One of the chief formats is the capture array, in which ligand-binding reagents, which are usually antibodies but can also be alternative protein scaffolds, peptides or nucleic acid aptamers, are used to detect target molecules in mixtures such as plasma or tissue extracts. In diagnostics, capture arrays can be used to carry out multiple immunoassays in parallel, both testing for several analytes in individual sera for example and testing many serum samples simultaneously. In proteomics, capture arrays are used to quantitate and compare the levels of proteins in different samples in health and disease, i.e. protein expression profiling. Proteins other than specific ligand binders are used in the array format for in vitro functional interaction screens such as protein-protein, protein-DNA, protein-drug, receptor-ligand, enzyme-substrate, etc. The capture reagents themselves are selected and screened against many proteins, which can also be done in a multiplex array format against multiple protein targets.

For construction of arrays, sources of proteins include cell-based expression systems for recombinant proteins, purification from natural sources, production in vitro by cell-free translation systems, and synthetic methods for peptides. Many of these methods can be automated for high throughput production. For capture arrays and protein function analysis, it is important that proteins should be correctly folded and functional; this is not always the case, e.g. where recombinant proteins are extracted from bacteria under denaturing conditions. Nevertheless, arrays of denatured proteins are useful in screening antibodies for cross-reactivity, identifying autoantibodies and selecting ligand binding proteins.

Protein arrays have been designed as a miniaturization of familiar immunoassay methods such as ELISA and dot blotting, often utilizing fluorescent readout, and facilitated by robotics and high throughput detection systems to enable multiple assays to be carried out in parallel. Commonly used physical supports include glass slides, silicon, microwells, nitrocellulose or PVDF membranes, and magnetic and other microbeads. While microdrops of protein delivered onto planar surfaces are the most familiar format, alternative architectures include CD centrifugation devices based on developments in microfluidics (Gyros, Monmouth Junction, N.J.) and specialised chip designs, such as engineered microchannels in a plate (e.g., The Living Chip™, Biotrove, Woburn, Mass.) and tiny 3D posts on a silicon surface (Zyomyx, Hayward Calif.). Particles in suspension can also be used as the basis of arrays, providing they are coded for identification; systems include color coding for microbeads (Luminex, Austin, Tex.; Bio-Rad Laboratories, Hercules, Calif.) and semiconductor nanocrystals (e.g., QDots™, Quantum Dot, Hayward, Calif.), and barcoding for beads (UltraPlex™, SmartBead Technologies Ltd, Babraham, Cambridge, UK) and multimetal microrods (e.g., Nanobarcodes™ particles, Nanoplex Technologies, Mountain View, Calif.). Beads can also be assembled into planar arrays on semiconductor chips (LEAPS technology, BioArray Solutions, Warren, N.J.).

Immobilization of proteins involves both the coupling reagent and the nature of the surface being coupled to. A good protein array support surface is chemically stable before and after the coupling procedures, allows good spot morphology, displays minimal nonspecific binding, does not contribute a background in detection systems, and is compatible with different detection systems. The immobilization method used are reproducible, applicable to proteins of different properties (size, hydrophilic, hydrophobic), amenable to high throughput and automation, and compatible with retention of fully functional protein activity. Orientation of the surface-bound protein is recognized as an important factor in presenting it to ligand or substrate in an active state; for capture arrays the most efficient binding results are obtained with orientated capture reagents, which generally require site-specific labeling of the protein.

Both covalent and noncovalent methods of protein immobilization are used and have various pros and cons. Passive adsorption to surfaces is methodologically simple, but allows little quantitative or orientational control; it may or may not alter the functional properties of the protein, and reproducibility and efficiency are variable. Covalent coupling methods provide a stable linkage, can be applied to a range of proteins and have good reproducibility; however, orientation may be variable, chemical derivatization may alter the function of the protein and requires a stable interactive surface. Biological capture methods utilizing a tag on the protein provide a stable linkage and bind the protein specifically and in reproducible orientation, but the biological reagent must first be immobilized adequately and the array may require special handling and have variable stability.

Several immobilization chemistries and tags have been described for fabrication of protein arrays. Substrates for covalent attachment include glass slides coated with amino- or aldehyde-containing silane reagents. In the Versalinx™ system (Prolinx, Bothell, Wash.) reversible covalent coupling is achieved by interaction between the protein derivatised with phenyldiboronic acid, and salicylhydroxamic acid immobilized on the support surface. This also has low background binding and low intrinsic fluorescence and allows the immobilized proteins to retain function. Noncovalent binding of unmodified protein occurs within porous structures such as HydroGel™ (PerkinElmer, Wellesley, Mass.), based on a 3-dimensional polyacrylamide gel; this substrate is reported to give a particularly low background on glass microarrays, with a high capacity and retention of protein function. Widely used biological coupling methods are through biotin/streptavidin or hexahistidine/Ni interactions, having modified the protein appropriately. Biotin may be conjugated to a polylysine backbone immobilised on a surface such as titanium dioxide (Zyomyx, Hayward, Calif.) or tantalum pentoxide (Zeptosens, Witterswil, Switzerland).

Array fabrication methods include robotic contact printing, ink-jetting, piezoelectric spotting and photolithography. A number of commercial arrayers are available (e.g. Packard Biosciences, PerkinElmer, Wellesley, Mass.) as well as manual equipment (V & P Scientific, San Diego, Calif.). Bacterial colonies can be robotically gridded onto PVDF membranes for induction of protein expression in situ.

At the limit of spot size and density are nanoarrays, with spots on the nanometer spatial scale, enabling thousands of reactions to be performed on a single chip less than 1 mm square. BioForce Laboratories have developed nanoarrays with 1521 protein spots in 85 sq microns, equivalent to 25 million spots per sq cm, at the limit for optical detection; their readout methods are fluorescence and atomic force microscopy (AFM).

Fluorescence labeling and detection methods are widely used. The same instrumentation as used for reading DNA microarrays is applicable to protein arrays. For differential display, capture (e.g., antibody) arrays can be probed with fluorescently labeled proteins from two different cell states, in which cell lysates are directly conjugated with different fluorophores (e.g. Cy-3, Cy-5) and mixed, such that the color acts as a readout for changes in target abundance. Fluorescent readout sensitivity can be amplified 10-100 fold by tyramide signal amplification (TSA) (PerkinElmer Lifesciences, Wellesley, Mass.). Planar waveguide technology (Zeptosens, Witterswil, Switzerland) enables ultrasensitive fluorescence detection, with the additional advantage of no intervening washing procedures. High sensitivity can also be achieved with suspension beads and particles, using phycoerythrin as label (Luminex, Austin, Tex.) or the properties of semiconductor nanocrystals (Quantum Dot). A number of novel alternative readouts have been developed, especially in the commercial biotech arena. These include adaptations of surface plasmon resonance (HTS Biosystems, Intrinsic Bioprobes, Tempe, Ariz.), rolling circle DNA amplification (Molecular Staging, New Haven Conn.), mass spectrometry (Intrinsic Bioprobes; Ciphergen, Fremont, Calif.), resonance light scattering (Genicon Sciences, San Diego, Calif.) and atomic force microscopy (BioForce Laboratories).

Capture arrays form the basis of diagnostic chips and arrays for expression profiling. They employ high affinity capture reagents, such as conventional antibodies, single domains, engineered scaffolds, peptides or nucleic acid aptamers, to bind and detect specific target ligands in high throughput manner.

Antibody arrays have the required properties of specificity and acceptable background, and some are available commercially (BD Biosciences, San Jose, Calif.; Clontech, Mountain View, Calif.; BioRad; Sigma, St. Louis, Mo.). Antibodies for capture arrays are made either by conventional immunization (polyclonal sera and hybridomas), or as recombinant fragments, usually expressed in *E. coli*, after selection from phage or ribosome display libraries (Cambridge Antibody Technology, Cambridge, UK; BioInvent, Lund, Sweden; Affitech, Walnut Creek, Calif.; Biosite, San Diego, Calif.). In addition to the conventional antibodies, Fab and scFv fragments, single V-domains from camelids or engineered human equivalents (Domantis, Waltham, Mass.) may also be useful in arrays.

The term "scaffold" refers to ligand-binding domains of proteins, which are engineered into multiple variants capable of binding diverse target molecules with antibody-like properties of specificity and affinity. The variants can be produced in a genetic library format and selected against individual targets by phage, bacterial or ribosome display. Such ligand-binding scaffolds or frameworks include 'Affibodies' based on *Staph. aureus* protein A (Affibody, Bromma, Sweden), 'Trinectins' based on fibronectins (Phylos, Lexington, Mass.) and 'Anticalins' based on the lipocalin structure (Pieris Proteolab, Freising-Weihenstephan, Germany). These can be used on capture arrays in a similar fashion to antibodies and may have advantages of robustness and ease of production.

Nonprotein capture molecules, notably the single-stranded nucleic acid aptamers which bind protein ligands with high specificity and affinity, are also used in arrays (SomaLogic, Boulder, Colo.). Aptamers are selected from libraries of oligonucleotides by the Selex™ procedure and their interaction with protein can be enhanced by covalent attachment, through incorporation of brominated deoxyuridine and UV-activated crosslinking (photoaptamers). Photocrosslinking to ligand reduces the crossreactivity of aptamers due to the specific steric requirements. Aptamers have the advantages of ease of production by automated oligonucleotide synthesis and the stability and robustness of DNA; on photoaptamer arrays, universal fluorescent protein stains can be used to detect binding.

Protein analytes binding to antibody arrays may be detected directly or via a secondary antibody in a sandwich assay. Direct labelling is used for comparison of different samples with different colours. Where pairs of antibodies directed at the same protein ligand are available, sandwich immunoassays provide high specificity and sensitivity and are therefore the method of choice for low abundance proteins such as cytokines; they also give the possibility of detection of protein modifications. Label-free detection methods, including mass spectrometry, surface plasmon resonance and atomic force microscopy, avoid alteration of ligand. What is required from any method is optimal sensitivity and specificity, with low background to give high signal to noise. Since analyte concentrations cover a wide range, sensitivity has to be tailored appropriately; serial dilution of the sample or use of antibodies of different affinities are solutions to this problem. Proteins of interest are frequently those in low concentration in body fluids and extracts, requiring detection in the pg range or lower, such as cytokines or the low expression products in cells.

An alternative to an array of capture molecules is one made through "molecular imprinting" technology, in which peptides (e.g., from the C-terminal regions of proteins) are used as templates to generate structurally complementary, sequence-specific cavities in a polymerizable matrix; the cavities can then specifically capture (denatured) proteins that have the appropriate primary amino acid sequence (ProteinPrint™, Aspira Biosystems, Burlingame, Calif.).

Another methodology which can be used diagnostically and in expression profiling is the ProteinChip® array (Ciphergen, Fremont, Calif.), in which solid phase chromatographic surfaces bind proteins with similar characteristics of charge or hydrophobicity from mixtures such as plasma or tumour extracts, and SELDI-TOF mass spectrometry is used to detection the retained proteins.

Large-scale functional chips have been constructed by immobilizing large numbers of purified proteins and used to assay a wide range of biochemical functions, such as protein interactions with other proteins, drug-target interactions, enzyme-substrates, etc. Generally they require an expression library, cloned into E. coli, yeast or similar from which the expressed proteins are then purified, e.g. via a His tag, and immobilized. Cell free protein transcription/translation is a viable alternative for synthesis of proteins which do not express well in bacterial or other in vivo systems.

For detecting protein-protein interactions, protein arrays can be in vitro alternatives to the cell-based yeast two-hybrid system and may be useful where the latter is deficient, such as interactions involving secreted proteins or proteins with disulphide bridges. High-throughput analysis of biochemical activities on arrays has been described for yeast protein kinases and for various functions (protein-protein and protein-lipid interactions) of the yeast proteome, where a large proportion of all yeast open-reading frames was expressed and immobilised on a microarray. Large-scale 'proteome chips' promise to be very useful in identification of functional interactions, drug screening, etc. (Proteometrix, Branford, Conn.).

As a two-dimensional display of individual elements, a protein array can be used to screen phage or ribosome display libraries, in order to select specific binding partners, including antibodies, synthetic scaffolds, peptides and aptamers. In this way, 'library against library' screening can be carried out. Screening of drug candidates in combinatorial chemical libraries against an array of protein targets identified from genome projects is another application of the approach.

A multiplexed bead assay, such as, for example, the BD™ Cytometric Bead Array, is a series of spectrally discrete particles that can be used to capture and quantitate soluble analytes. The analyte is then measured by detection of a fluorescence-based emission and flow cytometric analysis. Multiplexed bead assay generates data that is comparable to ELISA based assays, but in a "multiplexed" or simultaneous fashion. Concentration of unknowns is calculated for the cytometric bead array as with any sandwich format assay, i.e. through the use of known standards and plotting unknowns against a standard curve. Further, multiplexed bead assay allows quantification of soluble analytes in samples never previously considered due to sample volume limitations. In addition to the quantitative data, powerful visual images can be generated revealing unique profiles or signatures that provide the user with additional information at a glance.

The MMP/TIMP profiles disclosed herein are based on measurements of individual MMPs or TIMPs. The amounts of these can be measured by any means known to provide an acceptable indication of how much of any of these is present in the sample being analyzed. An example of a means of measuring is provided in the Examples. The process of measuring an amount of an analyte (e.g., MPP or TIMP) includes measurement of no amount or an undetectable amount of the analyte.

7. Antibodies

Antibodies specific for MMPs and TIMPs are known and commercially available. The list of antibodies for commercially available MMPs and TIMPs include, but are not limited to those presented in Table 1.

TABLE 1

Commercially Available MMP and TIMP antibodies

| Analyte | Vendor | Catalog # |
|---------|--------|-----------|
| MMP-1 | Chemicon | AB806 |
| MMP-2 | Chemicon | MAB3308 |
|  | Chemicon | AB809 |
| MMP-3 | Chemicon | AB811 |
|  | Oncogene | IM36L |
| MMP-7 | Oncogene | PC492 |
|  | Chemicon | AB8118 |
| MMP-8 | BioVision | 3528-100 |
|  | Oncogene | PC493 |
| MMP-9 | Chemicon | AB19047 |
|  | Chemicon | AB804 |
| MMP-13 | Chemicon | AB8114 |
|  | BioVision | 3533-100 |
|  | Chemicon | MAB3321 |
| MMP-14 | Chemicon | AB815 |
|  | Chemicon | MAB3317 |
|  | Chemicon | AB8221 |
| TIMP-1 | ABR | OPA1-08512 |
|  | Chemicon | AB8116 |
| TIMP-2 | Chemicon | AB801 |
|  | Chemicon | MAB3310 |
|  | Chemicon | AB8107 |
| TIMP-3 | Triple Point Biologics | H-TIMP-3 |
|  | Triple Point Biologics | RPIT3 |
| TIMP-4 | Chemicon | AB816 |
|  | R & D Systems | MAB974 |
|  | Santa Cruz | SC-9375 |

The term "antibodies" is used herein in a broad sense and includes both polyclonal and monoclonal antibodies. In addition to intact immunoglobulin molecules, also included in the term "antibodies" are fragments or polymers of those immunoglobulin molecules, and human or humanized versions of immunoglobulin molecules or fragments thereof, as long as they are chosen for their ability to interact with MMPs or TIMPs. The antibodies can be tested for their desired activity using the in vitro assays described herein, or by analogous methods, after which their in vivo therapeutic and/or prophylactic activities are tested according to known clinical testing methods.

The term "monoclonal antibody" as used herein refers to an antibody obtained from a substantially homogeneous population of antibodies, i.e., the individual antibodies within the population are identical except for possible naturally occurring mutations that may be present in a small subset of the antibody molecules. The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, as long as they exhibit the desired antagonistic activity (See, U.S. Pat. No. 4,816,567 and Morrison et al., Proc. Natl. Acad. Sci. USA, 81:6851-6855 (1984)).

The disclosed monoclonal antibodies can be made using any procedure which produces monoclonal antibodies. For example, disclosed monoclonal antibodies can be prepared using hybridoma methods, such as those described by Kohler and Milstein, Nature, 256:495 (1975). In a hybridoma method, a mouse or other appropriate host animal is typically immunized with an immunizing agent to elicit lymphocytes that produce or are capable of producing antibodies that will specifically bind to the immunizing agent. Alternatively, the lymphocytes may be immunized in vitro, e.g., using the HIV Env-CD4-co-receptor complexes described herein.

The monoclonal antibodies may also be made by recombinant DNA methods, such as those described in U.S. Pat. No. 4,816,567 (Cabilly et al.). DNA encoding the disclosed monoclonal antibodies can be readily isolated and sequenced using conventional procedures (e.g., by using oligonucleotide probes that are capable of binding specifically to genes encoding the heavy and light chains of murine antibodies). Libraries of antibodies or active antibody fragments can also be generated and screened using phage display techniques, e.g., as described in U.S. Pat. No. 5,804,440 to Burton et al. and U.S. Pat. No. 6,096,441 to Barbas et al.

In vitro methods are also suitable for preparing monovalent antibodies. Digestion of antibodies to produce fragments thereof, particularly, Fab fragments, can be accomplished using routine techniques known in the art. For instance, digestion can be performed using papain. Examples of papain digestion are described in WO 94/29348 published Dec. 22, 1994 and U.S. Pat. No. 4,342,566. Papain digestion of antibodies typically produces two identical antigen binding fragments, called Fab fragments, each with a single antigen binding site, and a residual Fc fragment. Pepsin treatment yields a fragment that has two antigen combining sites and is still capable of cross-linking antigen.

The fragments, whether attached to other sequences or not, can also include insertions, deletions, substitutions, or other selected modifications of particular regions or specific amino acids residues, provided the activity of the antibody or antibody fragment is not significantly altered or impaired compared to the non-modified antibody or antibody fragment. These modifications can provide for some additional property, such as to remove/add amino acids capable of disulfide bonding, to increase its bio-longevity, to alter its secretory characteristics, etc. In any case, the antibody or antibody fragment must possess a bioactive property, such as specific binding to its cognate antigen. Functional or active regions of the antibody or antibody fragment may be identified by mutagenesis of a specific region of the protein, followed by expression and testing of the expressed polypeptide. Such methods are readily apparent to a skilled practitioner in the art and can include site-specific mutagenesis of the nucleic acid encoding the antibody or antibody fragment. (Zoller, M. J. Curr. Opin. Biotechnol. 3:348-354, 1992).

As used herein, the term "antibody" or "antibodies" can also refer to a human antibody and/or a humanized antibody. Many non-human antibodies (e.g., those derived from mice, rats, or rabbits) are naturally antigenic in humans, and thus can give rise to undesirable immune responses when administered to humans. Therefore, the use of human or humanized antibodies in the methods serves to lessen the chance that an antibody administered to a human will evoke an undesirable immune response.

8. Reference Values

Provided are profiles of MMPs and/or TIMPs that are an indication of higher risk of recurrence of atrial fibrillation. The profiles that are indication of higher risk of recurrence of atrial fibrillation in a subject can be relative to a normal value. A normal value for a given analyte (MMP or TIMP) can be a reference value for an age matched subject that is confirmed to have no evidence of significant cardiovascular disease, or of AF. Thus, the normal value can be a population-based value derived from a significant number of healthy individuals. These reference normal values can be obtained from population based studies. There are large population based studies for example that have identified relative levels of TIMP-1 (Framingham Heart Study, Circulation 2004; 109:2850-2856) in a reference group to approximately 800 ng/mL which is consistent with the reference control values disclosed herein.

Alternatively, the normal value can be a value that is considered normal for a given subject. For example, baseline measurements of the relevant analytes can be made for a healthy individual, and used for comparison against later-acquired measurements from that individual to identify current disease or progression toward AF.

A discrete observation, e.g., for MMP-13, is where a continuous variable such as a plasma concentration of a given analyte is converted to a dichotomous variable. In this particular instance a +/−value would be assigned to MMP-13 where a value of greater than 10 ng/mL would be considered a detectable, or positive value and a value less than 10 ng/mL to be a negative value.

For example, provided is a method of predicting recurrence of atrial fibrillation in a subject comprising measuring MMP and/or TIMP levels in a tissue or bodily fluid of the subject and comparing said levels to reference values. Thus, normal values for one, two, three, four, five, six, seven, or eight of MMP-2, MMP-9, MMP-7, MMP-13, MMP-8, TIMP-1, TIMP-2, and TIMP-4 is an indication of the absence of a prediction of AF.

In some aspects, MMP-2 plasma levels within normal range is an indication of the absence of a prediction of AF. In some aspects, MMP-9 plasma levels within normal range is an indication of the absence of a prediction of AF. In some aspects, MMP-13 plasma levels within normal range is an indication of the absence of AF or a prediction of AF. In some aspects, TIMP-1 plasma levels within normal range is an indication of the absence of AF or a prediction of AF. In some aspects, TIMP-2 plasma levels within normal range is an indication of the absence of AF or a prediction of AF. In some aspects, TIMP-4 plasma levels within normal range is an indication of the absence of AF or a prediction of AF.

In some aspects, MMP-2 plasma levels greater than about 1000 ng/ml, including greater than about 1000, 1100, 1200, 1300, 1400, and 1500 ng/ml, is an indication of the absence of AF or a prediction of AF.

In some aspects, MMP-9 plasma levels less than about 20 ng/ml, including less than about 20, 19, 18, 17, 16, 15, 14, 13, 12, 11, 10, 9, 8, 7, 6, 5, 4, 3, 2, or 1 ng/ml, is an indication of the absence of AF or a prediction of AF.

In some aspects, detectable MMP-13 plasma levels greater than about 5 ng/ml, including less than about 5, 6, 7, 8, 9, 10, 11, 12, 13, 14, 15, 20 ng/ml, is an indication of the absence of AF or a prediction of AF.

In some aspects, TIMP-1 plasma levels less than about 1000 ng/ml, including greater than about 1000, 900, 800, 700, 600, 500, 400, 300, 200, 100, 50, 40, 30, 20, or 10 ng/ml, is an indication of the absence of AF or a prediction of AF.

In some aspects, TIMP-2 plasma levels less than about 50 ng/ml, including greater than about 50, 49, 48, 47, 46, 45, 44, 43, 42, 41, 40, 35, 30, 25, 20, 15, or 10 ng/ml, is an indication of the absence of AF or a prediction of AF.

In some aspects, TIMP-4 plasma levels less than about 2 ng/ml, including greater than about 2.0, 1.9, 1.8, 1.7, 1.6, 1.5, 1.4, 1.3, 1.2, 1.1, 1.0, 0.5, or 0.1 ng/ml, is an indication of the absence of AF or a prediction of AF.

The method can further comprise measuring plasma levels of two or more MMPs and/or TIMPs. For example, the method can comprise measuring two, three, four, five, six, seven, or eight of MMP-2, MMP-9, MMP-7, MMP-13, MMP-8, TIMP-1, TIMP-2, and TIMP-4. Thus, the method can comprise measuring MMP-2 and MMP-9; MMP-2 and MMP-13; MMP-9 and TIMP-1; MMP-13 and TIMP-2;

MMP-13 and TIMP-4; MMP-2, MMP-13 and TIMP-1; MMP-2, MMP-13 and TIMP-2; MMP-2, MMP-13 and TIMP-4; or MMP-2, MMP-13, TIMP-1, TIMP-2, and TIMP-4. Other combinations of these analytes are contemplated and disclosed herein.

The method can further comprise calculating the ratio of one or more of the MMPs or TIMPs to other MMPs or TIMPs. For example, the method can comprise calculating the ratio of MMP-9 to TIMP-1, TIMP-2 or TIMP-4 and comparing them to normal ratios.

For example, in some aspects, a ratio of MMP-9/TIMP-1 plasma levels greater than about $7 \times 10^3$, including greater than about $7 \times 10^3$, $8 \times 10^3$, $9 \times 10^3$, $10 \times 10^3$, $11 \times 10^3$, $12 \times 10^3$, $13 \times 10^3$, or $14 \times 10^3$, is an indication of the absence of AF or a prediction of AF.

In some aspects, a ratio of MMP-9/TIMP-2 plasma levels greater than about $10 \times 10^4$, including greater than about $10 \times 10^4$, $20 \times 10^4$, $30 \times 10^4$, or $40 \times 10^4$, is an indication of the absence of AF or a prediction of AF.

In some aspects, a ratio of MMP-9/TIMP-4 plasma levels greater than about 1, including greater than about 1, 2, 3, 4, 5, 6, 7, 8, or 9, is an indication of the absence of AF or a prediction of AF.

Further provided are methods for predicting whether a subject with a history of atrial fibrillation will have recurrence of atrial fibrillation following a cardioversion procedure. The method can comprising measuring at least one MMP level and/or one TIMP leve in a body fluid from the subject to produce an MMP profile, a TIMP profile or a MMP/TIMP profile. The profile can be used to determine whether the subject will have a recurrence of atrial fibrillation following the cardioversion procedure. The use of a given profile can comprise comparing a least one measured MMP and/or TIMP level of the profile to at least one corresponding control MMP level and/or TIMP level to determine the relative increase or decrease of each respective MMP level and/or TIMP level to the control MMP level and or TIMP level. In some aspects, the MMP profile comprises measurements of levels of a plurality of MMPs. Similarly the TIMP profile can comprise measurements of levels of a plurality of TIMPs and a MMP/TIMP profile can comprise a plurality of MMPs and/or a plurality of TIMPs.

Methods are also provided for determining whether a subject with a history of atrial fibrillation should be treated with an implantable pacer. These methods can comprise measuring at least one MMP level and/or at least one TIMP level in a body fluid from the subject to produce an MMP, TIMP or a MMP/TIMP profile. The produced profile can be used to determine whether the subject will have a recurrence of atrial fibrillation following a cardioversion procedure, a likely recurrence of atrial fibrillation indicating treatment with an implantable pacer.

9. Prognosis

Provided herein is a method of predicting recurrence of atrial fibrillation in a subject, comprising measuring MMP and/or TIMP levels in a tissue or bodily fluid of the subject and comparing said levels to reference values.

As used herein "recurrence" can include paroxysmal, persistent, and chronic episodes of AF in a subject that has been treated for a prior episode of AF. Predicting recurrence of AF in a subject with a history of (including presenting with) AF can be done prior to administration of AF treatment and to determine if the selected AF treatment will likely be followed by recurrence of AF in that subject. For example, the recurrence of AF can be predicted prior to electrical cardioversion. If it is determine that electrical cardioversion will correct the AF without recurrence of AF then electrical cardioversion can be selected as the treatment modality of choice. If it is determined that electrical cardioversion will not result in sustained AF correction, then another treatment modality can be selected. For example, an implantable pacer device can be selected or pharmacological pacing can be used instead of electrical cardioversion if it is determined that there will be recurrence with electrical cardioversion. Moreover, MMP and TIMP levels can be used to select treatment with an implantable pacer device, ablation, or by pharmacological pacing.

In some aspects, MMP-9 plasma levels greater than the normal value is an indication of higher risk of recurrence of atrial fibrillation. For example, an amount of MMP-9 at least about 50%, 100%, 150%, 200%, 250%, 300%, 350%, 400%, 450%, or 500% greater than the normal mean value can be an indication of higher risk of recurrence of atrial fibrillation. In some aspects, MMP-9 plasma levels greater than about 20 ng/ml, including greater than about 20, 21, 22, 23, 24, 25, 26, 27, 28, 29, 30, 31, 32, 33, 34, 35, 36, 37, 38, 39, 40, 45, 50, 55, 60, 65, 70, 75, 80, 85, 90, 95, or 100 ng/ml, is an indication of higher risk of recurrence of atrial fibrillation.

In some aspects, undetectable MMP-13 plasma levels is an indication of higher risk of recurrence of atrial fibrillation. In some aspects, MMP-13 plasma levels less than about 10 ng/ml, including less than about 10, 9, 8, 7, 6, 5, 4, 3, 2, or 1 ng/ml, is an indication of higher risk of recurrence of atrial fibrillation.

In some aspects, MMP-8 plasma levels less than the normal value is an indication of higher risk of recurrence of atrial fibrillation. For example, an amount of MMP-8 at least about 50%, 100%, 150%, 200%, 250%, 300%, 350%, 400%, 450%, or 500% less than the normal mean value can be an indication of higher risk of recurrence of atrial fibrillation.

In some aspects, TIMP-1 plasma levels greater than the normal value is an indication of higher risk of recurrence of atrial fibrillation. For example, an amount of TIMP-1 at least about 50%, 100%, 150%, 200%, 250%, 300%, 350%, 400%, 450%, or 500% greater than the normal mean value can be an indication of higher risk of recurrence of atrial fibrillation. In some aspects, TIMP-1 plasma levels greater than about 1000 ng/ml, including greater than about 1000, 1010, 1020, 1030, 1040, 1050, 1060, 1070, 1080, 1090, 1100, 1150, 1200, 1250, 1300, 1350, 1400, 1500, 1600, 1700, 1800, 1900, or 2000 ng/ml, is an indication of higher risk of recurrence of atrial fibrillation.

In some aspects, TIMP-2 plasma levels greater than the normal value is an indication of higher risk of recurrence of atrial fibrillation. For example, an amount of TIMP-2 at least about 50%, 100%, 150%, 200%, 250%, 300%, 350%, 400%, 450%, or 500% greater than the normal mean value can be an indication of higher risk of recurrence of atrial fibrillation. In some aspects, TIMP-2 plasma levels greater than about 50 ng/ml, including greater than about 50, 55, 60, 65, 70, 75, 80, 85, 90, 95, 100, 110, 120, 130, 140, 150, 160, 170, 180, 190, or 200 ng/ml, is an indication of higher risk of recurrence of atrial fibrillation.

In some aspects, TIMP-4 plasma levels greater than the normal value is an indication of higher risk of recurrence of atrial fibrillation. For example, an amount of TIMP-4 at least about 50%, 100%, 150%, 200%, 250%, 300%, 350%, 400%, 450%, or 500% greater than the normal mean value can be indication of higher risk of recurrence of atrial fibrillatione. In some aspects, TIMP-4 plasma levels greater than about 2 ng/ml, including greater than about 2, 3, 4, 5, 6, 7, 8, 9, 10, 15, 20, 25, 30, 35, 40, 45, or 50 ng/ml, is an indication of higher risk of recurrence of atrial fibrillation.

In some aspects, MMP-2 plasma levels within normal range is an indication of higher risk of recurrence of atrial fibrillation.

The method can further comprise measuring plasma levels of two or more MMPs and/or TIMPs. For example, the method can comprise measuring two, three, four, five, six, seven, or eight of MMP-2, MMP-9, MMP-7, MMP-13, MMP-8, TIMP-1, TIMP-2, and TIMP-4. Thus, the method can comprise measuring MMP-2 and MMP-13; MMP-13 and TIMP-1; MMP-13 and TIMP-2; MMP-13 and TIMP-4; MMP-2, MMP-13 and TIMP-1; MMP-2, MMP-13 and TIMP-2; MMP-2, MMP-13 and TIMP-4; or MMP-2, MMP-13, TIMP-1, TIMP-2, and TIMP-4. Other combinations of these analytes are contemplated and disclosed herein.

For example, provided is a method of predicting recurrence of atrial fibrillation in a subject, comprising measuring in a body fluid from the subject an amount of MMP-9, MMP-13, TIMP-1, TIMP-2, and TIMP-4. The profiles of these analytes wherein the amount of MMP-13 is undetectable (or less than 10 ng/mL), the amount of TIMP-1 is about 50% greater than normal value or greater than 1200 ng/mL, the amount of TIMP-2 is about 50% greater than normal value or greater than 50 ng/ml, the amount of TIMP-4 is at least about 50% greater than normal value or greater than 3 ng/mL, and the amount of MMP-9 is at least about 50% greater than normal value is an indication of higher risk of recurrence of atrial fibrillation.

The disclosed method can further comprise calculating the ratio of one or more of the MMPs or TIMPs to other MMPs or TIMPs. For example, the method can comprise calculating the ratio of MMP-9 to TIMP-1, TIMP-2 or TIMP-4.

In some aspects, a ratio of MMP-9/TIMP-1 plasma levels less than the normal value is an indication of higher risk of recurrence of atrial fibrillation. For example, a ratio of MMP-9/TIMP-1 at least about 50%, 100%, 150%, 200%, 250%, 300%, 350%, 400%, 450%, or 500% less than the normal mean value can be an indication of higher risk of recurrence of atrial fibrillation. For example, in some aspects, a ratio of MMP-9/TIMP-1 plasma levels less than about $7 \times 10^3$, including less than about $7 \times 10^3$, $6 \times 10^3$, $5 \times 10^3$, $4 \times 10^3$, $5 \times 10^3$, $6 \times 10^3$, $1 \times 10^3$, $9 \times 10^2$, $8 \times 10^2$, $7 \times 10^2$, $6 \times 10^2$, $5 \times 10^2$, $4 \times 10^2$, $3 \times 10^2$, $2 \times 10^2$, or $1 \times 10^2$, is an indication of higher risk of recurrence of atrial fibrillation.

In some aspects, a ratio of MMP-9/TIMP-2 plasma levels less than the normal value is an indication of higher risk of recurrence of atrial fibrillation. For example, a ratio of MMP-9/TIMP-2 at least about 50%, 100%, 150%, 200%, 250%, 300%, 350%, 400%, 450%, or 500% less than the normal mean value can be an indication of higher risk of recurrence of atrial fibrillation. In some aspects, a ratio of MMP-9/TIMP-2 plasma levels less than about $100 \times 10^3$, including less than about $100 \times 10^3$, $90 \times 10^3$, $80 \times 10^3$, $70 \times 10^3$, $60 \times 10^3$, $50 \times 10^3$, $40 \times 10^3$, $30 \times 10^3$, $20 \times 10^3$, $10 \times 10^3$, $9 \times 10^3$, $8 \times 10^3$, $7 \times 10^3$, $6 \times 10^3$, $5 \times 10^3$, $4 \times 10^3$, $3 \times 10^3$, $2 \times 10^3$, or $1 \times 10^3$, is an indication of higher risk of recurrence of atrial fibrillation.

In some aspects, a ratio of MMP-9/TIMP-4 plasma levels less than the normal value is an indication of higher risk of recurrence of atrial fibrillation. For example, a ratio of MMP-9/TIMP-4 at least about 50%, 100%, 150%, 200%, 250%, 300%, 350%, 400%, 450%, or 500% less than the normal mean value can be an indication of higher risk of recurrence of atrial fibrillation. In some aspects, a ratio of MMP-9/TIMP-4 plasma levels less than about 1, including less than about 1, 0.9, 0.8, 0.7, 0.6, 0.5, 0.4, 0.3, 0.2, 0.25, 0.2, 0.15, 0.10, 0.05, or 0.01, is an indication of higher risk of recurrence of atrial fibrillation.

10. Guiding Therapeutic Interventions

With respect to treatment, low MMP-13 and high TIMP levels could be monitored as an indicator of pharmacological efficacy. See FIGS. 3 to 6 for examples.

For example, provided is a method of predicting the effectiveness of a treatment modality for preventing recurrence of atrial fibrillation (AF), comprising measuring in a body fluid from the subject an amount of MMP-9, MMP-13, TIMP-1, TIMP-2, TIMP-4, or a combination thereof, wherein an amount of MMP-9 greater than 40 ng/ml, an amount of MMP-13 less than 5 ng/mL, an amount of TIMP-1 greater than 1500 ng/mL, an amount of TIMP-2 greater than 75 ng/mL, an amount of TIMP-4 greater than 5 ng/mL, or a combination thereof, is an indication that the treatment modality will not be effective at preventing recurrence of AF.

The treatment modality can be cardioversion. The treatment modality can be AF ablation. The treatment modality can be pulmonary vein (PV) ostial ablation.

Figure 3:
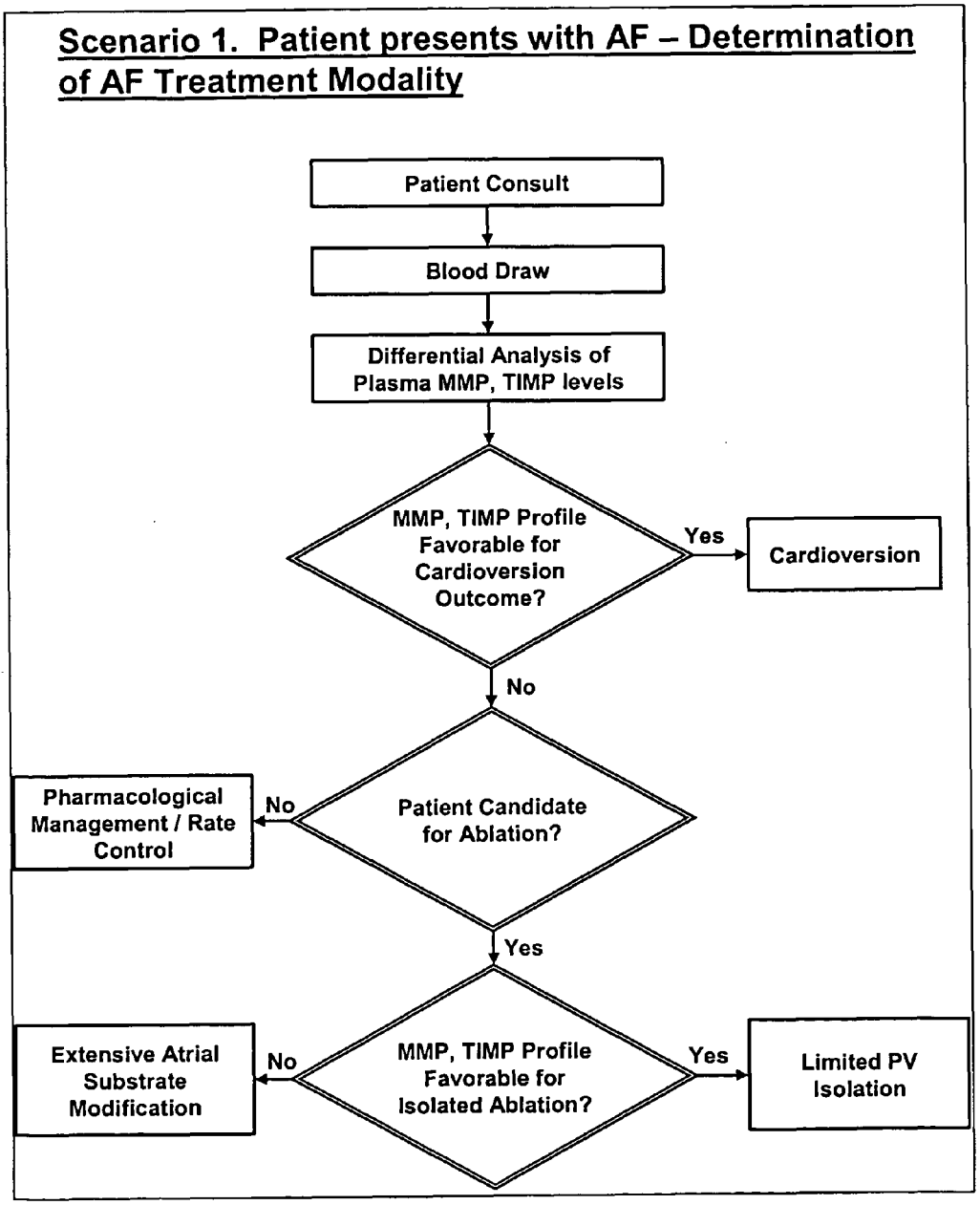
Figure 5:
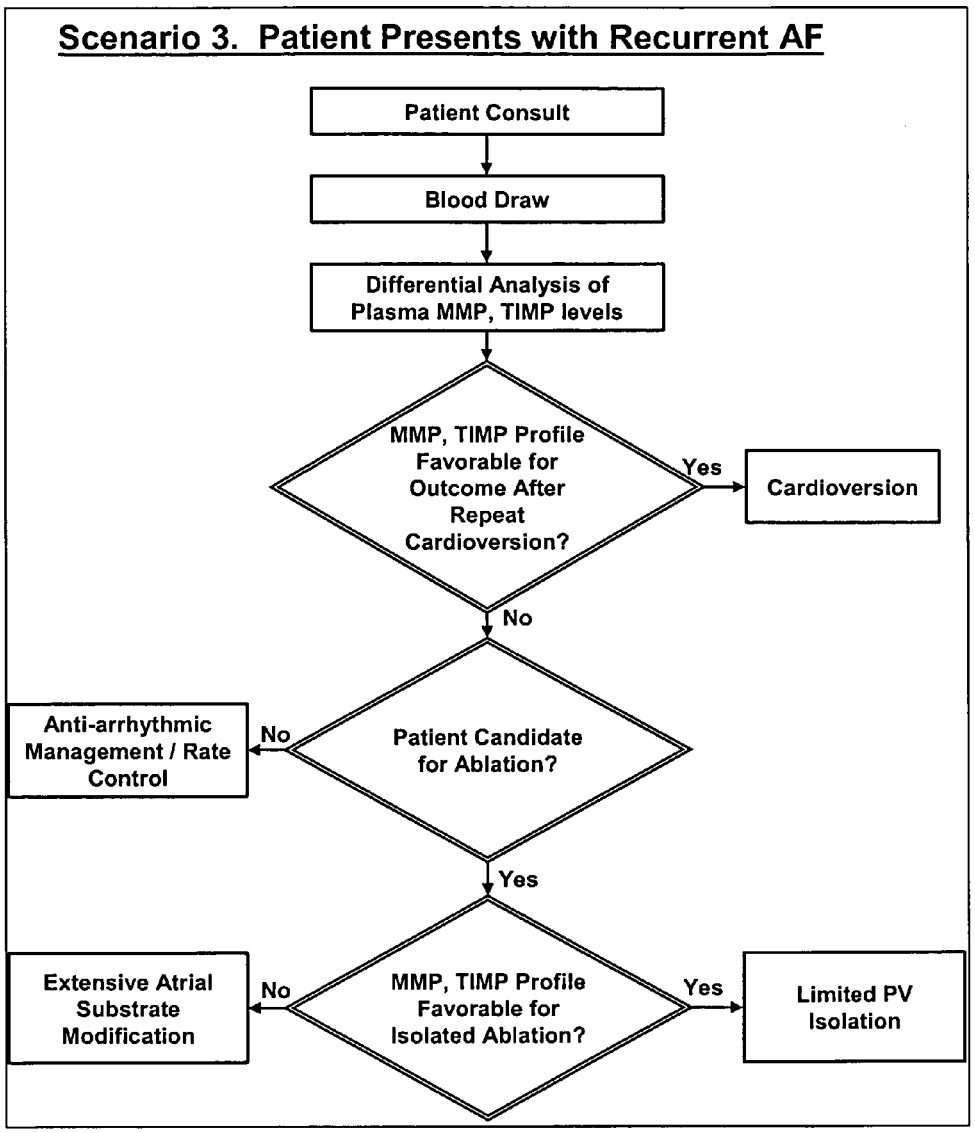

Thus, as shown in FIGS. 3 and 5, provided is a method of predicting the effectiveness of cardioversion for preventing recurrence of atrial fibrillation (AF), comprising measuring MMP and TIMP profiles in a body fluid from the subject and comparing the results to reference values. The patient can present with first or recurrent AF. When MMP and TIMP profiles are favorable, as disclosed herein, then the clinician can recommend cardioversion as a treatment modality. However, when MMP and TIMP profiles are not favorable, as disclosed herein, the clinician can prescribe an alternate therapy such as AF ablation or pharmacological management for rate control. The MMP and TIMP profiles can further be used to determine the effectiveness of isolated ablation such as pulmonary vein (PV) ostial ablation.

Figure 4:
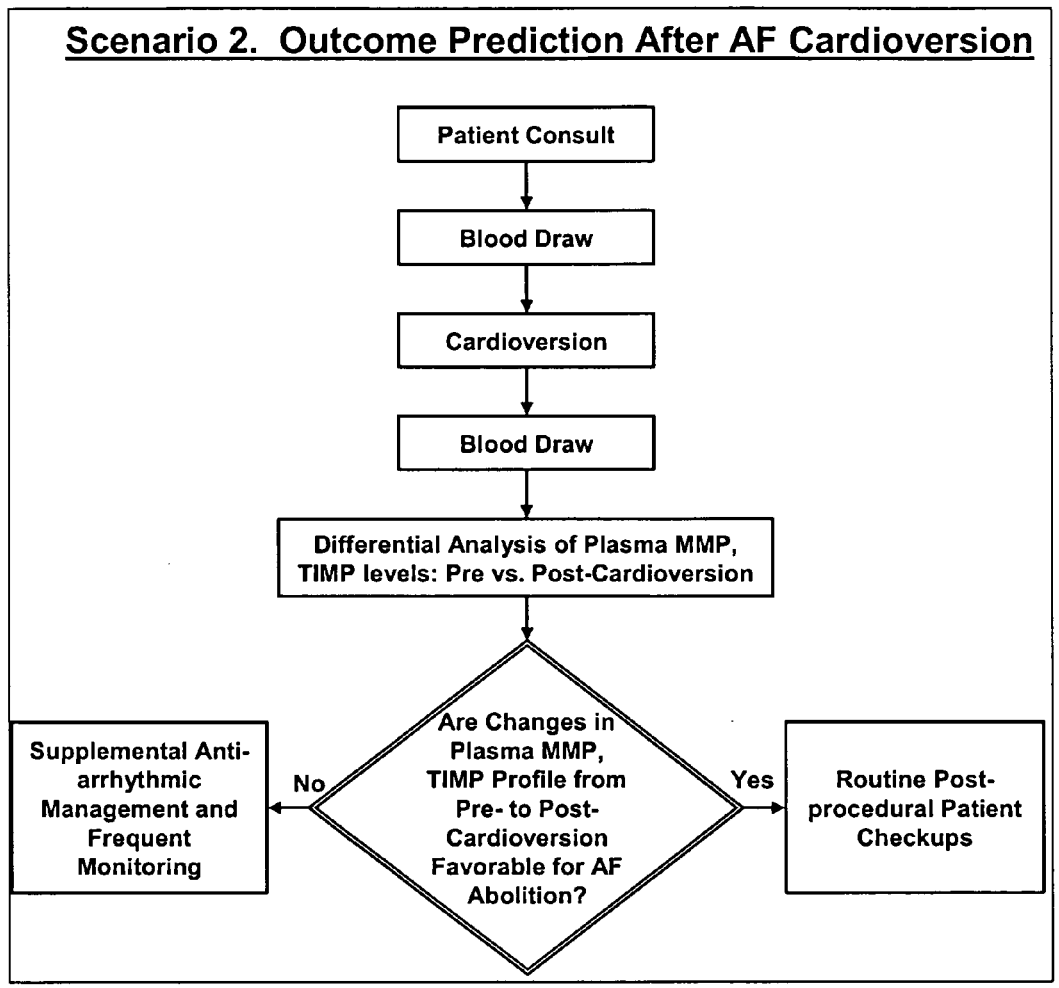

As shown in FIG. 4, provided is a method of determining the need for supplemental anti-arrhythmic management and/or frequent monitoring of a patient following a treatment modality such as cardioversion.

Figure 6:
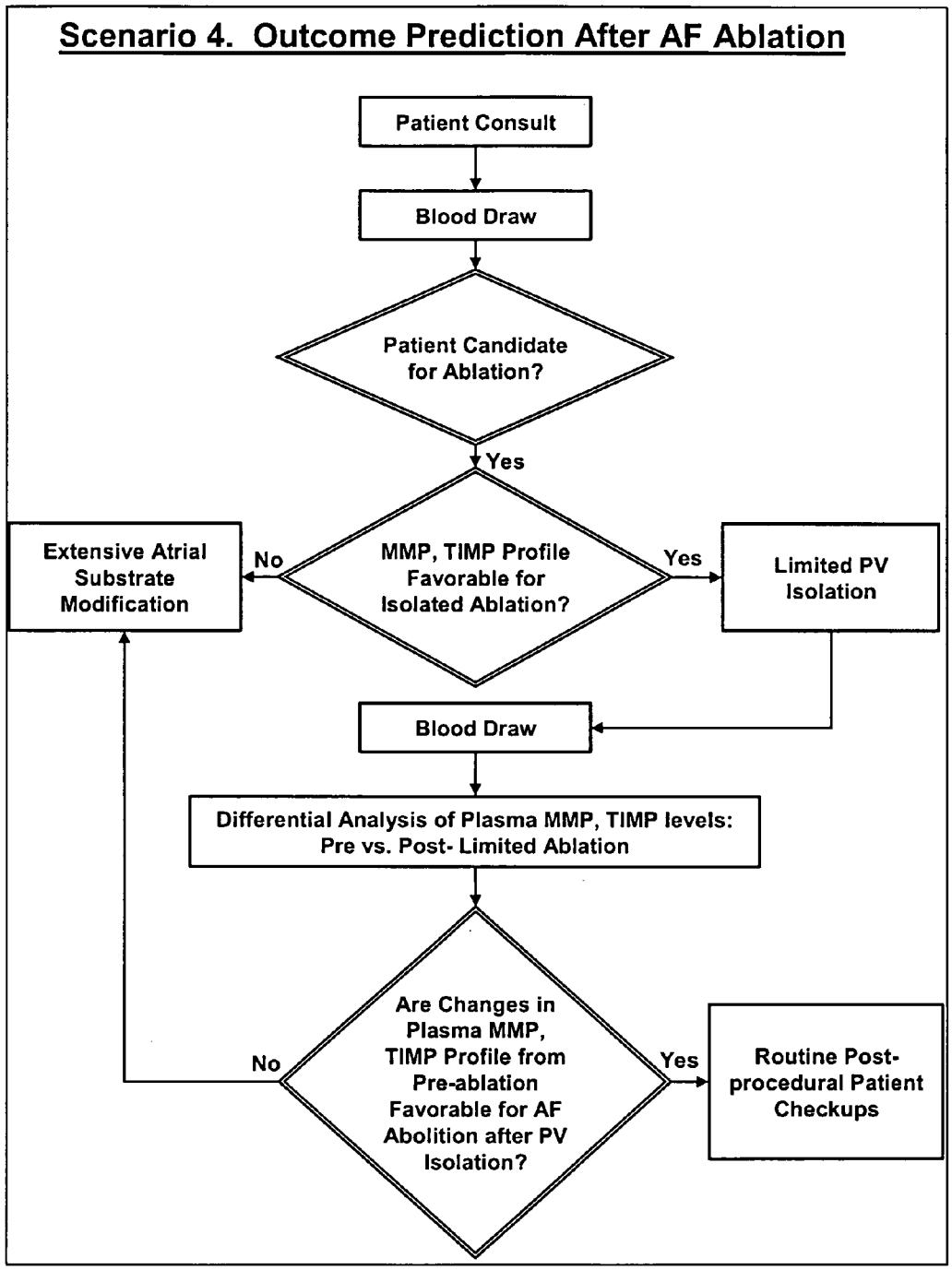

As shown in FIG. 6, also provided is a method of predicting the effectiveness of pulmonary vein (PV) ostial ablation for preventing recurrence of atrial fibrillation (AF), comprising measuring MMP and TIMP profiles in a body fluid from the subject and comparing the results to reference values.

The MMP/TIMP profiles are based on measurements of individual MMPs or TIMPs. The amounts of these can be measured by any means known to provide an acceptable indication of how much of any of these is present in the sample being analyzed. An example of a means of measuring is provided in the Examples. The process of measuring an amount of an analyte (e.g., MMP or TIMP) includes a measurement of no amount or an undetectable amount of the analyte. The techniques and approaches for measuring MMP and TIMPs which formed the basis of this method were based upon high sensitivity immunoassays. Several of these immunoassays were developed by this laboratory (i.e. TIMP-4 assay measurements).

Detection of the disclosed MMPs and TIMPs can be by enzyme linked immuno-assay (ELISA) means or other means. However, other more sensitive and rapid methods for measuring blood levels of MMPs and TIMPs have been performed and include the use of a multiplex assay system. In this example, multiple analytes in volume-limited samples, such as plasma or other biological samples, can be measured using a bead-based multiplex sandwich immunoassay. This emergent technique for multiplex analysis is built on technology that combines the sensitivity of ELISA with flow cytometric detection, allowing for the specific measurement of up to 100 different analytes within a single sample of less than 50 µl. This approach will allow for the measurement of multiple MMPs and TIMPs in a small blood sample. This type of approach can be used for the diagnostic, prognostic, predictive and therapeutic monitoring applications that are described herein. Specifically, to measure analyte concentrations simultaneously, the microbeads are incubated with sample (i.e. blood sample) and allowed to form complexes with the specific analytes of interest (i.e. MMPs). Detection antibodies (biotinylated), specific for a second epitope on each analyte, are then added to the mixture and allowed to bind to the microbeads complexed with analyte. The mixture is then incubated with a fluorescent reporter molecule (streptavidin-phycoerythrin) and the entire sample is passed through a two-laser flow cytometric detector. One laser detects the precise fluorescence of the microbead which defines the specific analyte being examined, and the other laser detects the amount of reporter fluorescence which is directly proportional to the amount of analyte bound. This process has been applied to a number of MMPs and other analytes that hold potential bearing to the CHF process. This is but one example of how single or multiple analytes can be measured with a very small blood sample. Other examples of measurements that have been performed with respect to MMP/TIMP analytes include radioimmunoassay and immunoblotting assays. These approaches are also antibody based.

Another example of a means for detecting MMPs and or TIMPs is the Bio-Plex® array system (BioRad, Hercules, Calif.). Also, multiplex kits for the Luminex (Austin, Tex.) platform can be used. For example the Luminex® 100 or 200 analyzers can be used. Yet another example that can be used is the LiquiChip® from Qiagen (Valencia, Calif.).

Thus provided are systems for predicting whether a subject with a history of atrial fibrillation will have recurrence of atrial fibrillation following a cardioversion procedure. Exemplary systems can comprise means for measuring at least one MMP level and/or at least one TIMP level from a body fluid from the subject. Such systems can further comprise a processing unit configured to produce an MMP, TIMP and/or MMP/TIMP profile based on the measured biomarker levels and to compare the at least biomarker level to a corresponding control biomarker level to determine the relative increase or decrease of each respective MMP level and/or TIMP level in the profile. The processing unit can be further configured to analyze the profile to determine whether the subject will have a recurrence of atrial fibrillation following the cardioversion procedure.

Exemplary systems for predicting whether a subject with a history of atrial fibrillation will have recurrence of atrial fibrillation following a cardioversion procedure can also comprise a processing unit configured to produce an MMP, TIMP, and/or MMP/TIMP profile based on the measured biomarker levels and to compare the at least one biomarker level to a corresponding control biomarker level to determine the relative increase or decrease of each respective measured MMP level or TIMP level, wherein the produced MMP profile, TIMP and/or MMP/TIMP profile is indicative of the likelihood of recurrence of atrial fibrillation in the subject.

Aspects of the exemplary systems disclosed herein can be implemented via a general-purpose computing device in the form of a computer. The components of the computer can include, but are not limited to, one or more processors or processing units, a system memory, and a system bus that couples various system components including the processor to the system memory.

The system bus can represent one or more of several possible types of bus structures, including a memory bus or memory controller, a peripheral bus, an accelerated graphics port, and a processor or local bus using any of a variety of bus architectures. By way of example, such architectures can include an Industry Standard Architecture (USA) bus, a Micro Channel Architecture (MCA) bus, an Enhanced ISA (EISA) bus, a Video Electronics Standards Association (VESA) local bus, and a Peripheral Component Interconnects (PCI) bus also known as a Mezzanine bus. This bus, and all buses specified in this description can also be implemented over a wired or wireless network connection. The bus, and all buses specified in this description can also be implemented over a wired or wireless network connection and each of the subsystems, including the processor, a mass storage device, an operating system, application software, data, a network adapter, system memory, an Input/Output Interface, a display adapter, a display device, and a human machine interface, can be contained within one or more remote computing devices at physically separate locations, connected through buses of this form, in effect implementing a fully distributed system.

The computer typically includes a variety of computer readable media. Such media can be any available media that is accessible by the computer and includes both volatile and non-volatile media, removable and non-removable media. The system memory can include computer readable media in the form of volatile memory, such as random access memory (RAM), and/or non-volatile memory, such as read only memory (ROM). The system memory typically contains data such as data and/or program modules such as operating system and application software that are immediately accessible to and/or are presently operated on by the processing unit. Application software can include biomarker detection and/or measurement, and analysis software.

The computer may also include other removable/non-removable, volatile/non-volatile computer storage media. By way of example, a mass storage device can provide non-volatile storage of computer code, computer readable instructions, data structures, program modules, and other data for the computer. For example, a mass storage device can be a hard disk, a removable magnetic disk, a removable optical disk, magnetic cassettes or other magnetic storage devices, flash memory cards, CD-ROM, digital versatile disks (DVD) or other optical storage, random access memories (RAM), read only memories (ROM), electrically erasable programmable read-only memory (EEPROM), and the like.

Any number of program modules can be stored on the mass storage device, including by way of example, an operating system and application software. Each of the operating system and application software (or some combination thereof) may include elements of the programming and the application software. Data can also be stored on the mass storage device. Data can be stored in any of one or more databases known in the art. Examples of such databases include, DB2®, Microsoft® Access, Microsoft® SQL Server, Oracle®, mySQL, PostgreSQL, and the like. The databases can be centralized or distributed across multiple systems.

A user can enter commands and information into the computer via an input device. Examples of such input devices include, but are not limited to, a keyboard, pointing device (e.g., a "mouse"), a microphone, a joystick, a serial port, a scanner, and the like. These and other input devices can be connected to the processing unit via a human machine interface that is coupled to the system bus, but may be connected by other interface and bus structures, such as a parallel port, game port, or a universal serial bus (USB).

In an exemplary system of an embodiment according to the present invention, the user interface can be chosen from one or more of the input devices listed above. Optionally, the user interface can also include various control devices such as toggle switches, sliders, variable resistors and other user interface devices known in the art. The user interface can be connected to the processing unit. It can also be connected to other functional portions of the exemplary system described herein in conjunction with or without connection with the processing unit connections described herein.

A display device can also be connected to the system bus via an interface, such as a display adapter. For example, a display device can be a monitor or an LCD (Liquid Crystal Display). In addition to the display device, other output peripheral devices can include components such as speakers (not shown) and a printer (not shown) which can be connected to the computer via an Input/Output Interface.

The computer can operate in a networked environment using logical connections to one or more remote computing devices. By way of example, a remote computing device can be a personal computer, portable computer, a server, a router, a network computer, a peer device or other common network node, and so on. Logical connections between the computer and a remote computing device can be made via a local area network (LAN) and a general wide area network (WAN). Such network connections can be through a network adapter. A network adapter can be implemented in both wired and wireless environments. Such networking environments are commonplace in offices, enterprise-wide computer networks, intranets, and the Internet. The remote computer may be a server, a router, a peer device or other common network node, and typically includes all or many of the elements already described for the computer. In a networked environment, program modules and data may be stored on the remote computer. The logical connections include a local area network ("LAN") and a wide area network ("WAN"). Other connection methods may be used, and networks may include such things as the "world wide web" or internet.

Application programs and other executable program components such as the operating system can reside at various times in different storage components of the computing device, and can be executed by the data processor(s) of the computer. An implementation of application software may be stored on or transmitted across some form of computer readable media. Computer readable media can be any available media that can be accessed by a computer. By way of example, and not limitation, computer readable media may comprise "computer storage media" and "communications media." Computer storage media include volatile and non-volatile, removable and non-removable media implemented in any method or technology for storage of information such as computer readable instructions, data structures, program modules, or other data. Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by a computer. An implementation of the disclosed method may be stored on or transmitted across some form of computer readable media.

The processing of the disclosed method and systems can be performed by software components. For example the processing of the detected biomarkers can be performed by software components. The disclosed methods and systems may thus be described in the general context of computer-executable instructions, such as program modules, being executed by one or more computers or other devices. Generally, program modules include computer code, routines, programs, objects, components, data structures, etc. that perform particular tasks or implement particular abstract data types. The disclosed method may also be practiced in grid-based and distributed computing environments where tasks are performed by remote processing devices that are linked through a communications network. In a distributed computing environment, program modules may be located in both local and remote computer storage media including memory storage devices.

Aspects of the exemplary systems and methods can be implemented in various forms including hardware, software, and a combination thereof. The hardware implementation can include any or a combination of the following technologies, which are all well known in the art: discrete electronic components, a discrete logic circuit(s) having logic gates for implementing logic functions upon data signals, an application specific integrated circuit having appropriate logic gates, a programmable gate array(s) (PGA), a field programmable gate array (FPGA), etc. The software can comprise an ordered listing of executable instructions for implementing logical functions, and can be embodied in any computer-readable medium for use by or in connection with an instruction execution system, apparatus, or device, such as a computer-based system, processor-containing system, or other system that can fetch the instructions from the instruction execution system, apparatus, or device and execute the instructions.

As described above, the computer can comprise software for the detection and analysis of biomarkers including MMPs and/or TIMPs. The software can comprise a computer-readable medium having computer readable program code for determining and or quantifying MMPs and/or TIMPs. Software can comprise program code to receive data from a detector device indicating presence and quantity of MMPs and TIMPs. The software can further comprise program code to determine MMP, TIMP and/or MMP/TIMP profile. Optionally, the software can determine likelihood of recurrence of AF based on the MMP, TIMP and/or MMP/TIMP profile.

C. KITS

Disclosed herein are kits that are drawn to reagents that can be used in practicing the methods disclosed herein. The kits can include any reagent or combination of reagents discussed herein or that would be understood to be required or beneficial in the practice of the disclosed methods. For example, disclosed is a kit for assessing a subject's risk for recurrence of AF, in which components include components described in the previous section. For example, the components of an MMP/TIMP kit would include the necessary reagents for complexing to the relevant MMP and/or TIMP of interest (See Table 2 for list of relevant MMPs and TIMPs) to a detection reagent. In the example of an immunoassay approach, a fluorescently labeled antibody against a specific MMP or TIMP would be incubated with the blood sample and following a washing and non-specific binding clearance step, the amount of antibody bound to the MMP or TIMP of interest would be computed by measuring the relative degree of fluorescence. This can be a very simple kit which could be used for screening, or a more complex system where multiple MMP/TIMPs are measured from a single sample. A rationale for a graduated approach for measuring one MMP or TIMP of interest to measuring multiple MMP/TIMPs simultaneously has been described in a previous section. For a screening assay (i.e. MMP-13) the small blood sample would be processed into plasma (centrifugation) and the plasma mixed with the MMP-13 targeted antibody. The mixture would be centrifuged again, and the specifically bound antibody bound to MMP-13 would be read by a fluorimetry system. This equipment and measurement system could be easily fashioned into a small suitcase or table top system. The readout from the system would then indicate whether MMP-13 is below or above a specific threshold measurement (as defined in a previous section).

D. EXAMPLES

1. Example 1

Atrial Fibrillation Associated with Differential Changes in Myocardial MMP and TIMP Levels The levels of MMPs and TIMPs were measured from the myocardium of explanted hearts of congestive heart failure (CHF) patients with and without AF. Since CHF can also alter the levels of MMPs and TIMPs, this study determined whether the presence of AF was associated with differential changes in myocardial MMP and TIMP levels. Myocardium from the walls of the right atrium (RA), right ventricle (RV), left atrium (LA), and left ventricle (LV) was obtained from explanted hearts of 43 end-stage CHF patients (pts). AF was present in 23 pts (duration: 1-84 months). The remaining 20 pts served as non-AF controls. The groups were well matched clinically, but LA size was increased in the AF cohort (5.5±0.8 vs. 4.9±0.7 cm, p<0.05). Myocardial collagen content and levels of MMPs-1, -2, -8, -9, -13, -14, and TIMPs-1, -2, -3, -4 were determined and expressed as a percentage of non-AF values (Table 2).

TABLE 2

Myocardial collagen content and levels of MMPs and TIMPs

| | RA | RV | LA | LV |
|---|---|---|---|---|
| MMP-1 | 139 ± 49* | 118 ± 45 | 121 ± 61 | 123 ± 68 |
| MMP-2 | 111 ± 48 | 96 ± 35 | 97 ± 37 | 106 ± 33 |
| MMP-8 | 70 ± 36* | 121 ± 96 | 99 ± 65 | 120 ± 48 |
| MMP-9 | 130 ± 99 | 112 ± 96 | 166 ± 123* | 113 ± 112 |
| MMP-13 | 107 ± 45 | 105 ± 51 | 103 ± 41 | 112 ± 39 |
| MMP-14 | 56 ± 26* | 122 ± 50 | 112 ± 126 | 108 ± 33 |
| TIMP-1 | 154 ± 141 | 161 ± 125* | 122 ± 94 | 100 ± 47 |
| TIMP-2 | 116 ± 82 | 110 ± 59 | 102 ± 90 | 138 ± 79* |
| TIMP-3 | 122 ± 89 | 141 ± 71* | 202 ± 194* | 134 ± 150* |
| TIMP-4 | 96 ± 13 | 100 ± 16 | 106 ± 15 | 99 ± 17 |
| Collagen | 171 ± 68* | 79 ± 41* | 155 ± 71* | 90 ± 13* |

Values presented as Mean ± SD
*p < 0.05 vs. non-AF values of 100%.

With AF, collagen content was higher within the atrial myocardium, but lower in the ventricular myocardium. There were chamber-specific differences in MMPs/TIMPs with AF. For example, MMP-1 in the RA and MMP-9 in the LA were higher with AF. TIMP-3 levels were higher in the RV, LA, and LV. In addition, LA collagen was positively correlated with AF duration (FIG. 1, r:0.49, p<0.03).

Therefore, AF is associated with chamber-specific alterations in myocardial collagen content and MMP/TIMP levels, indicative of differential remodeling and altered collagen metabolism. These findings formed the basis of this invention, in that plasma MMP/TIMP levels could be used as diagnostic/prognostic biomarkers and be used to direct clinical treatment of AF patients.

2. Example 2

Atrial Fibrillation and Cardioversion: Plasma Biomarkers for Prognosis, Diagnosis, and Prediction of Clinical Efficacy A study was performed to determine if plasma MMP-9 levels were altered in patients with AF. Blood was collected from 6 consecutive patients in whom an AF cardioversion procedure was scheduled. Plasma MMP-9 levels were determined by ELISA and these values were compared to values obtained from subjects with left ventricular (LV) hypertrophy without a history of AF (n=10). There were no significant differences between the AF and non-AF groups with respect to age (65±8 vs. 64±7 years), height (177±12 vs. 169±10 cm), weight (91±17 vs. 84±10 kg), or gender distribution (71% male). Left atrial (LA) diameter and LV end-diastolic dimension were significantly higher in the subjects with AF (LA: 4.4±0.4 vs. 3.3±0.5 cm, p<0.001; LV: 5.9±0.7 vs. 4.6±0.3 cm, p<0.001). However, LV ejection fraction (55±20 vs. 70±12%) and LV mass (echo: 244±60 vs. 297±29 g, p=0.08) were similar between groups. While plasma MMP-2 levels were similar (1183±278 vs. 1251±373 ng/mL), plasma MMP-9 levels were more than 3-fold higher in the AF group (80±54 vs. 22±14 ng/mL, p<0.01) compared with controls. Moreover, there was a significant correlation between LA diameter and plasma MMP-9 levels (y=36.8x−93.1, r=0.60, p=0.013).

Figure 2:
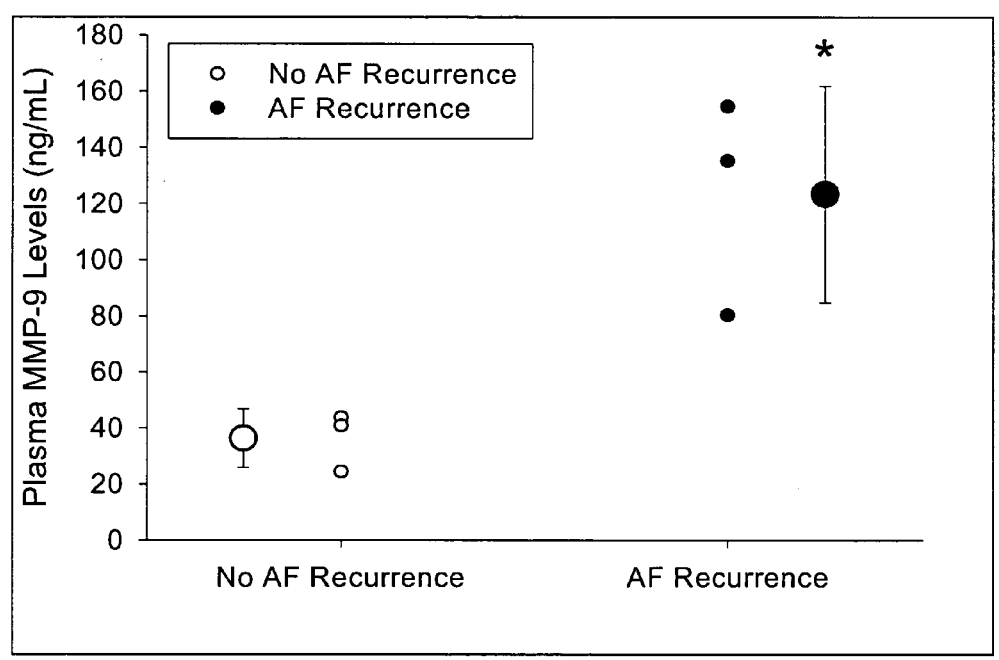

The patients who underwent cardioversion were followed for up to 1 month for AF recurrence. Within this follow-up period, AF was noted to have recurred in 3 of the 6 patients. Additional statistical tests were performed by dichotomizing based on AF recurrence. There were no differences with respect to LA size between the patients regardless of AF recurrence status. Pre-cardioversion plasma MMP-9 levels, however, were higher in the AF recurrence group than those in whom AF did not recur (FIG. 2).

Since AF recurs in approximately one-half of patients within 6-12 months in whom electrical cardioversion is attempted, there have been studies that attempted to examine predictors of cardioversion "failure". These studies included examination of patient's physical characteristics (age, height, weight, gender) (Van Gelder I C, et al. 1991), anatomical considerations with respect to changes in the dimensions of the left atria or left ventricular pump function (Van Gelder I C, et al. 1991; Sanfilippo A J, et al. 1990; Pozzoli M, et al. 1998; Psaty B M, et al. 1997), or changes in the plasma levels of certain biomarkers (B-type natriuretic peptide and C-reactive protein) (Lellouche N, et al. 2005; Wazni O, et al. 2005). Previous studies showed that younger age, smaller left atrial size, and shorter duration of AF prior to cardioversion are predictors of sinus rhythm maintenance following cardioversion (Van Gelder I C, et al. 1991). With respect to plasma biomarker predictors of AF, only B-type natriuretic peptide and the proinflammatory marker, C-reactive protein, were examined. For example, Lellouche et al. measured plasma B-type natriuretic peptide levels in 66 consecutive asymptomatic patients undergoing external cardioversion for AF (Lellouche N, et al. 2005). Twelve-lead electrocardiograms were obtained at 1 year. Sinus rhythm was maintained in 55% of patients. The independent predictors of the recurrence of atrial fibrillation at 1 year were a history of AF and plasma B-type natriuretic peptide (Lellouche N, et al. 2005).

It must be recognized that AF is associated with significant changes in the conformation and composition of the atrial extracellular matrix (Kostin S, et al. 2002; Ausma J, et al. 2001; Ausma J, et al. 1997; Boldt A, et al. 2004). While changes in the plasma levels of both B-type natriuretic peptide and C-reactive protein were associated with factors that could influence extracellular matrix composition, neither marker provides a more direct determination of extracellular matrix processes than the matrix metalloproteinases (MMPs) or the tissue inhibitors of the metalloproteinases (TIMPs).

Disclosed herein is the use of a set of biomarkers relevant to AF-associated changes in extracellular matrix composition and/or conformation.

Also disclosed is the combination of several biomarkers in a panel/profile to enhance sensitivity and selectivity (i.e. predictive accuracy) of the prognostic ability of this strategy.

Also provided is a means to direct clinical management of AF patients with respect to rate or rhythm control, as well as the aggressiveness to pursue various therapeutic curative ablation strategies.

There are several possible implementation scenarios for the disclosed methods. For example, plasma MMP and TIMP levels can be used to 1) determine treatment regimen of a patient presenting with AF, 2) predict possible outcome following electrical cardioversion for AF, 3) determine continued treatment modalities in patient with recurrent AF, and 4) specify extent of AF ablation procedure needed and prognosticate success of AF ablation. The implementation for each of these scenarios, in flow chart format, is presented in FIGS. 3 through 6, respectively.

The scope of the following material is to provide methodological information to support the claim that a specific and significant plasma profile of matrix metalloproteinases (MMPs) and tissue inhibitors of MMPs (TIMPs) occur in patients with atrial fibrillation and that a specific algorithm for differentiating this profile from patients who are refractory to electrical cardioversion of atrial fibrillation is provided herein. First, in Table 3, a clear set of normal values for human subjects within the age range and across genders is provided. Stoichiometric ratios for MMP/TIMP profiles are provided which hold important diagnostic and prognostic information. These data were collected and analyzed from over 100 subjects.

TABLE 3

Normal Human* Reference Ranges

| MMP/TIMP Plasma Levels (ng/mL) | |
|---|---|
| MMP-2 | 1000-1500 |
| MMP-9 | 0-20 |
| MMP-7 | 0-5 |
| MMP-13 | 0-10 |
| MMP-8 | 0-3 |
| TIMP-1 | 800-1000 |
| TIMP-2 | 25-50 |
| TIMP-4 | 0-2 |
| MMP-9/TIMP Ratios | |
| MMP-9/TIMP-1 | 7-15 |
| MMP-9/TIMP-2 | 100-500 |
| MMP-9/TIMP-4 | 1-10 |

*Normal Adults Age 25-70 years

Table 4 presents MMP-2 and MMP-9 values in absolute terms for AF patients. These values were collected as described above. A unique plasma profile is demonstrated. This unique profile includes no change in plasma MMP-2 values when compared to suitable controls, and increased MMP-9 plasma levels in atrial fibrillation patients when compared to suitable controls. Moreover, differentially increased plasma MMP-9 levels were predictive of AF patients who were refractory to electrical cardioversion and those who are not.

TABLE 4

Diagnostic for Atrial Fibrillation

| MMP/TIMP Plasma Levels (ng/mL) | |
|---|---|
| MMP-2 | 500-2000 |
| MMP-9 | >25 |

TABLE 4-continued

Diagnostic for Atrial Fibrillation

| Percent Changes in MMP Plasma Levels | |
|---|---|
| MMP-2 | (−50)-(+50) |
| MMP-9 | 150-500 |

The disclosed plasma signature provides for the first time an ability to differentiate between atrial fibrillation patients that are likely to be refractory to electrical cardioversion of atrial fibrillation. Specifically, as shown in Table 5, a unique and very different plasma profile emerges from an AF patient at risk for being refractory to electrical cardioversion for atrial fibrillation. Thus, differential diagnoses can be made on these profiles and more importantly more specific clinical decision making and therapeutic strategies considered.

TABLE 5

Differential Diagnosis of Atrial Fibrillation
Patients Refractory to Conversion of Atrial Fibrillation
Through Electrical Cardioversion

| | Non-Refractory | | Refractory | |
|---|---|---|---|---|
| Plasma MMP/TIMP Profiles (ng/ml) | | | | |
| MMP-2 | ↔ | (◇1250) | ↔ | (◇1250) |
| MMP-9 | ↑ | (>20) | ↑↑ | (>40) |
| MMP-13 | ↔ | (<10) | ↓ | (<5) |
| MMP-8 | ↔ | (<3) | ↓ | (<2) |
| TIMP-1 | ↑ | (>1100) | ↑↑ | (>1500) |
| TIMP-2 | ↑ | (>50) | ↑↑ | (>75) |
| TIMP-4 | ↓ | (<2) | ↑↑ | (>5) |
| Plasma MMP/TIMP Ratios | | | | |
| MMP-9/TIMP-1 (×10³) | ↑ | (>15) | ↓ | (<7) |
| MMP-9/TIMP-2 (×10³) | ↑ | (>500) | ↓ | (<100) |
| MMP-9/TIMP-4 | ↑ | (>10) | ↓ | (<1) |

3. Example 3

Relationship Between Myocardial and Plasma Levels of MMPs

Figure 7:
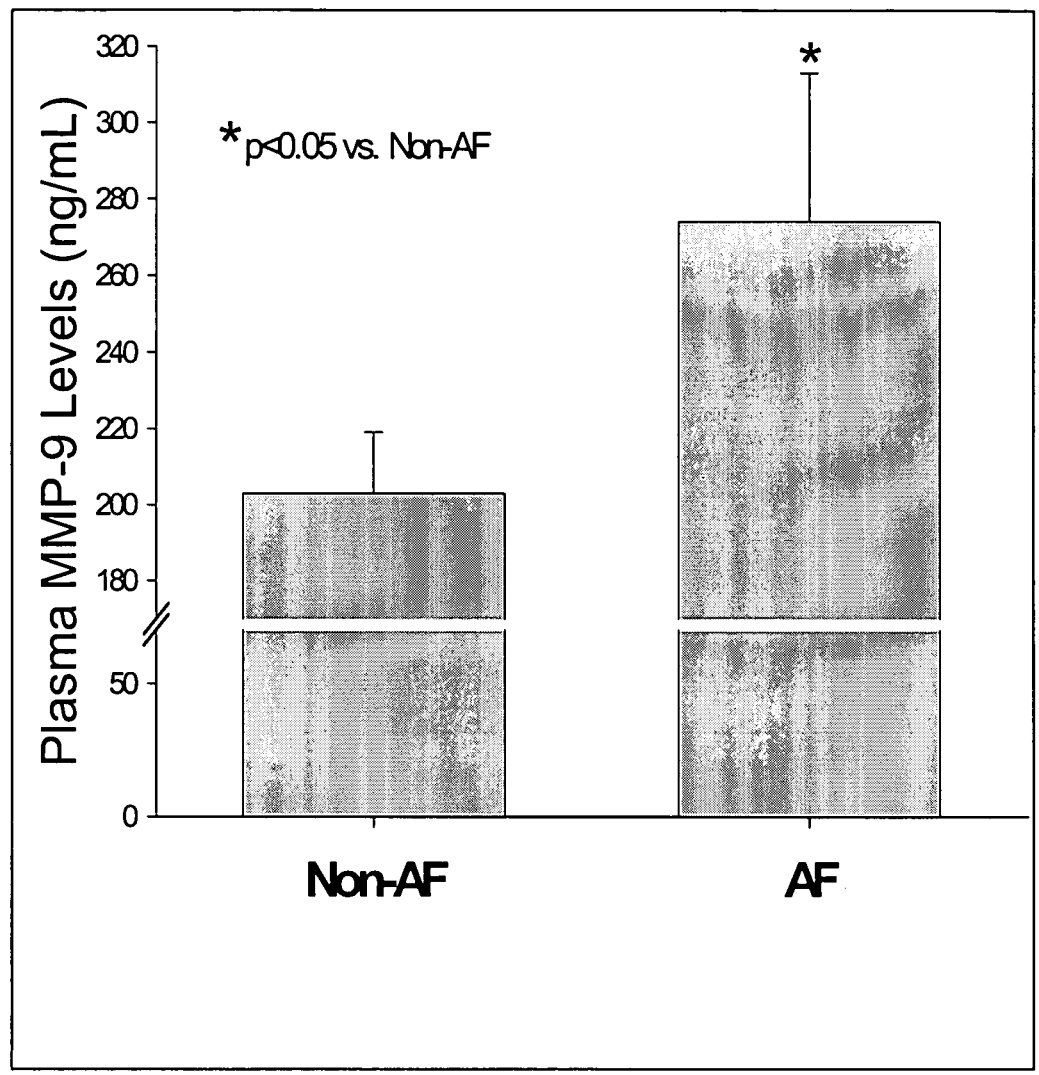
Figure 8:
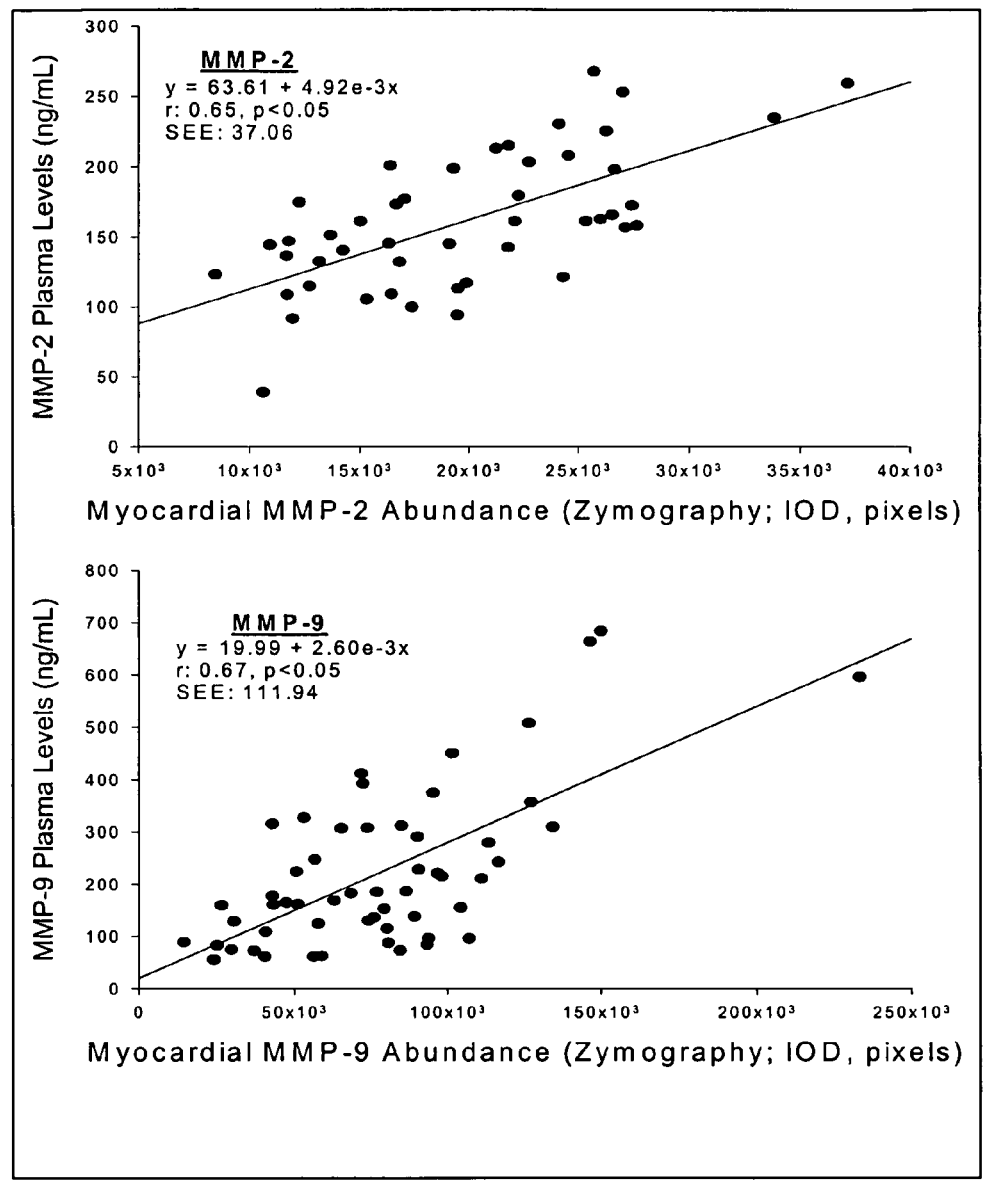

A number of pathological conditions—not limited to cardiovascular conditions—and/or pharmacological regimens are associated with alterations in plasma MMP levels. Therefore, a study was performed to determine whether there was a relationship between myocardial and plasma MMP levels. Preoperative plasma samples and the portion of the right atrial appendage that was clinically removed for cannulation were obtained from patients undergoing elective open heart surgical procedures. The plasma and the myocardial samples were analyzed for MMP-2 and MMP-9 levels using the Luminex multiplex assay and zymography, respectively. Two important findings from study include: First plasma levels of MMP-9 in subjects with a history of preoperative AF (n=24) were higher than those without AF (n=57, FIG. 7), whereas plasma MMP-2 levels were similar (165±10 vs. 153±6 ng/mL, p=0.63). Second, there were linear relationships between plasma and myocardial levels of MMP-2 and MMP-9 (FIG. 8, both p<0.05). These findings show the differential effect of the presence of AF on plasma MMP-2 and MMP-9 levels in this cohort of patients presenting for cardiac surgery was similar to those determined in a separate cohort of non-surgical subjects with hypertension. This finding demonstrates the ability to use plasma MMP levels as discriminant biomarkers for detection of AF. Second, the association between myocardial and plasma levels of these MMP subtypes indicate that the changes that occur within the myocardium with respect to MMP abundance are reflected as directional changes in the plasma levels of the same MMPs.

E. REFERENCES

Aime-Sempe C, Folliguet T, Rucker-Martin C, Krajewska M, Krajewski S, Heimburger M, Aubier M, Mercadier J J, Reed J C, Hatem S N. Myocardial cell death in fibrillating and dilated human right atria. Journal of the American College of Cardiology. 1999; 34:1577-1586.

Allessie M, Ausma J, Schotten U. Electrical, contractile and structural remodeling during atrial fibrillation. Cardiovasc Res. 2002; 54:230-246.

Allessie M A, Boyden P A, Camm A J, Kleber A G, Lab M J, Legato M J, Rosen M R, Schwartz P J, Spooner P M, Van Wagoner D R, Waldo A L. Pathophysiology and prevention of atrial fibrillation. Circulation. 2001; 103:769-777.

Ausma J, Litjens N, Lenders M H, Duimel H, Mast F, Wouters L, Ramaekers F, Allessie M, Borgers M. Time course of atrial fibrillation-induced cellular structural remodeling in atria of the goat. J Mol Cell Cardiol. 2001; 33:2083-2094.

Ausma J, van der Velden H M, Lenders M H, van Ankeren E P, Jongsma H J, Ramaekers F C, Borgers M, Allessie M A. Reverse structural and gap junctional remodeling after prolonged atrial fibrillation in the goat. Circulation. 2003; 107:2051-2058.

Ausma J, Wijffels M, Thone F, Wouters L, Allessie M, Borgers M. Structural changes of atrial myocardium due to sustained atrial fibrillation in the goat. Circulation. 1997; 96:3157-3163.

Benjamin E J, Wolf P A, D'Agostino R B, Silbershatz H, Kannel W B, Levy D. Impact of atrial fibrillation on the risk of death: the Framingham Heart Study. Circulation. 1998; 98:946-952.

Benjamin E J, Wolf P A, Kannel W B. The epidemiology of atrial fibrillation. In: Atrial fibrillation: mechanisms and management. Falk R H, Podrid P J, eds. 1997. Lippincott-Raven Publishers, Philadelphia.

Blankenberg S, Rupprecht H J, Poirier O, Bickel C, Smieja M, Hafner G, Meyer J, Cambien F, Tiret L, for the Athero-Gene Investigators. Plasma Concentrations and Genetic Variation of Matrix Metalloproteinase 9 and Prognosis of Patients With Cardiovascular Disease. Circulation. 2003; 107:1579.

Boldt A, Wetzel U, Lauschke J, Weigl J, Gummert J, Hindricks G, Kottkamp H, Dhein S. Fibrosis in left atrial tissue of patients with atrial fibrillation with and without underlying mitral valve disease. Heart. 2004; 90:400-405.

Bollmann A, Mende M, Neugebauer A, Pfeiffer D. Atrial fibrillatory frequency predicts atrial defibrillation threshold and early arrhythmia recurrence in patients undergoing internal cardioversion of persistent atrial fibrillation. Pacing Clin Electrophysiol. 2002; 25:1179-1184.

Brundel B J J M, Henning R H, Kampinga H H, Van Gelder I C, Crijns H J G M. Molecular mechanisms of remodeling in human atrial fibrillation. Cardiovascular Research. 2002; 54:315-324.

Deisenhofer I, Schneider M A E, Bohlen-Knauf M, Zrenner B, Ndrepepa G, Schmieder S, Weber S, Schreieck Ju, Weyerbrock S, Schmitt C. Circumferential mapping and electric isolation of pulmonary veins in patients with atrial fibrillation. The American Journal of Cardiology. 2003; 91:159-163.

Deschamps A M, Spinale F G. Pathways of matrix metalloproteinase induction in heart failure: Bioactive molecules and transcriptional regulation. Cardiovasc Res. 2006; 69:666-676.

Dispersyn G D, Ausma J, Thone F, Flameng W, Vanoverschelde J L, Allessie M A, Ramaekers F C, Borgers M. Cardiomyocyte remodelling during myocardial hibernation and atrial fibrillation: prelude to apoptosis. Cardiovasc Res. 1999; 43:947-957.

Etoh T, Joffs C, Deschamps A M, Davis J, Dowdy K, Hendrick J, Baicu S, Mukherjee R, Manhaini M, Spinale F G. Myocardial and interstitial matrix metalloproteinase activity after acute myocardial infarction in pigs. Am J Physiol Heart Circ Physiol. 2001; 281:H987-H994.

Fragakis N, Shakespeare C F, Lloyd G, Simon R, Bostock J, Holt P, Gill J S. Reversion and maintenance of sinus rhythm in patients with permanent atrial fibrillation by internal cardioversion followed by biatrial pacing. Pacing Clin Electrophysiol. 2002; 25:278-286.

Frick M, Frykman V, Jensen-Urstad M, Ostergren J, Rosenqvist M. Factors predicting success rate and recurrence of atrial fibrillation after first electrical cardioversion in patients with persistent atrial fibrillation. Clin Cardiol. 2001; 24:238-244.

Frustaci A, Chimenti C, Bellocci F, Morgante E, Russo M A, Maseri A. Histological Substrate of Atrial Biopsies in Patients With Lone Atrial Fibrillation. Circulation. 1997; 96:1180-1184.

Goette A, Arndt M, Rocken C, Staack T, Bechtloff R, Reinhold D, Huth C, Ansorge S, Klein H U, Lendeckel U. Calpains and cytokines in fibrillating human atria. Am J Physiol Heart Circ Physiol. 2002; 283:H264-H272.

Hirohata S, Kusachi S, Murakami M, Murakami T, Sano I, Watanabe T, Komatsubara I, Kondo J, Tsuji T. Time dependent alterations of serum matrix metalloproteinase-1 and metalloproteinase-1 tissue inhibitor after successful reperfusion of acute myocardial infarction. Heart. 1997; 78:278-284.

Hobbs W J, Fynn S, Todd D M, Wolfson P, Galloway M, Garratt C J. Reversal of atrial electrical remodeling after cardioversion of persistent atrial fibrillation in humans. Circulation. 2000; 101:1145-1151.

Kai H, Ikeda H, Yasukawa H, Kai M, Seki Y, Kuwahara F, Ueno T, Sugi K, Imaizumi T. Peripheral blood levels of matrix metalloproteases-2 and -9 are elevated in patients with acute coronary syndromes. J Am Coll Cardiol. 1998; 32:368-372.

Kostin S, Klein G, Szalay Z, Hein S, Bauer E P, Schaper J. Structural correlate of atrial fibrillation in human patients. Cardiovascular Research. 2002; 54:361-379.

Lellouche N, Berthier R, Mekontso-Dessap A, Braconnier F, Monin J L, Duval A M, Dubois-Rande J L, Gueret P, Garot J. Usefulness of plasma B-type natriuretic peptide in predicting recurrence of atrial fibrillation one year after external cardioversion. Am J Cardiol. 2005; 95:1380-1382.

Lin J M, Lin J L, Lai L P, Tseng Y Z, Stephen Huang S K. Predictors of clinical recurrence after successful electrical cardioversion of chronic persistent atrial fibrillation: clinical and electrophysiological observations. Cardiology. 2002; 97:133-137.

Marin F, Roldan V, Climent V, Garcia A, Marco P, Lip G Y H. Is Thrombogenesis in Atrial Fibrillation Related to Matrix Metalloproteinase-1 and Its Inhibitor, TIMP-1? Stroke. 2003; 34:1181.

Matrisian L M. Metalloproteinases and their inhibitors in matrix remodeling. Trends in Genetics. 1990; 6:121-125.

Montaner J, Alvarez-Sabin J, Molina C, Angles A, Abilleira S, Arenillas J, Gonzalez M A, Monasterio J. Matrix Metalloproteinase Expression After Human Cardioembolic Stroke: Temporal Profile and Relation to Neurological Impairment. Stroke. 2001; 32:1759-1766.

Montaner J, Alvarez-Sabin J, Molina C A, Angles A, Abilleira S, Arenillas J, Monasterio J. Matrix Metalloproteinase Expression Is Related to Hemorrhagic Transformation After Cardioembolic Stroke. Stroke. 2001; 32:2762-2767.

Montaner J, Molina C A, Monasterio J, Abilleira S, Arenillas J F, Ribo M, Quintana, M, Alvarez-Sabin J. Matrix Metalloproteinase-9 Pretreatment Level Predicts Intracranial Hemorrhagic Complications After Thrombolysis in Human Stroke. Circulation. 2003; 107:598-603.

Pozzoli M, Cioffi G, Traversi E, Pinna G D, Cobelli F, Tavazzi L. Predictors of primary atrial fibrillation and concomitant clinical and hemodynamic changes in patients with chronic heart failure: a prospective study in 344 patients with baseline sinus rhythm. J Am Coll Cardiol. 1998; 32:197-204.

Psaty B M, Manolio T A, Kuller L H, Kronmal R A, Cushman M, Fried L P, White R, Furberg C D, Rautaharju P M. Incidence of and risk factors for atrial fibrillation in older adults. Circulation. 1997; 96:2455-2461.

Sanfilippo A J, Abascal V M, Sheehan M, Oertel L B, Harrigan P, Hughes R A, Weyman A E. Atrial enlargement as a consequence of atrial fibrillation. A prospective echocardiographic study. Circulation. 1990; 82:792-797.

Schotten U, Ausma J, Stelibrink C, Sabatschus I, Vogel M, Frechen D, Schoendube F, Hanrath P, Allessie M A. Cellular mechanisms of depressed atrial contractility in patients with chronic atrial fibrillation. Circulation. 2001; 103:691-698.

Schotten U, Duytschaever M, Ausma J, Eijsbouts S, Neuberger H R, Allessie M. Electrical and contractile remodeling during the first days of atrial fibrillation go hand in hand. Circulation. 2003; 107:1433-1439.

Thijssen V L J L, Ausma J, Borgers M. Structural remodelling during chronic atrial fibrillation: act of programmed cell survival. Cardiovascular Research. 2001; 52:14-24.

Todd D M, Fynn S P, Hobbs W J, Fitzpatrick A P, Garratt C J. Prevalence and significance of focal sources of atrial arrhythmia in patients undergoing cardioversion of persistent atrial fibrillation. J Cardiovasc Electrophysiol. 2000; 11:616-622.

Van Gelder I C, Crijns H J, van Gilst W H, Verwer R, Lie K I. Prediction of uneventful cardioversion and maintenance of sinus rhythm from direct-current electrical cardioversion of chronic atrial fibrillation and flutter. Am J. Cardiol. 1991; 68:41-46.

Visse R, Nagase H. Matrix metalloproteinases and tissue inhibitors of metalloproteinases: structure, function, and biochemistry. Circ Res. 2003; 92:827-839.

Wazni O, Martin D O, Marrouche N F, Shaaraoui M, Chung M K, Almahameed S, Schweikert R A, Saliba W I, Natale A. C reactive protein concentration and recurrence of atrial fibrillation after electrical cardioversion. Heart. 2005; 91:1303-1305.

Wyse D G, Waldo A L, DiMarco J P, et al. The Atrial Fibrillation Follow-up Investigation of Rhythm Management (AFFIRM) Investigators. A Comparison of Rate Control and Rhythm Control in Patients with Atrial Fibrillation. N Engl J Med. 2002; 347:1825-1833.

Yu W C, Lee S H, Tai C T, Tsai C F, Hsieh M H, Chen C C, Ding Y A, Chang M S, Chen S A. Reversal of atrial electrical remodeling following cardioversion of long-standing atrial fibrillation in man. Cardiovascular Research. 1999; 42:470-476.

What is claimed is:

1. A method for predicting whether a subject with a history of atrial fibrillation will have recurrence of atrial fibrillation following a cardioversion procedure, comprising:
   measuring at least one MMP level in a body fluid from the subject to produce an MMP profile; and
   using the MMP profile to determine whether the subject will have a recurrence of atrial fibrillation following the cardioversion procedure.

2. A method for predicting whether a subject with a history of atrial fibrillation will have recurrence of atrial fibrillation following a cardioversion procedure, comprising:
   measuring at least one MMP level in a body fluid from the subject to produce an MMP profile; and
   using the MMP profile to determine whether the subject will have a recurrence of atrial fibrillation following the cardioversion procedure,
   wherein the use of the MMP profile comprises comparing a least one measured MMP level of the profile to at least one corresponding control MMP level to determine the relative increase or decrease of each respective MMP level to the control MMP level.

3. A method for predicting whether a subject with a history of atrial fibrillation will have recurrence of atrial fibrillation following a cardioversion procedure, comprising:
   measuring at least one MMP level in a body fluid from the subject to produce an MMP profile; and
   using the MMP profile to determine whether the subject will have a recurrence of atrial fibrillation following the cardioversion procedure,
   wherein the MMP profile comprises measurements of levels of a plurality of MMPs.

4. The method of claim 3, further comprising treating the subject with an implantable pacer device.

5. The method of claim 3, further comprising treating the subject with pharmacological rate control.

6. The method of claim 3, further comprising treating the subject by ablating heart tissue to alter abnormal electrical pathways in the heart tissue.

7. A method for predicting whether a subject with a history of atrial fibrillation will have recurrence of atrial fibrillation following a cardioversion procedure, comprising:
   measuring at least one MMP level in a body fluid from the subject to produce an MMP profile; and
   using the MMP profile to determine whether the subject will have a recurrence of atrial fibrillation following the cardioversion procedure,
   wherein the MMP profile indicates that the subject is not likely to have a recurrence of atrial fibrillation following the cardioversion procedure.

8. The method of claim 7, further comprising treating the subject with electrical cardioversion.

9. A method for predicting whether a subject with a history of atrial fibrillation will have recurrence of atrial fibrillation following a cardioversion procedure, comprising:
   measuring at least one MMP level in a body fluid from the subject to produce an MMP profile; and
   using the MMP profile to determine whether the subject will have a recurrence of atrial fibrillation following the cardioversion procedure,
   wherein the MMP profile comprises measurements of an amount of MMP-9, MMP-8, or MMP-13, or a combination thereof.

10. The method of claim 9, wherein an amount of MMP-9 greater than 40 ng/ml or an amount of MMP-13 less than 5 ng/mL, or a combination thereof, is an indication that the subject will have a recurrence of atrial fibrillation following the cardioversion procedure.

11. The method of claim 9, wherein an amount of MMP-9 that is at least about 50% greater than a control value or wherein an amount of MMP-13 is undetectable, or a combination thereof, is an indication that the subject will have a recurrence of atrial fibrillation following the cardioversion procedure.

12. A method for predicting whether a subject with a history of atrial fibrillation will have recurrence of atrial fibrillation following a cardioversion procedure, comprising:
measuring at least one TIMP level in a body fluid from the subject to produce a TIMP profile; and
using the TIMP profile to determine whether the subject will have a recurrence of atrial fibrillation following the cardioversion procedure.

13. The method of claim 12, wherein the use of the TIMP profile comprises comparing at least one measured TIMP level to at least one corresponding control TIMP level to determine the relative increase or decrease of each respective TIMP level compared to the control TIMP level.

14. The method of claim 12, wherein the TIMP profile comprises measurements of levels of a plurality of TIMPs.

15. The method of claim 14, further comprising treating the subject with an implantable pacer device.

16. The method of claim 14, further comprising treating the subject with pharmacological rate control.

17. The method of claim 14, further comprising treating the subject by ablating heart tissue to alter abnormal electrical pathways in the heart tissue.

18. The method of claim 12, wherein the TIMP profile indicates that the subject is not likely to have a recurrence of atrial fibrillation following the cardioversion procedure.

19. The method of claim 12, further comprising treating the subject with electrical cardioversion.

20. The method of claim 12, wherein the TIMP profile comprises measurements of an amount of TIMP-1, TIMP-2, or TIMP-4, or combinations thereof.

21. The method of claim 20, wherein an amount of TIMP-1 greater than 1500 ng/mL, an amount of TIMP-2 greater than 75 ng/mL, or an amount of TIMP-4 greater than 5 ng/mL, or a combination thereof, is an indication that the subject will have a recurrence of atrial fibrillation following the cardioversion procedure.

22. The method of claim 20, wherein an amount of TIMP-1 that is at least about 50% greater than a control value, an amount of TIMP-2 that is at least about 50% greater than a control value, or an amount of TIMP-4 that is at least about 50% greater than a control value, or combinations thereof, is an indication that the subject will have a recurrence of atrial fibrillation following the cardioversion procedure.

23. A method for predicting whether a subject with a history of atrial fibrillation will have recurrence of atrial fibrillation following a cardioversion procedure, comprising:
measuring at least one MMP level and at least one TIMP level in a body fluid from the subject to produce an MMP/TIMP profile; and
using the MMP/TIMP profile to determine whether the subject will have a recurrence of atrial fibrillation following the cardioversion procedure.

24. The method of claim 23, wherein the use of the MMP/TIMP profile comprises comparing at least one measured MMP and at least one TIMP level to at least one corresponding control MMP and TIMP level to determine the relative increase or decrease of each respective MMP and TIMP level compared to the control MMP and TIMP level.

25. The method of claim 23, wherein the MMP/TIMP profile comprises measurements of the levels of a plurality of MMPs and TIMPs.

26. The method of claim 25, further comprising treating the subject with an implantable pacer device.

27. The method of claim 25, further comprising treating the subject with pharmacological rate control.

28. The method of claim 25, further comprising treating the subject by ablating heart tissue to alter abnormal electrical pathways in the heart tissue.

29. The method of claim 23, wherein the MMP/TIMP profile indicates that the subject is not likely to have a recurrence of atrial fibrillation following the cardioversion procedure.

30. The method of claim 29, further comprising treating the subject with electrical cardioversion.

31. The method of claim 23, wherein the MMP/TIMP profile comprises measurements of an amount of MMP-9, MMP-8, MMP-13, TIMP-2, or TIMP-4, or a combination thereof.

32. The method of claim 31, wherein an amount of MMP-9 greater than 40 ng/ml, an amount of MMP-13 less than 5 ng/mL, an amount of TIMP-1 greater than 1500 ng/mL, an amount of TIMP-2 greater than 75 ng/mL, or an amount of TIMP-4 greater than 5 ng/mL, or a combination thereof, is an indication that the subject will have a recurrence of atrial fibrillation following the cardioversion procedure.

33. The method of claim 31, wherein an amount of MMP-9 that is at least about 50% greater than a control value, wherein an amount of MMP-13 that is undetectable, an amount of TIMP-1 that is at least about 50% greater than a control value, an amount of TIMP-2 that is at least about 50% greater than normal value, or an amount of TIMP-4 that is at least about 50% greater than normal value, or combinations thereof, is an indication that the subject will have a recurrence of atrial fibrillation following the cardioversion procedure.

34. A method for determining whether a subject with a history of atrial fibrillation should be treated with an implantable pacer, comprising:
measuring at least one MMP level and at least one TIMP level in a body fluid from the subject to produce an MMP/TIMP profile; and
using the MMP/TIMP profile to determine whether the subject will have a recurrence of atrial fibrillation following a cardioversion procedure, a likely recurrence of atrial fibrillation indicating treatment with an implantable pacer.

35. A method for determining whether a subject with a history of atrial fibrillation should be treated with an implantable pacer, comprising:
measuring at least one MMP level in a body fluid from the subject to produce an MMP profile; and
using the MMP profile to determine whether the subject will have a recurrence of atrial fibrillation following a cardioversion procedure, a likely recurrence of atrial fibrillation indicating treatment with an implantable pacer.

36. A method for determining whether a subject with a history of atrial fibrillation should be treated with an implantable pacer, comprising:
measuring at least one TIMP level in a body fluid from the subject to produce a TIMP profile; and
using the TIMP profile to determine whether the subject will have a recurrence of atrial fibrillation following a cardioversion procedure, a likely recurrence of atrial fibrillation indicating treatment with an implantable pacer.

37. A method for determining whether a subject with a history of atrial fibrillation should be treated with pharmacological rate control, comprising:
  measuring at least one MMP level and at least one TIMP level in a body fluid from the subject to produce an MMP/TIMP profile; and
  using the MMP/TIMP profile to determine whether the subject will have a recurrence of atrial fibrillation following a cardioversion procedure, a likely recurrence of atrial fibrillation indicating treatment with pharmacological rate control.

38. A method for determining whether a subject with a history of atrial fibrillation should be treated with ablation, comprising:
  measuring at least one MMP level and at least one TIMP level in a body fluid from the subject to produce an MMP/TIMP profile; and
  using the MMP/TIMP profile to determine whether the subject will have a recurrence of atrial fibrillation following a cardioversion procedure, a likely recurrence of atrial fibrillation indicating treatment with ablation.

39. A method for determining whether a subject with a history of atrial fibrillation should be treated with cardioversion, comprising:
  measuring at least one MMP level and at least one TIMP level in a body fluid from the subject to produce an MMP/TIMP profile; and
  using the MMP/TIMP profile to determine whether the subject will have a recurrence of atrial fibrillation following a cardioversion procedure, an unlikely recurrence of atrial fibrillation indicating treatment with cardioversion.

40. A system for predicting whether a subject with a history of atrial fibrillation will have recurrence of atrial fibrillation following a cardioversion procedure, comprising:
  means for measuring at least one MMP level from a body fluid from the subject; and
  a processing unit configured to produce an MMP profile based on the measured MMP level and to compare the at least one MMP level to a corresponding control MMP level to determine the relative increase or decrease of each respective MMP level in the MMP profile, wherein the processing unit is further configured to analyze the MMP profile to determine whether the subject will have a recurrence of atrial fibrillation following the cardioversion procedure.

41. A system for predicting whether a subject with a history of atrial fibrillation will have recurrence of atrial fibrillation following a cardioversion procedure, comprising:
  means for measuring at least one TIMP level from a body fluid from the subject; and
  a processing unit configured to produce a TIMP profile based on the measured TIMP level and to compare the at least one TIMP level to a corresponding control TIMP level to determine the relative increase or decrease of each respective TIMP level in the TIMP profile, wherein the processing unit is further configured to analyze the TIMP profile to determine whether the subject will have a recurrence of atrial fibrillation following the cardioversion procedure.

42. A system for predicting whether a subject with a history of atrial, fibrillation will have recurrence of atrial fibrillation following a cardioversion procedure, comprising:
  means for measuring at least one MMP level and at least one TIMP level from a body fluid from the subject; and
  a processing unit configured to produce an MMP/TIMP profile based on the measured MMP and TIMP levels and to compare the MMP and TIMP levels to corresponding control MMP and TIMP levels to determine the relative increase or decrease of each respective MMP and TIMP level in the MMP/TIMP profile, wherein the processing unit is further configured to analyze the MMP/TIMP profile to determine whether the subject will have a recurrence of atrial fibrillation following the cardioversion procedure.

43. A system for predicting whether a subject with a history of atrial fibrillation will have recurrence of atrial fibrillation following a cardioversion procedure, comprising:
  means for measuring at least one MMP level from a body fluid from the subject; and
  a processing unit configured to produce an MMP profile based on the measured MMP level and to compare the at least one MMP level to a corresponding control MMP level to determine the relative increase or decrease of each respective measured MMP level, wherein the produced MMP profile is indicative of the likelihood of recurrence of atrial fibrillation in the subject.

44. A system for predicting whether a subject with a history of atrial fibrillation will have recurrence of atrial fibrillation following a cardioversion procedure, comprising:
  means for measuring at least one TIMP level from a body fluid from the subject; and
  a processing unit configured to produce a TIMP profile based on the measured TIMP level and to compare the at least one TIMP level to a corresponding control TIMP level to determine the relative increase or decrease of each respective measured TIMP level, wherein the produced TIMP profile is indicative of the likelihood of recurrence of atrial fibrillation in the subject.

45. A system for predicting whether a subject with a history of atrial fibrillation will have recurrence of atrial fibrillation following a cardioversion procedure, comprising:
  means for measuring at least one MMP level and at least one TIMP level from a body fluid from the subject; and
  a processing unit configured to produce an MMP/TIMP profile based on the measured MMP level and TIMP level and to compare at least one measured MMP level and at least one measured TIMP level to a corresponding control MMP and TIMP level to determine the relative increase or decrease of each respective measured MMP and TIMP level, wherein the produced MMP/TIMP profile is indicative of the likelihood of recurrence of atrial fibrillation in the subject.

46. A method for predicting whether a subject with a history of atrial fibrillation and treated with cardioversion will have recurrence of atrial fibrillation following the administered cardioversion procedure, comprising:
  measuring at least one MMP level in a body fluid from the subject to produce an MMP profile; and
  using the MMP profile to determine whether the subject will have a recurrence of atrial fibrillation following the administered cardioversion procedure.

47. The method of claim 46, wherein use of the MMP profile comprises comparing the plurality of MMP levels of the profile to a plurality of corresponding MMP levels from the subject prior to the cardioversion procedure to determine the relative increase or decrease of each MMP level in the MMP profile.

* * * * *